US006407311B1

(12) United States Patent
Feldman et al.

(10) Patent No.: US 6,407,311 B1
(45) Date of Patent: Jun. 18, 2002

(54) METHODS FOR PRODUCTION OF HYBRID WHEAT

(75) Inventors: Moshe Feldman, Karmei Yosef; Eitan Millet, Rehovot Post, both of (IL)

(73) Assignees: Yeda Research & Development Co., Ltd.; Weizmann Institute of Science, Rehovat, both of (IL)

( * ) Notice: Subject to any disclaimer, the term of this patent is extended or adjusted under 35 U.S.C. 154(b) by 0 days.

(21) Appl. No.: 09/214,914

(22) PCT Filed: May 14, 1998

(86) PCT No.: PCT/IL98/00220

§ 371 (c)(1),
(2), (4) Date: Mar. 9, 1999

(87) PCT Pub. No.: WO98/51142

PCT Pub. Date: Nov. 19, 1998

(30) Foreign Application Priority Data

May 15, 1997  (IL) ................................................. 120835

(51) Int. Cl.[7] ................................................ A01H 1/00

(52) U.S. Cl. ........................ 800/274; 800/260; 800/266; 800/267; 800/320.3; 800/320

(58) Field of Search ................................ 800/274, 260, 800/266, 267, 320.3, 320

(56) References Cited

U.S. PATENT DOCUMENTS

| 4,143,486 A | 3/1979 | Maan .............................. 47/58 |
| 4,680,888 A | 7/1987 | Tsunewaki et al. ............ 47/58 |

FOREIGN PATENT DOCUMENTS

| WO | WO 92/01366 | 2/1992 |
| WO | WO 93/13649 | 7/1993 |

OTHER PUBLICATIONS

Walter R. Fehr, Principles of Cultivar Development: Theory and Technique, p. 362, 1987.*
Driscoll, C.J., "XYZ System of Producing Hybrid Wheat," Crop Science, vol. 12, pp. 516–517, 1972.
Driscoll, C.J., "Modified XYZ System of Producing Hybrid Wheat," Crop Science, vol. 25, pp. 1115–1116, 1985.
Tsujimoto, H. & Tsunewaki, K., "Genetic Analyses on a Gametocidal Gene Originated from *Aegilops Aucheri*," Proc. 6th International Wheat Genetics Symposium, pp. 1077–1081, 1983.
Sasakuma, T., et al., "EMS–Induced Male–Sterile Mutants in Euplasmic and Alloplasmic Common Wheat," Crop Science, vol. 18, pp. 850–853, 1978.
Franckowiak, J.D., et al., "A Proposal for Hybrid Wheat Utilizing *Aegilops squarrosa* L. Cytoplasm," Crop Science, vol. 16, pp. 725–728, 1976.

Hermsen, J.G., "Towards a More Efficient Utilization of Genic Male Sterility in Breeding Hybrid Barley and Wheat," Euphytica, vol. 14, pp. 221–224, 1965.

Keppenne, V.D. & Baenziger, P.S., "Inheritance of the Blue Aleurone Trait in Diverse Wheat Crosses," Genome, vol. 33, pp. 525–529, 1990.

Kihara, H., "Substitution of Nucleus and its Effects on Genome Manifestations," Cytologia, vol. 16, pp. 177–193, 1951.

(List continued on next page.)

Primary Examiner—Bruce R. Campell
Assistant Examiner—Anne Marie Grünberg
(74) Attorney, Agent, or Firm—Foley & Lardner

(57) ABSTRACT

The present invention provides a method for the production of hybrid wheat based on the ability to stably maintaining a genic male-sterile female parental line of common and durum wheat It also provides a male-sterile female line homozygous for a recessive male-sterility allele and for a dominant pollen-killing allele, and a maintainer line which is readily and stably propagated. The maintainer line is isogenic to the female line but has an alien engineered chromosome carrying a dominant male-fertility allele that restores fertility to the maintainer line, a recessive pollen-killing allele that is susceptible to the killing effect of the native pollen killer thus preventing transmission of this chromosome to the female line, and one or more selectable markers that facilitate the maintenance of the maintainer itself. The invention also provides procedures for converting any desired cultivar into male-sterile female line and into a maintainer line.

64 Claims, 32 Drawing Sheets

OTHER PUBLICATIONS

Loegering, W.Q. & Sears, E.R., "Distorted Inheritance of Stem–Rust Resistance of Timstein Wheat Caused by a Pollen–Killing Gene," Canadian Journal of Genetics & Cytology, vol. 5, No. 1, pp. 65–72, 1963.

Lukaszewski, A., "Reconstruction in Wheat of Complete Chromosomes 1B and 1R from the 1RS.1BL Translocation of 'Kavkaz' Origin," Genome, vol. 36, pp. 821–824, 1993.

Sears, E.R., "Chromosome Engineering in Wheat," Stadler Symposia, vol. 4, pp. 23–38, 1972.

Sears, E.R., "An Induced Mutant with Homoeologous Pairing in Common Wheat," Canadian Journal of Genetics and Cytology, vol. 14, No. 4, pp. 585–593, 1977.

Sharma, D. & Knott, D.R., "The Transfer of Leaf–Rust Resistance from Agropyron to Triticum by Irradiation," Canadian Journal of Genetics and Cytology, vol. 8, No. 1, pp. 137–138, 1966.

Casely, J.C., et al., "Herbicide Resistance in Weeds and Crops," Butterworth–Heinemann, Oxford, UK, pp. 305–317, 1991.

Zeven, A.C., "Wheats with Purple and Blue Grains: A Review," Euphytica, vol. 56, pp. 243–258, 1991.

* cited by examiner

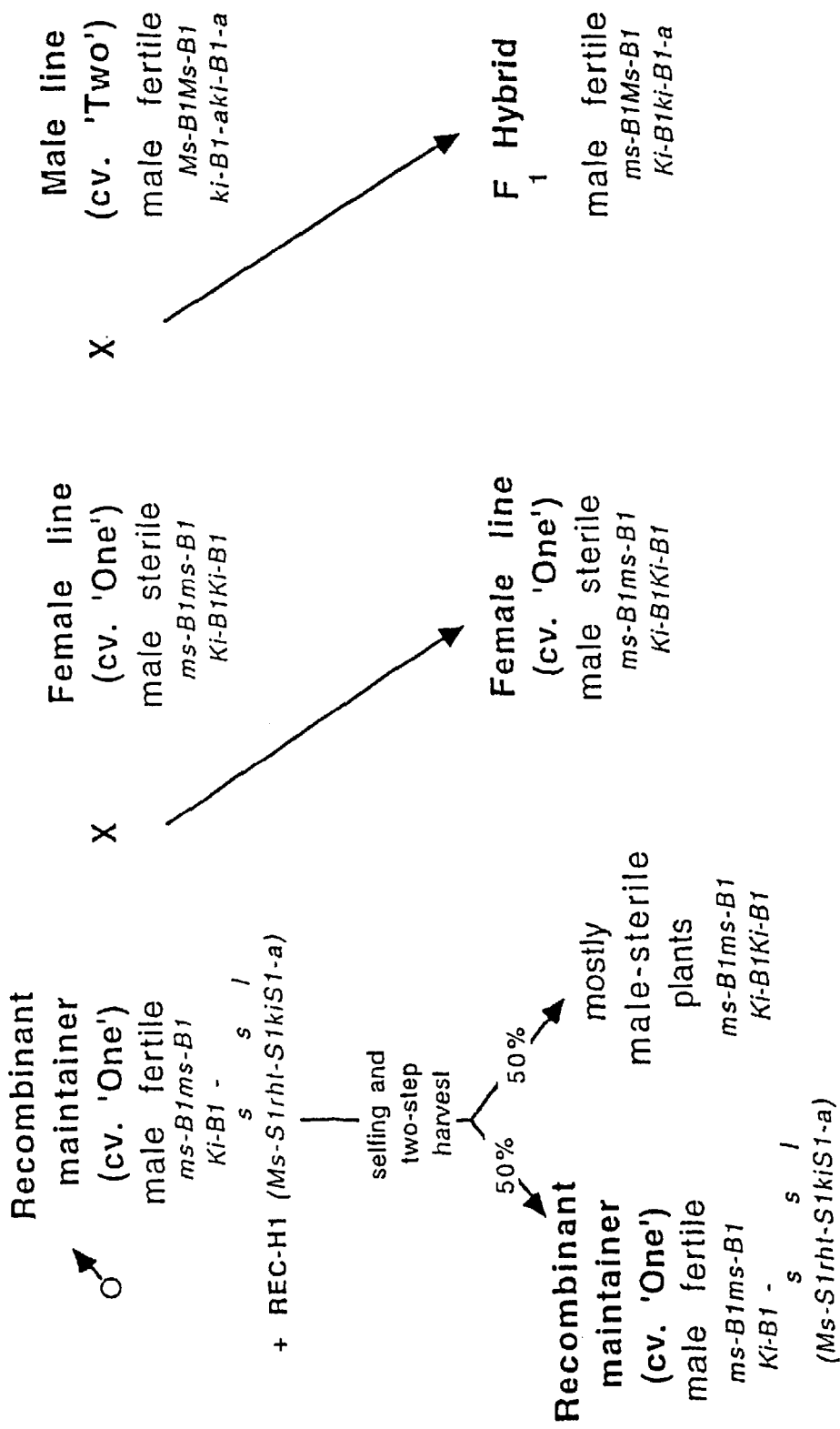
Fig_13b

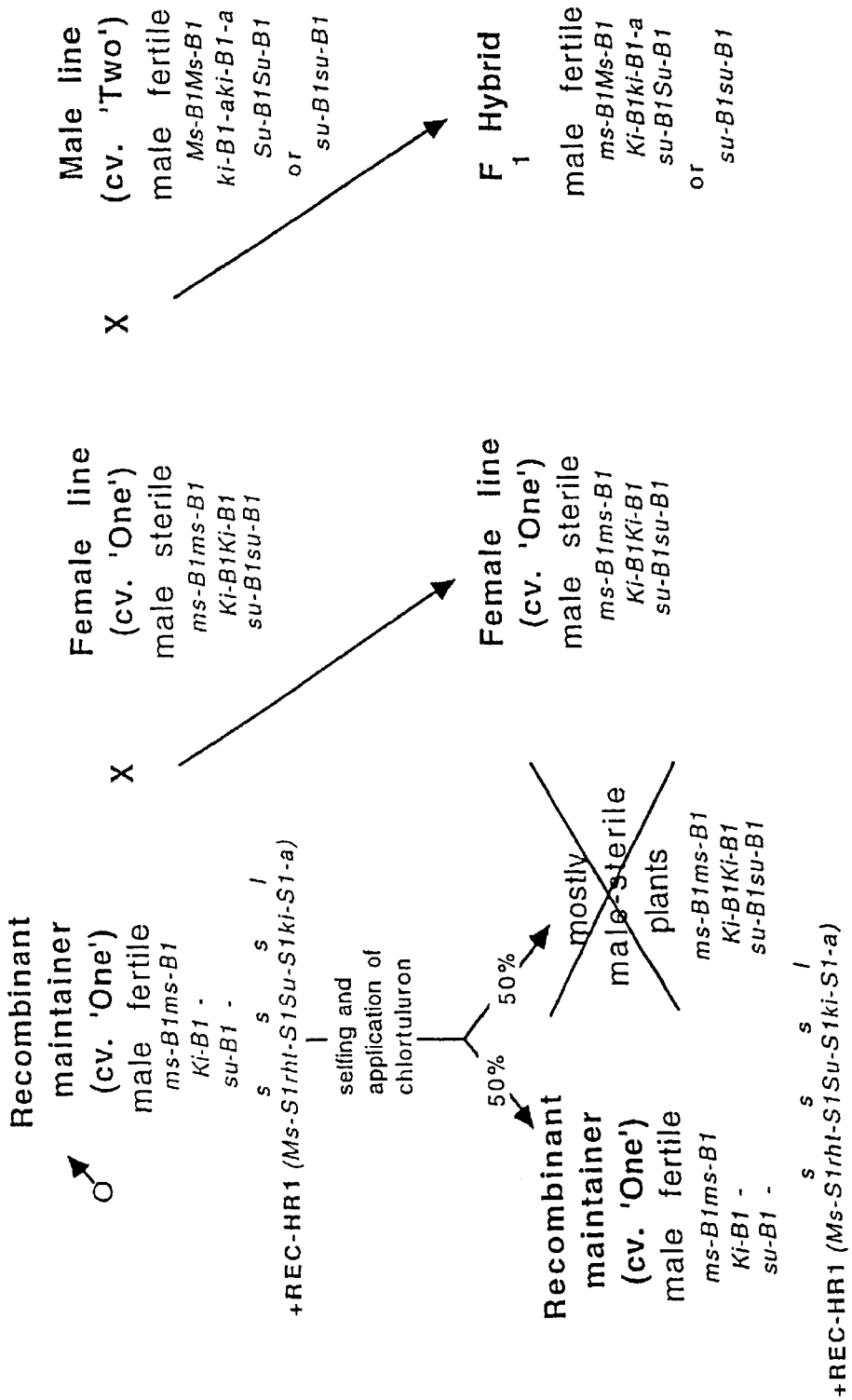
Fig_14b

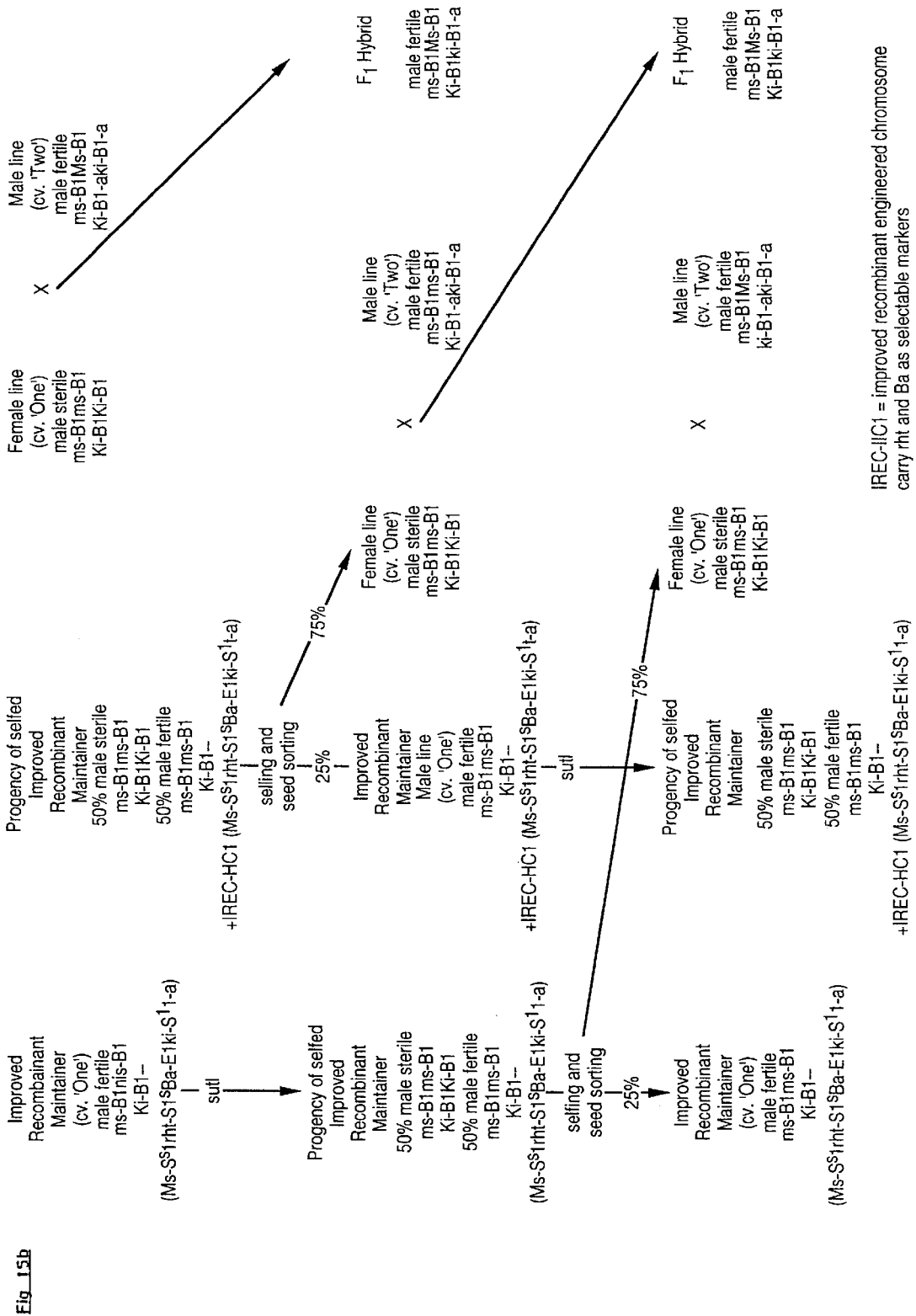

METHODS FOR PRODUCTION OF HYBRID WHEAT

FIELD OF THE INVENTION

The present invention concerns the production of hybrid seeds of common and durum wheat that yield hybrid plants that are highly heterozygous and phenotypically uniform. More specifically, the present invention concerns a new method, based on chromosome engineering, for maintaining a male-sterile female parental line for use in the production of hybrid wheat plants, which female line is homozygous for a recessive mutant male-sterility allele, for a recessive marker allele(s) and for a dominant pollen-killer allele, and a new maintainer line for maintaining the female parental line which is isogenic to the female line but has an additional alien engineered chromosome carrying a dominant male-fertility allele, a recessive pollen-killer allele susceptible for a pollen-killing of the dominant native pollen-killer allele, and a dominant selectable marker allele(s). All the alleles on the alien chromosome arm are permanently linked due to lack of pairing and recombination between the alien and the wheat chromosomes. The presence of the recessive pollen-killer allele on the alien engineered chromosome ensures that all the maintainer viable male gametes will lack this chromosome and consequently, the dominant male-fertility allele and the selectable marker allele. On one hand, about 20-50% of the female gametes will carry the alien engineered chromosome. When the selectable marker is an allele affecting plant height (plants carrying the engineered chromosome are taller by 8–10 cm from those not carrying it), it is possible to harvest the tall plants separately from the short plants. From the seeds that are developed on the tall plants about 20–50% carry the alien engineered chromosome and therefore, they will develop into male-fertile plants, and 50–80% lack this chromosome and will develop into male-sterile plants. The ability to harvest separately, each year, the seeds of the tall plants keeps constant the proportion of the male-fertile plants in the maintainer. When the selectable marker is a herbicide resistance gene (e.g., resistance to chlorotoluron), it is possible to apply the herbicide onto the progeny of the selfed maintainer, thereby to kill all the plants that lack the engineered chromosome (the male-sterile plants) while only the maintainer (the male-fertile) plants survive. This makes it possible to grow in each generation only the male-fertile plants from the progeny of the selfed maintainer. When the selectable marker is blue aleurone (an endosperm coloring trait), it is possible to separate the seeds that were developed on the maintainer line into blue seeds from which male-fertile plants (maintainer line) are developed, and natively colored (red/white) seeds from which male-sterile plants (female line) are developed. The possibility to sort out the seeds of the male-sterile female line directly from the progeny of the selfed maintainer line simplifies the system and reduces to a great extent the production cost of the hybrid seeds. The invention further provides new methods for producing the maintainer line, new methods for converting a desired cultivar into a male-sterile female line and a maintainer line for the female line, and a new method for hybrid wheat production in which the resulting hybrid plants are all heterozygous for the recessive mutant male-sterility allele and are, therefore, male-fertile.

BACKGROUND OF THE INVENTION

It has been well established that many hybrid plant lines have higher yields than pure, true breeding plant lines, and exhibit improved quality and greater tolerance to environmental and biotic stresses. Unlike corn in which male and female flowers are physically separated, common (bread) (*Triticum aestivum* var. *aestivum*) and durum (macaroni) (*T. turgidum* var. *durum*) are predominantly self-pollinating species and every flower contains both female and male organs. To produce hybrid seeds, it is therefore necessary to male-sterilize the female parent. Since hand emasculation is impractical in wheat, male-sterility may be brought about by application of chemical hybridizing agents (CHAs) or by genetic means. Utilization of a CHA to male-sterilize wheat plants is expensive, inefficient and pollutant. Indeed, the use of CHAs is currently mainly confined to scientific experiments.

The following conditions are required for the production of hybrid seeds by genetic means: 1) Complete and stable male-sterility of the female parent; 2) Complete and stable fertility restoration by the male parent; 3) Easy propagation of the female (male-sterile) parent by a maintainer line. Although these conditions are known to wheat geneticists there has, however, not been a breakthrough in hybrid wheat production during the 46 years since the first male-sterile wheat was described (Kihara, 1951).

There are two main types of genetic male-sterility that can be exploited for hybrid seed production: cytoplasmic male-sterility (CMS) in nuclear substitution or alloplasmic lines, caused by the incompatible interaction of an alien cytoplasm with the common wheat nucleus, and genic male-sterility (GMS) in euplasmic lines, caused by a recessive mutation or a deletion of a nuclear gene(s) which normally confers male-fertility in common wheat cytoplasm. It should be noted that CMS which involves an alien cytoplasm, usually reduces the yielding capacity of the hybrid, while GMS which involves a native cytoplasm should allow for a normal expression of the genome, and hence a full yielding capacity of the hybrid.

Whereas in many commercial crops (e.g. corn) it is the genic male-sterility which prevails, this type has not yet been fully exploited in common or durum wheat. Most attempts in common wheat have been directed to producing hybrid seeds on the basis of cytoplasmic male-sterility. In this respect, the cytoplasm (G cytoplasm) of another species of wheat, *Triticum timopheevii*, was widely used. Alloplasmic lines containing this cytoplasm are male-sterile. Another type of cytoplasm that was studied is that of *Aegilops variabilis* (the $S^v$ cytoplasm). This cytoplasm causes male-sterility in lines deficient for a $S^v$ restorer on chromosome arm 1BS. However, as noted above, the use of an alien cytoplasm as a sterilizing factor in common wheat has a major drawback since various important traits are negatively affected by the interaction between the common wheat nucleus and the alien cytoplasm. In addition, it has been difficult to find stable fertility restoration genes for such alloplasmic male-sterile lines, which are highly effective in a wide range of genotypes. Moreover, the system requires breeding of the male parent too (e.g. introduction of genes that can restore male-fertility to the alien cytoplasm), thus rendering hybrid seed production more expensive and limiting the number of male parents that can be tested for combining ability (contribution to a significant hybrid vigor).

Genic male sterility, on the other hand, is expressed in a normal common or durum wheat cytoplasm. Hence, no cytoplasm-induced deleterious effects on plant performance are expected. Further, using a female parent homozygous for a recessive male-sterility allele, any wheat cultivar which is by its nature homozygous for the dominant allele conferring male-fertility, can be used as a male parent that will restore complete fertility to the $F_1$ hybrids. There is no need to breed for male lines and no limitation exists for the number of males which can be crossed with the male-sterile females and evaluated for their combining ability.

Several chromosome arms have been described in common wheat which carry genes affecting male-fertility, e.g. chromosome arms of group 4: the long arm of chromosome 4A (4AL), the short arm of chromosome 4B (4BS) and the short arm of chromosome 4D (4DS), carrying the normal male-fertility Ms-A1, Ms-B1 and Ms-D1 genes, respectively, and the long arms of the group 5 chromosomes: 5A, 5B and 5D (5AL, 5BL and 5DL, respectively), carrying the Ms-A2, Ms-B2 and Ms-D2 genes, respectively. However, until now, only in the Ms-B1 locus, on the distal region of chromosome arm 4BS (formerly 4AS) were three recessive alleles found or induced that cause male sterility. These alleles, namely, ms-B1-a, ms-B1-b and ms-B1-c (often also called ms1a, ms1b and ms1c, respectively), were reported not to cause any effect, beyond male-sterility, on plant performance (reviewed by Wilson & Driscoll, 1983).

Maintenance of the male-sterile female lines remains the major obstacle for a successful hybrid production system based on GMS. Efforts were made to maintain the male-sterile females in two directions. One was the use of a 'fertilizing cytoplasm' and another was to equip the maintainer with an alien fertility allele homoeoallelic to the recessive mutant male-sterility allele, which is not transmitted into the female line.

The first approach of maintaining the male-sterile female, i.e. the use of a 'fertilizing cytoplasm', was proposed long ago by Hermsen (1965) but up to now was not supported by experimental results. He described a possibility of a 'fertilizing cytoplasma', i.e. a native or alien cytoplasm in which the male-sterility in plants homozygous for a male-sterility allele is not expressed, and therefore the line is phenotypically male-fertile. Unfortunately, so far no such cytoplasm was found. The system proposed by Hermsen could not be practically realized mainly because there is not sufficient intra-specific variation of cytoplasm in common wheat that can restore fertility to a male-sterile genotype, and cytoplasms of closely related species of wheat also cannot facilitate the restoration of male-fertility to male-sterile genotypes. On the other hand, the cytoplasm of more distant species usually causes male-sterility except in cases when the alloplasmic line carries a suitable restorer(s). However, as such, their effect on male-sterility alleles was not studied.

Franckowiak et al. (1976) ascribed male-fertility restoring genes to the D genome of common wheat, since alloplasmic common wheat (genome AABBDD) in *Aegilops squarrosa*. (D) cytoplasm is male-fertile and alloplasmic durum wheat (genome AABB) in D cytoplasm is male-sterile. They induced mutations in an alloplasmic line of common wheat with D cytoplasm and proposed a hybrid production system in which such alloplasmic male-sterile parent is maintained by an euplasmic type of the same cultivar, i.e. the female, male-sterile parent will have a male-fertility mutated allele an4 a D cytoplasm, the maintainer will have the same mutated allele and a native (B) cytoplasm and the male parent will have the normal male-fertility allele and the B cytoplasm. Fertility in the hybrid is restored by crossing such male and female parents. However, such hybrids will all have the D cytoplasm derived from the female parent, this being undesirable in view of the fact that such a cytoplasm may have deleterious effects on the performance (yield, vigor, etc.) of the hybrids. Moreover, in the above system of Franckowiak et al., the maintainer line, for obtention in subsequent generations of the male-sterile female parent, is a line carrying the male-sterility mutation and a B cytoplasm to ensure fertility of the maintainer line. This system turned out to be unpractical in view of the fact that all the male-sterility mutants that were obtained were also sterile in the B cytoplasm (Sasakuma et al., 1978). Hence, the so-proposed 'maintainer' line was also male-sterile, and of no practical value. Accordingly, because of the absence of a suitable maintainer line, the system of Franckowiak et al. has been abandoned.

In a similar manner to the above, Feldman and Millet (unpublished data) found that genotypes carrying male-sterility alleles on B genome chromosomes, e.g., 4B and 5B, are also male sterile in alloplasmic lines containing D and $S^v$ cytoplasms. It seems therefore, that the concept of 'fertilizing cytoplasm' (Hermsen, 1965) can not be realized in wheat.

An example of the second approach of maintaining the male-sterile female is the XYZ system of Driscoll (1972). Two decades ago he suggested to add into the male-sterile female Z line (homozygous for the recessive mutant allele ms-B1-c) an extra single (in Y line) or a pair (in X line) of an alien chromosome carrying the dominant Ms homoeoallele which, in turn, confers fertility to X and Y lines. The alien chromosome does not pair with its wheat homoeologous chromosomes and in the Y line (maintainer) is transmitted through the pollen in a very low frequency and thus the pollinated male-sterile female line produces seeds, most of which will germinate into male-sterile plants. Since the maintainer (Y) is not a true-breeding line, it is produced by pollinating the male-sterile female (Z) by the disomic alien addition line (X). This system was characterized by two major drawbacks: some transmission of the alien chromosome occurred through the pollen of the maintainer line which introduced male fertility to the new generation of the male-sterile female line; and addition decay occurred in the X line impairing its purity. These are possibly the reasons why this system has never come into practical (commercial) use.

More recently, Driscoll (1985) proposed a modification of the above XYZ system of producing hybrid wheat. In this system, a selfed Y-line replaces the Y-line to maintain and propagate the male-sterile Z-line. This modification eliminates the need for the X-line which was originally needed to generate a large quantity of Y-line plants. Moreover, the newly proposed Y-line carries an alien isochromosome so that the compensating male-fertility homoeoallele is in two doses. While the modified XYZ system requires fewer crosses between the various parental plants in order to maintain and propagate the male-sterile female plants, than the original XYZ system, the drawbacks characterizing the original XYZ system as noted above, do however, also exist in the modified XYZ system and limit its use in commercial production of hybrid seeds.

In view of the above, it therefore seems that traditional methods of hybrid production are not efficient enough and new approaches are needed. One such new approach, based on an improvement of the above XYZ system of Driscoll (1972), has been described in the International PCT Patent Application Nos. PCT/AU91/00319 (WO 92/01366) and PCT/AU93/00017 (WO93/13649), which concern the production of hybrid cereal crops such as common wheat. In these publications there are described plant lines used for the production of hybrids which have an alien chromosome or chromosome segment bearing a dominant male-fertility gene homoeoallelic to the male-sterility mutant allele and a color marker gene conferring coloration on the progeny seed. The maintenance of the male-sterile (female) parental line is accomplished by physically separating the progeny seeds by color sorting. Such genetically-altered common wheat plants contain a modified chromosome with a dominant normal male-fertility allele from the diploid wheat *Triticum monococcum* as an addition or substitution for one of the wheat 4B chromosomes. The modified chromosome carries the short arm of chromosome $4A^m$ of *T. monococcum* ($4A^mS$) carrying the Ms-$A^m1$ allele and a second arm with a proximal segment from the long arm of either chromosome $4A^m$ of *T. monococcum* ($4A^mL$) or chromosome 4E of *Agropyron elongatum* (4EL) with the coloration allele (C) and a distal segment of wheat chromosome arm 4BL. Part of this modified chromosome is homologous and part of it is homoeologous to the wheat chromosome 4B bearing the recessive male-sterility allele. The homologous part, i.e. the distal region of 4BL can pair with the normal wheat 4BL, thus ensuring regular segregation at meiosis. Another possibility to mark this chromosome carrying the normal dominant male-fertility allele, Ms-$A^m1$, is by the use of a gene conferring increased plant height on progeny plants.

However, the above hybrid-production system has a number of drawbacks as regards the efficient maintenance of the parental lines. First, pollination of female plants by the maintainer will yield a larger number of seeds with the recombinant alien/4BL chromosome which will develop into male-fertile plants. Secondly, the maintenance of the male-sterile female parent involves a complex procedure of progeny selection based on marker genes. Thirdly, the maintainer line for the female (male-sterile) parental line is also a genetically unstable line in that it carries 20 pairs of normal common wheat chromosomes, one 4B chromosome carrying the male-sterility (ms-B1-b) mutant allele (known as 'Probus') (Wilson and Driscoll, 1983) and one recombinant alien group 4/4BL chromosome having the normal, male-fertility Ms-$A^m1$ allele and the seed coloration allele. Thus, the maintainer line is male-fertile, and upon selfing will yield fertile plants homozygous or heterozygous for the modified chromosome. It will thus be impossible to distinguish between the two genotypes on the basis of the coloration gene and very difficult on the basis of the height gene. Hence, the propagation of the maintainer and its use to provide the male-sterile female line is laborious and not practical for large-scale commercial applications.

To overcome the difficulties of mechanical or other indirect means of selection against the alien chromosome carrying the male fertility Ms allele, T. R. Endo, Kyoto University, Kyoto, Japan, suggested (as cited by Tsujimoto and Tsunewaki 1983) to use the gametocidal gene Gc1 and link it to the male sterility allele ms. The gametocidal allele, originated from *Ae. speltoides*, brings about abortion of gametes not carrying it (but rather carrying the native recessive gc1 allele). According to Endo's proposal, the male-sterile female line is homozygous for both ms and Gc1, which are tightly linked, while a male-fertile line (the maintainer) isogenic to the female line but having Ms and gc1 alleles, is used to pollinate the female line to yield a double heterozygote msMsGc1gc1. Due to abortion of gametes carrying gc1, all the progeny of such selfed line will be homozygote msmsGc1Gc1 and identical to the female line. However, according to their proposal the male line (R line) in the hybrid production system should also be bred to contain the Gc1 allele otherwise the fertility of the $F_1$ hybrid will be reduced. Moreover, Gc1 causes the abortion of female as well as male gametes and therefore, a cross (between the female and the maintainer) and a self (of the double heterozygote) are required each year to renew the female seed stock. This is a drawback in time and cost. Another disadvantage of Endo's proposal stems from the fact that the male-sterile female parent contains an alien chromosome segment carrying the Gc1 allele that was derived from *Ae. speltoides*. This segment may carry also alleles with negative effect on the performance of the female, increasing the cost of hybrid seed production, or even affecting the yield of the hybrid.

As regards the importance of common wheat hybrid production, it should be noted that different reports on experimental hybrid performance indicate a yield increase of the best wheat hybrids of up to 30% above the leading best cultivars (Wilson and Driscoll, 1983). Further, it is well known that many hybrids exhibit an improved quality and greater tolerance to environmental and biotic stresses than the conventional cultivars. It is generally assumed that the relatively small advantage of hybrid wheat over true-breeding cultivars resuls from a continuous selection for high performance of homozygous germplasm. Hence it is anticipated that selection for improved performance of heterozygous germplasm may result in significantly increased yield in a short period of time.

Since hybrids are based on current cultivars which, in turn, are improved continuously by conventional breeding methods, it is thus advantageous to be able to convert every newly developed or newly released cultivar into a potential female. This is essential not only to survey the combining ability of newly released plant material but, more importantly, to commercially produce new hybrids as their market is reserved only when a considerable gap is maintained between hybrids and the newly released pure lines.

DEFINITIONS

Throughout the description and the claims, the following terms and abbreviations will be used:

Common wheat=bread wheat, *Triticum aestivum* var. *aestivum*, being an allohexaploid species (2n=42) having the three genomes ABD.

Durum wheat=macaroni wheat, *Triticum turgidum* var. *durum*, being an allotetraploid species (2n=28) having the two genomes AB.

*Triticum monococcum*=a diploid species (2n=14) containing wild (var. boeoticum) and cultivated (var. monococcum) taxa, closely related to the diploid donor of the A genome of durum and common wheat, having genome Am whose chromosome $4A^m$ is homoeologous (partially homologous) to chromosome 4A as well as to other group-4 chromosomes of durum and common wheat.

*Aegilops longissima* and *Aegilops searsii*=diploid species (2n=14), closely related to the donor of the B genome of durum and common wheat having genomes $S^l$ and $S^s$, respectively, whose chromosomes are homoeologous (partially homologous) to those of wheat.

*Agropyron elongatum*=a complex species including diploid (2n=14), tetraploid (2n=28) and decaploid (2n=70) taxa, related to durum and common wheat, having the E genome (the polyploids are autopoliploids) whose chromosomes are homoeologous to those of durum and common wheat.

4BS=the short arm of chromosome 4B (formerly 4A) of common and durum wheat. wheat.

6BL=the long arm of chromosome 6B of common and durum wheat.

$4A^mS$ and $4A^mL$=the short and the long arms, respectively, of chromosome $4A^m$ of *Triticum monococcum*.

4EL=the long arm of chromosome 4E of *Agropyron elongatum*.

4S$^s$S=the short arm of chromosome 4S$^s$ of *Aegilops searsii*.

4S$^l$S=the short arm of chromosome 4S$^l$ of *Aegilops longissima*.

6S$^s$L=the long arm of chromosome 6S$^s$ of *Aegilops searsii*.

6S$^l$L=the long arm of chromosome 6S$^l$ of *Aegilops longissima*.

Ms=a dominant allele responsible for male-fertility in wheat.

Ms-B1=a dominant allele for male-fertility in durum and common wheat located on 4BS.

ms=a recessive mutant allele of Ms that confers male-sterility.

ms-B1=a recessive mutant allele of Ms-B1, that confers male-sterility in durum and common wheat, when present in homozygous state.

ms-B1-a=ms1a which is the 'Pugsley' mutant ms-B1 allele.

ms-B1-b=ms1b which is the 'Probus' mutant ms-B1 allele.

ms-B1-c=ms1c which is the 'Cornerstone' mutant ms-B1 allele.

Ms-S$^s$1=a dominant allele for male-fertility, homoeoallelic to Ms-B1, on 4S$^s$S.

Ms-S$^l$1=a dominant allele for male-fertility, homoeoallelic to Ms-B1, on 4S$^l$S.

Ms-A$^m$1=a dominant allele for male-fertility, homoeoallelic to Ms-B1, on 4A$^m$S.

Ki-B1=a dominant pollen-killer allele on 6BL of common wheat, inducing the killing of pollen carrying ki-B1-a or ki-S$^l$1-a.

ki-B1-a=a recessive pollen-killer allele on 6BL of common wheat; pollen carrying it is killed in plants possessing Ki-B1.

ki-B1-n=a neutral pollen-killer allele on 6BL of common wheat; pollen carrying it is neither killed in plants possessing Ki-B1 nor it induces killing of pollen carrying ki-B1-a or ki-S$^l$1-a.

ki-S$^l$1-a=a pollen-killer allele on 6S$^l$L of *Aegilops longissima*; pollen carrying it is killed in plants possessing Ki-B1.

Rht1 and Rht2=recessive or partially recessive alleles, located on chromosome arms 4BS and 4DS, respectively, that are inducing a reduced plant height.

rht=a dominant or semi-dominant allele determining normal plant height (tall plant).

rht-S$^s$1=a dominant or semi-dominant allele on 4S$^s$S determining normal plant height (tall plant).

rht-S$^l$1=a dominant or semi-dominant allele on 4S$^l$S determining normal plant height (tall plant).

rht-A$^m$1=a dominant or semi-dominant allele on 4A$^m$S determining normal plant height (tall plant).

Su-B1=a dominant allele on 6BL of hexaploid and tetraploid wheat that confers resistance to the herbicide chlorotoluron [3-(3-chloro-p-tolyl)-1,1-dimethylurea] and to other phenylurea herbicides {e.g., metoxuron [3-(3-chloro4-metoxyphenylyl)-1,1-dimethylurea]}. Any herbicide resistant gene can be used in the context of the invention.

su-B1=a recessive allele of Su-B1 found on 6BL of hexaploid and tetraploid wheat; plants carrying it are susceptible to chlorotoluron.

su-S$^l$1=a recessive allele, homoeoallelic to Su-B1, found on 6S$^l$L of *Aegilops longissima*; plants carrying it are susceptible to chlorotoluron.

Su-S$^s$1=a dominant allele, homoeoallelic to Su-B1, found on 6S$^s$L of *Aegilops searsii*; conferring resistance to chlorotoluron.

Ba=a dominant allele determining blue coloring of the aleurone layer of the 3n endosperm.

Ba-A$^m$1=a dominant allele for blue aleurone color on 4A$^m$L.

Ba-E1=a dominant allele for blue aleurone color on 4EL.

Ph1=a dominant allele on the long arm of chromosome 5B of common and durum wheat that suppresses pairing of homoeologous chromosomes.

ph1b=a recessive mutant allele that allows homoeologous pairing.

cv.=cultivar.

EC=an engineered chromosome consisting of segments derived from two or more different alien chromosomes, carrying a Ms allele, a ki allele and a selectable marker(s) by which plants having this chromosome can be selected.

EC-H=an engineered chromosome carrying a rat allele (plant height) as a selectable marker.

EC-H1=an engineered chromosome consisting of 4S$^s$S/6S$^l$L carrying Ms-S$^s$1, rht-S$^s$1 and ki-S$^l$1-a (FIG. 2a).

EC-HR=an engineered chromosome carrying a rht allele (plant height) and a Su allele (resistance to the herbicide chlorotoluron) as selectable markers.

EC-HR1=an engineered chromosome consisting of 4S$^s$S/6S$^l$L carrying Ms-S$^s$1, rht-S$^s$1, Su-S$^s$1 and ki-S$^l$1-a (FIG. 2b).

REC=a recombinant engineered chromosome consisting of segments derived from two or, more different alien chromosomes and from the distal segment of the native chromosome-arm 6BL, carrying a Ms allele, a ki-S$^l$1-a allele and a selectable marker(s) by which plants having this chromosome can be selected.

REC-H=a recombinant engineered chromosome carrying a rht allele as a selectable marker.

REC-H1=a recombinant engineered chromosome consisting of 4S$^s$S/6S$^l$L/6BL carrying Ms-S$^s$1, rht-S$^s$1 and ki-S$^l$1-a (FIG. 2c).

REC-HR=a recombinant engineered chromosome carrying a rht and a Su allele as selectable markers.

REC-HR1=a recombinant engineered chromosome consisting of 4S$^s$S/6S$^1$L/6BL carrying Ms-S$^s$1, rht-S$^s$1, Su-S$^s$1 and ki-S$^l$1-a (FIG. 2d).

IEC=an improved engineered chromosome consisting of segments derived from two or more different alien chromosomes carrying, in addition to the Ms, ki and the selectable marker alleles, a seed marker by which seeds having this chromosome can be separated from seeds not having it.

IEC-HC=an improved engineered chromosome carrying rht (plant height) and Ba (seed color) as selectable markers.

IEC-HC1=an improved engineered chromosome consisting of 4S$^s$S/4EL/6S$^l$L carrying Ms-S$^s$1, rht-S$^s$1, Ba-E1 and ki-S$^l$1-a (FIG. 3a).

IEC-HC2=an improved engineered chromosome consisting of 4S$^s$S/4A$^m$L/6S$^l$L carrying Ms-S$^s$1, rht-S$^s$1, Ba-A$^m$1 and ki-S$^l$1-a (FIG. 4a).

IEC-HC3=an improved engineered chromosome consisting of 4A$^m$S-4A$^m$L/6S$^l$L carrying Ms-A$^m$1, rht-A$^m$1, Ba-A$^m$1 and ki-S$^l$1-a (FIG. 5a).

IREC=an improved recombinant engineered chromosome consisting of segments derived from two or more different alien chromosomes and from the distal segment of the native chromosome-arm 6BL, carrying, in addition to the Ms, ki and the selectable marker alleles, a seed marker by which seeds having this chromosome can be separated from seeds not having it.

IREC-HC=an improved recombinant engineered chromosome carrying rht and Ba as selectable markers.

IREC-HC1=an improved recombinant engineered chromosome consisting of 4S$^s$S/4EL/6S$^l$L/6BL carrying Ms-S$^s$1, rht-S$^s$1, Ba-E1 and ki-S$^l$1-a (FIG. 3b).

IREC-HC2=an improved recombinant engineered chromosome consisting of 4S$^s$S/4A$^m$L/6S$^l$L/6BL carrying Ms-S$^s$1, rht-S$^s$1, Ba-A$^m$1 and ki-S$^l$1-a (FIG. 4b).

IREC-HC3=an improved recombinant engineered chromosome consisting of 4A$^m$S-4A$^m$L/6S$^l$L/6BL carrying Ms-A$^m$1, rht-A$^m$1, Ba-A$^m$1 and ki-S$^l$1-a (FIG. 5b).

Maintainer line=a male-fertile line, isogenic to the male-sterile female line but contains an additional engineered chromosome of the EC type.

Recombinant maintainer line=a male-fertile line isogenic to the male-sterile female line but is monosomic for chromosome 6B and contains, as a monosomic substitution, an engineered chromosome of the REC type.

Improved maintainer line=a male-fertile line isogenic to the male-sterile female line but contains an additional engineered chromosome of the IEC type.

Improved recombinant maintainer line=a male-fertile line isogenic to the male-sterile female line but is monosomic for chromosome 6B and contains, as a monosomic substitution, an engineered chromosome of the IREC type.

SUMMARY OF THE INVENTION

In order to overcome the above mentioned drawbacks of the prior art, it is an object of the present invention to provide a method for maintaining a genic male-sterile female parental line of a common or durum wheat cultivar, which method provides for a simple means for stably maintaining the male-sterile female parental line.

Yet another object of the present invention is to provide a maintainer line for use in the above method, which maintainer line is easily, rapidly and stably propagated.

A further object of the present invention is to provide a method for producing said maintainer line.

Still another object of the present invention is to provide new methods for converting any desired common or durum wheat cultivar into a male-sterile female line and into a maintainer line.

The present invention makes possible the commercial production of hybrids of common and durum wheat. In one aspect, the invention provides a novel method for the maintenance of a male-sterile female parental line (A-line) that is homozygous for a recessive male-sterility mutant (ms) allele and for the dominant pollen-killer (Ki) allele. The maintainer (B-line) (FIG. 1) is isogenic to the female line and has further an alien engineered chromosome carrying a dominant male-fertility allele (Ms) linked to a recessive pollen-killer allele (ki), and at least one selectable marker allele. Pollen grains of the maintainer containing the engineered chromosome (Ms and ki alleles) are killed. Several types of the engineered chromosome carry as a selectable marker the rht (affecting plant height) allele, others carry the rht and Su1 (chlorotoluron resistance) alleles as two selectable markers, each for every arm, while still other types carry the rht and the Ba (inducing blue seed color) alleles as two selectable markers, each for every arm.

Thus, a simple system has been developed in accordance with the present invention, by which the male-sterile female parental line (A-line) is maintained either by pollinating it with the male-fertile maintainer line (B-line), and all of the resulting progeny are male-sterile female plants (FIG. 1a), or preferably, sorting out from the selfed progeny of the maintainer, due to differential coloring, the seeds that will develop into male-sterile female line from those that will develop into male-fertile maintainer line (FIG. 1b). Similarly, the maintainer line is itself easily maintained by self-pollination, resulting in a mixture of seeds in which about 20% carry the engineered chromosome and are therefore male-fertile, and about 80% lack this chromosome and are therefore, male-sterile. In those maintainer lines carrying only the rht allele as a selectable marker, it is possible to harvest first the taller plants containing the engineered chromosome. This selective harvest facilitates the preservation each year of a constant rate of about 20% male-fertile maintainer plants in the progeny of the selfed maintainer which includes male-sterile plants as well. In those maintainer lines carrying the rht and Su1 alleles as selectable markers, it is possible to kill with the herbicide chlorotoluron the plants lacking the engineered chromosome. This assures that every year only the male-fertile maintainer plants will grow in plots sown with the progeny of the selfed maintainer. On the other hand, in the improved maintainer lines carrying the Ba allele as a selectable marker, it is possible to separate, by a seed sorter, the blue seeds, when grown, developing into male-fertile plants, from red/white seeds, when grown, developing into male-sterile plants. This facilitates planting each year a maintainer line with 100% male-fertile plants.

According to one aspect of the present invention, the engineered chromosomes EC-H and EC-HR are translocated chromosomes that were derived from two alien chromosomes. One of their arms carries the Ms and the rht alleles and the other, the ki allele in EC-H and both Su-1 and ki alleles in EC-HR. Since the alien arms do not ordinarily pair with their wheat homoeologous chromosomes, the three alleles on EC-H and the four alleles on EC-HR are linked and do not segregate with respect to one another. EC-H (FIG. 2a) or EC-HR (FIG. 2b) is added to the maintainer in one dose, i.e., the maintainer is a monosomic addition line. The functional pollen grains of the maintainer do not contain the engineered chromosome. Hence, all the progeny resulting from a cross between the male-sterile female line and the maintainer line are male-sterile, while progeny derived from self-pollination of the maintainer line contains a mixture of genotypes of which about 20% are male-fertile and about 80% are male-sterile.

The construction of an EC in common wheat is based on the novel finding by the inventors, of a recessive pollen-killer ki-S$^l$1-a allele on the long arm of chromosome 6 of Ae. longissima (6S$^l$L) which, when present in a single dose in plants carrying the dominant pollen-killer Ki-B1 allele on chromosome 6BL of common wheat, as in a monosomic alien addition line, is not transmitted through the pollen-grains (i.e., through the male gametes). Thus, it became feasible to construct an EC-H1 carrying both the male-fertility Ms-S$^s$1 and the rht-S$^s$1 alleles of *Ae. searsii* and the pollen-killer ki-S$^l$1-a allele of *Ae. longissima*, that was produced by simultaneous centromeric mis-division of chromosomes 4S$^s$ and 6S$^l$ followed by centric fusion of 4S$^s$S and 6S$^l$L that occurred in double monosomic addition 4S$^s$ and 6S$^l$ to common wheat (FIG. 7a). This EC-H1 has the short arm of chromosome 4 of *Ae. searsii* (4S$^s$S) carrying the Ms-S$^s$1 allele proved to confer male-fertility to an hexaploid genotype homozygous for ms-B1-c, and the rht-S$^s$1 allele rendering taller plants, and the long arm of chromosome 6 of *Ae. longissima* (6S$^l$L) carrying the recessive ki-S$^l$1-a allele, rendering pollen-grains carrying it amenable to killing in the presence of Ki-B1 allele. Because pairing and recombination do not ordinarily occur between the alien engineered chromosome and its wheat homoeologous arms, the Ms-S$^s$1, rht-S$^s$1 and ki-S$^l$1-a alleles are linked, and consequently, the transmission through the pollen-grains of Ms-S$^s$1 allele is then also prevented. This enables the production of a maintainer line which is homozygous for the Ki-B1 allele on 6BL and homozygous for one of the known recessive male-sterility mutant alleles (e.g. ms-B1-c ) located on the short arm of chromosome 4B, but which male-sterility is not expressed, i.e. the maintainer line is male-fertile due to the presence of an engineered chromosome carrying the Ms-S$^s$1 allele. Pollination of the male-sterile female line by the maintainer line yields only male-sterile plants, while selfing of the maintainer line results in about 20% male-fertile and 80% male-sterile plants.

Another aspect of the present invention is to increase the proportion (from 20% to 50%) of the maintainer male-fertile genotype in the progeny of the selfed maintainer. While the proportion of 20% is sufficient for seed increase of the maintainer itself, it renders higher cost for the production of female seed because larger area of the maintainer is required for a given area of the female parent to ensure economically effective fertilization by the maintainer. Thus it is of great advantage to increase the proportion of the maintainer in its self-progeny. This may be promoted to about 50% by a modification of the EC-H, i.e., construction of a recombinant engineered chromosome, herein designated REC-H. The REC-H containing the Ms allele from *Ae. searsii*, designated REC-H1 (FIG. 2b), is produced in common wheat in the following manner (FIG. 7b): a distal segment of the wheat chromosome arm 6BL is translocated to the 6S$^l$L arm in which the translocation breakpoint is distal to the ki-S$^l$1-a allele, enabling it to pair with the 6BL chromosome. The translocation results from homoeologous pairing in double monosomic condition in the absence of Ph1, i.e., in the genotype ph1bph1b, when the EC-H1 (4S$^s$S/6S$^l$L) and 6B can pair and recombine, resulting in the production of REC-H1, i.e., 4S$^s$S/6S$^l$L/6BL. In lines homozygous for Ph1 and monosomic for normal 6B and having one dose of the REC-H1, the two chromosomes pair, almost in every meiocyte, in the homologous region (the distal region of 6BL) and segregate to opposite poles resulting in the inclusion of the REC-H1 in one half of the gametes.

Yet, another aspect of the present invention is to keep constant the ratio of 1 male-fertile:4 male-sterile or 1 male-fertile:1 male-sterile in the progeny of the selfed maintainer containing the EC-H1 or the REC-H1, respectively. During the propagation of the maintainer by self pollination, the proportion of the male-sterile plants in the selfed progeny increases with generations since male-sterile plants are obtained not only in the progeny of the male-fertile ones but also all the progeny of the male-sterile plants which are pollinated by the male-fertile sibs growing together in mixture, are male-sterile. Consequently, the proportion of the male-fertile plants (the maintainer) in the mixture decreases to a degree that the pollen load is insufficient to pollinate, in all the female production plots, all the male-sterile female flowers. It is very important therefore to keep constant, in each generation, the original ratio of male-sterile to male-fertile plants. This may be achieved by roguing, in each generation, the male-sterile plants from the selfed progeny of the maintainer. This step is laborious and increases the production cost of the female parent seeds. It is preferable therefore, to take advantage of the presence of the rht allele on the short arm of 4S$^s$ of the EC-H1 or the REC-H1. This allele which is permanently linked to the Ms-S$^s$1 allele, affects plant height in a way that plants carrying it (i.e., the maintainer) are taller (by 6–8 cm) than those lacking it (the male-sterile female plants). This height difference facilitates the selective harvest of the maintainer from the mixture.

Another preferable way to keep constant the original ratio of male-fertile to male-sterile plants in the progeny of the selfed maintainer is achieved by further improvement of the EC or the REC, which is based on the incorporation of a further selectable marker such as herbicide resistance, disease resistance or blue seed color, into any of these two engineered chromosomes of the maintainer. Incorporation of the chlorotoluron resistance allele Su-S$^s$1 in the EC (rendering it EC-HR) (FIG. 2b) or the REC (rendering it REC-HR) (FIG. 2d) facilitates the selective killing, in each generation, of the male-sterile plants only, by the herbicide. EC-HR is produced by the following steps (FIG. 8a): maintainer plants of the cultivar Chinese Spring (CS) which are homozygous for ms-B1, su-B1 and Ki-B1 and carrying EC-H are pollinated by a line of *Ae searsii* carrying Su-S$^s$1 and the F$_1$ is backcrossed as female to CS. Herbicide resistant plant are selected in the resultant progeny of the backcross and then selfed to yield BC$_1$F$_2$ progeny. The maintainer plants are selected from BC$_1$F$_2$ by chromosome counts (selection for 2n=43) and by chlorotoluron resistance. Similarly, incorporation of a disease resistance allele into the EC or the REC makes it possible to infect the field with a pathogen. Only the male-sterile plants are susceptible and produce fewer seeds that are shrivelled and are blown away by the combine harvester. Incorporation of a blue aleurone (Ba) allele from *Agropyron elongatum* or *Triticum monococcum* or any other Gramineae species into the EC or REC as a selectable marker constitutes a preferred embodiment of the invention to produce an improved engineered chromosome (IEC) or improved recombinant engineered chromosome (IREC), possibly containing the Ms-A$^m$1 allele from chromosome 4A$^m$ of *T. monococcum*, the Ba-E1 allele from chromosome 4E of *Agropyron elongatum* and the ki-B1-a allele from chromosome 6S$^l$ of *Ae. longissima*, thus facilitating growing a maintainer with 100% male-fertile plants. The Ba allele determines the color (due to; anthocyanine production) in the aleurone layer of the 3n endosperm. The expression of the Ba allele is dosage dependent: two doses of the Ba allele contributed by the female gamete to the 3n endosperm, determine a blue seed color that is distinct from the typical red/white color of wheat seeds. The seed color marker is permanently linked to the Ms allele and consequently distinguishes between blue seeds, when grown, developing into male-fertile plants (the maintainer) and red/white seeds, when grown, developing into male-sterile plants. The two types of seeds may be mechanically separated by means of a sorting apparatus.

The above modifications in the EC and REC are designated as IEC-HC (FIGS. 3a, 4a and 5a) and IREC-HC (FIGS. 3b, 4b and 5b) and are produced in the following manner: IEC-HC1 carrying the Ms-$S^s$1 and rht-$S^s$1 alleles from *Ae. searsii*, the Ba-E1 allele from *A. elongatum* and the ki-$S^l$1-a allele from *Ae. longissima*, is produced in two steps (FIGS. 9a–d): first, production of a translocated chromosome $4S^sS/4EL$ as a result of simultaneous centromeric mis-division of chromosomes $4S^s$ and 4EL followed by centric fusion of $4S^sS$ and 4EL that occurs in double monosomic addition $4S^s$ and 4E to common wheat; the second step involves irradiation with thermal neutrons of seeds of the double monosomic addition $4S^sS/4EL$ and $4S^sS/6S^lL$ and selection in the progeny of the desired translocation $4S^sS/4EL/6S^lL$.

IEC-HC2 carrying the Ms-$S^s$1 and rht-$S^s$1 alleles from *Ae. searsii*, the Ba-$A^m$1 allele from *T. monococcum* and the Ki-$S^l$1-a allele from *Ae. longissima*, is produced by the following steps (FIG. 10): first, production of a translocated chromosome $4S^sS/4A^mL$ due to simultaneous centromeric mis-division of chromosomes $4S^s$ and $4A^m$ followed by centric fusion of $4S^sS$ and $4A^mL$ that occurs in double monosomic addition $4S^s$ and $4A^m$ (or in monosomic addition $4S^s$ and monosomic translocated substitution 4BS/$4A^mL$) to common wheat; the second step involves irradiation of the double monosomic addition $4S^sS/4A^mL$ and $4S^sS/6S^lL$ and selection of the desired translocation $4S^sS/4A^mL/6S^lL$ in the progeny.

IEC-HC3 carrying the Ms-$A^m$1, rht-$A^m$1 and Ba-$A^m$1 alleles from *T. monococcum* and ki-$S^l$1-a from *Ae. longissima*, is produced by irradiation of the double monosomic addition $4A^m$ and $6S^l$ to common wheat and selection of the desired translocation among the progeny (FIG. 11). IEC-HC3 has the short arm and the proximal region of the long arm of chromosome 4 of *T. monococcum* ($4A^m$), carrying the Ms-$A^m$1 allele proved to confer male-fertility to an hexaploid genotype homozygous for ms-B1-c, the rht-$A^m$1 allele that is responsible for taller plants and the Ba-$A^m$1 allele that determines blue coloring of the aleurone, and the distal part of the long arm of chromosome 6 of *Ae. longissima* ($6S^lL$) carrying the recessive ki-$S^l$1-a allele.

The various RECs and IRECs (FIGS. 2b, 2d, 3b, 4b and 5b) are produced to increase the proportion (from 20% to 50%) of the maintainer male-fertile genotype in the selfed progeny of the selfed maintainer and to prevent occasional centric breakage of the engineered chromosome due to its centromeric misdivision. Production of these recombinant engineered chromosomes is achieved by induction, via induced homoeologous pairing, of a recombination between any one of EC-H1, EC-HR1, IEC-HC1, IEC-HC2 or IEC-HC3 and 6B, in which the distal segment of 6BL is translocated to the $6S^lL$ arm (the breakpoint is distal to the ki-$S^l$1-a allele) (FIGS. 7b and 12). This translocation enables the REC and the IRECs to pair, almost in every meiocyte, with 6BL in lines of common wheat homozygous for Ph1 and monosomics for 6B and REC or one of the IRECs, and segregate to opposite poles, resulting in the inclusion of the REC or the IREC in one half of the gametes.

Undesirable centric breakage of the engineered chromosome due to centromeric misdivision separates Ms-$S^s$1 and rht-$S^s$1 from ki-$S^l$1-a in EC-H1 and Ms-$S^s$1 and rht-$S^s$1 from Su-$S^s$1 and ki-$S^l$1-a in EC-HR1, facilitating the transmission of the Ms-$S^s$1 allele through the male gametes. This may result in some male-fertile offspring upon pollination of the male-sterile female line by the maintainer. These plants, carrying the rht allele, are taller than the male-sterile plants and can be rogued. Moreover, since centromeric misdivision occurs mainly in unpaired chromosomes (univalents), the use of REC or IREC which pair, in almost every meiocyte, with the native 6B, prevents such undesirable centric breakage.

The invention further provides a male-fertile maintainer line of common or durum wheat for the maintenance of a male-sterile female parental line for use in the production of hybrid wheat, and methods for the production thereof.

Yet another aspect of the present invention relates to the selection of seeds of the male-sterile female parent directly from the progeny of the selfed maintainer carrying either the IEC-HC (FIG. 15a) or the IREC-HC (FIG. 15b). About 80% of the seeds produced by the maintainer with the IEC-HC are not blue, lacking the IEC-HC and therefore, when grown, develop into male-sterile plants, and 20% are blue, carrying the IEC-HC and, when grown, develop into male-fertile plants. Sorting out the selfed seeds of the maintainer by means of a color-sorting apparatus will separate the seeds of the female parent (red/white) from those of the maintainer (blue). By this preferred method, seeds of the male-sterile female line are obtained directly from selfing of the maintainer line; no alternate planting of the maintainer and the female lines is required and the production cost of the female line is considerably reduced.

In another aspect, the invention provides methods for converting any desired cultivar of common or durum wheat into a male-sterile female parental line and a male-fertile maintainer line for said female line.

In still another aspect, the invention relates to a method for producing a hybrid plant line of common or durum wheat, wherein the male-sterile female parental line is crossed with any cultivar of the same species (R-line), which by its nature is male-fertile homozygous for the Ms-B1 allele, to yield $F_1$ hybrid progeny that are all fertile and heterozygous (Ms-B1ms-B1).

BRIEF DESCRIPTION OF THE DRAWINGS

FIG. 9d shows the interrelation among 9a, 9b and 9c.

FIGS. 13a–13b depict schemes according to FIG. 1a, for common or durum wheat, based on genic male-sterility, wherein the A-line is herein designated cv. 'One' which is homozygous for the recessive male-sterility allele ms-B1-c and for the dominant pollen-killer allele Ki-B1; (13a): the B-line of the same cv. 'One' is isogenic to the A-line but has also the engineered chromosome EC-H1 ($4S^sS$/$6S^lL$) carrying the dominant male-fertility allele Ms-$S^s$1 and the dominant rht allele on $4S^sS$ and the recessive pollen-killer allele ki-$S^l$1 on $6S^lL$, and the R-line is the herein designated cv. 'Two' which is homozygous for the wild-type male-fertility allele Ms-B1 and for one of the recessive pollen-killer alleles ki-B1-a or ki-B1-n; and (13b): same as (13a) but the B-line has the recombinant engineered chromosome REC-H1 instead of the EC-H1 and only one dose of the Ki-B1-carrying chromosome 6B.

FIGS. 14a–14b depict schemes according to FIG. 1a, for common or durum wheat, based on genic male-sterility, wherein the A-line is herein designated cv. 'One' which is homozygous for the recessive male-sterility allele ms-B1-c, for the recessive herbicide susceptibility allele su-B1 and for the dominant pollen-killer allele Ki-B1; (14a): the B-line of the same cv. 'One' is isogenic to the A-line but has also the engineered chromosome EC-HR1 ($4S^sS$/$6S^lL$) carrying the dominant male-fertility allele Ms-$S^s$1 and the dominant rht allele on $4S^sS$, the dominant Su-$S^s$1 allele and the recessive pollen-killer allele ki-$S^l$1 on $6S^lL$, and the R-line is the herein designated cv. 'Two' which is homozygous for the wild-type male-fertility allele Ms-B1 and for one of the recessive pollen-killer alleles ki-B1-a or ki-B1-n; and (14b): same as (14a) but the B-line has the recombinant engineered chromosome REC-HR1 instead of the EC-HR1 and only one dose of the Ki-B1-carrying chromosome 6B.

FIGS. 15a–15b depict alternative schemes according to FIGS. 1b and 1c, for common or durum wheat based on genic male-sterility, wherein the A-line herein designated cv, 'One', is homozygous for the recessive male-sterility allele ms-B1-c and the dominant pollen-killer allele Ki-B1; (15a): the B-line of the same cv. 'One' is isogeric to the A-line but has the improved engineered chromosome IEC-HC1 having $4S^sS$/4EL/$65^lL$, carrying the Ms-$S^s$1, rht-$S^s$1, Ba-E1, ki-$S^l$1-a alleles, and the R-line, herein designated cv. 'Two', is homozygous for the wild-type male-fertility allele Ms-B1 and for one of the recessive pollen-killer alleles ki-B1-a or ki-B1-n; and (15b): same as (15a) but the B line has the improved recombinant engineered chromosome IREC-HC1 instead of IEC-HC1 and only one dose of the Ki-B1 carried on chromosome 6B.

DETAILED DESCRIPTION OF THE INVENTION

Figure 1A:
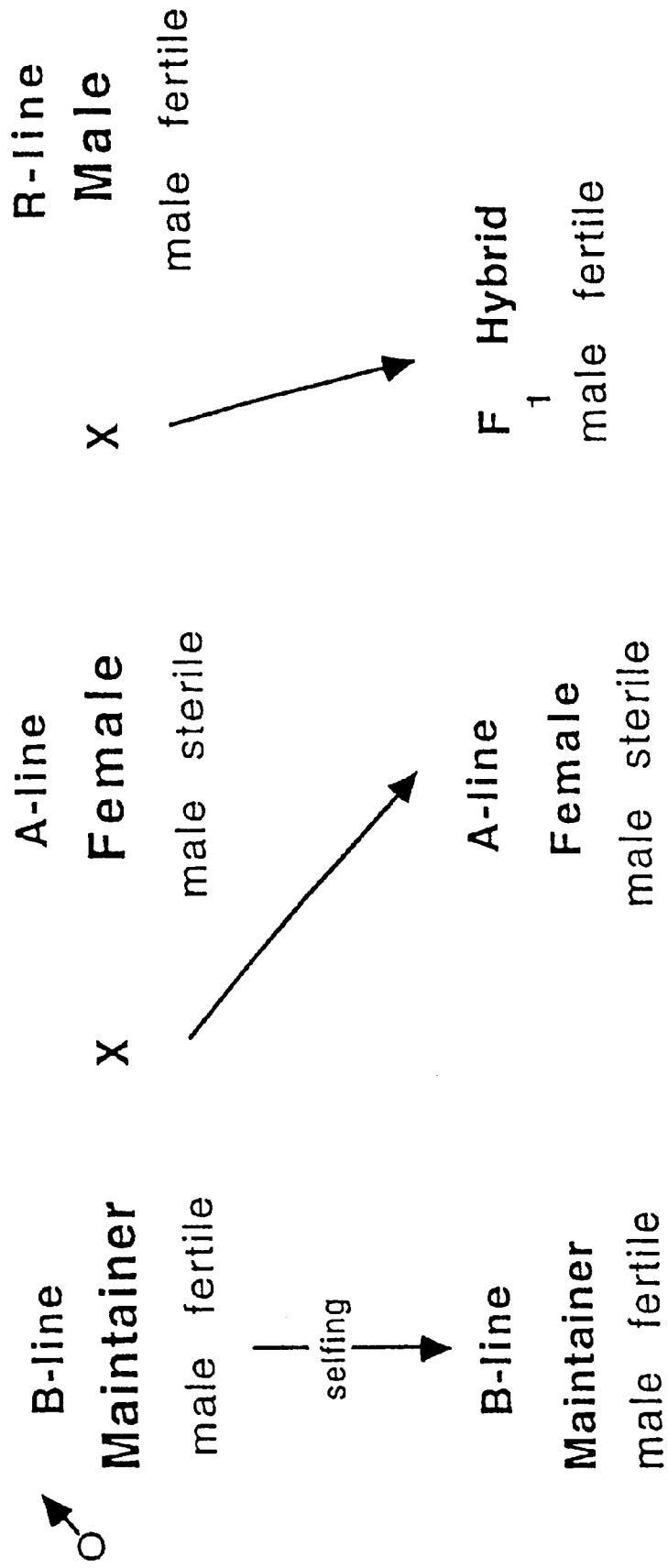
FIGS. 1a–1c depict general schemes for maintaining a male-sterile female parental line (A-line) by either (1a) pollinating it by a maintainer line (B-line); (1b) selecting it among the segregating progeny of a selfed maintainer line; or (1c) combining the methods described in 1a and 1b; and hybrid seed ($F_1$) production by pollinating the A line with a male line (R-line).
Figure 13A:
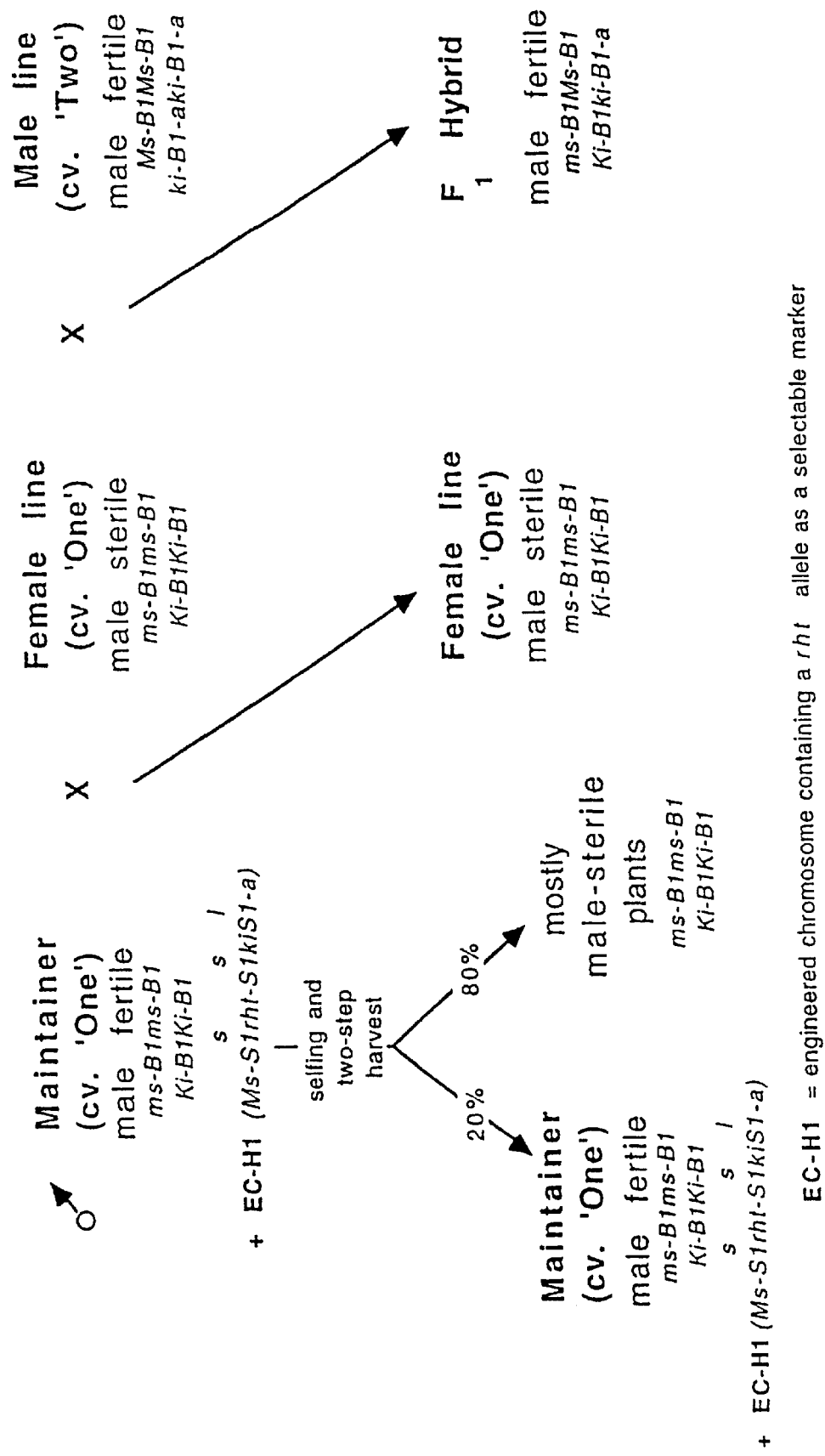
Figure 14A:
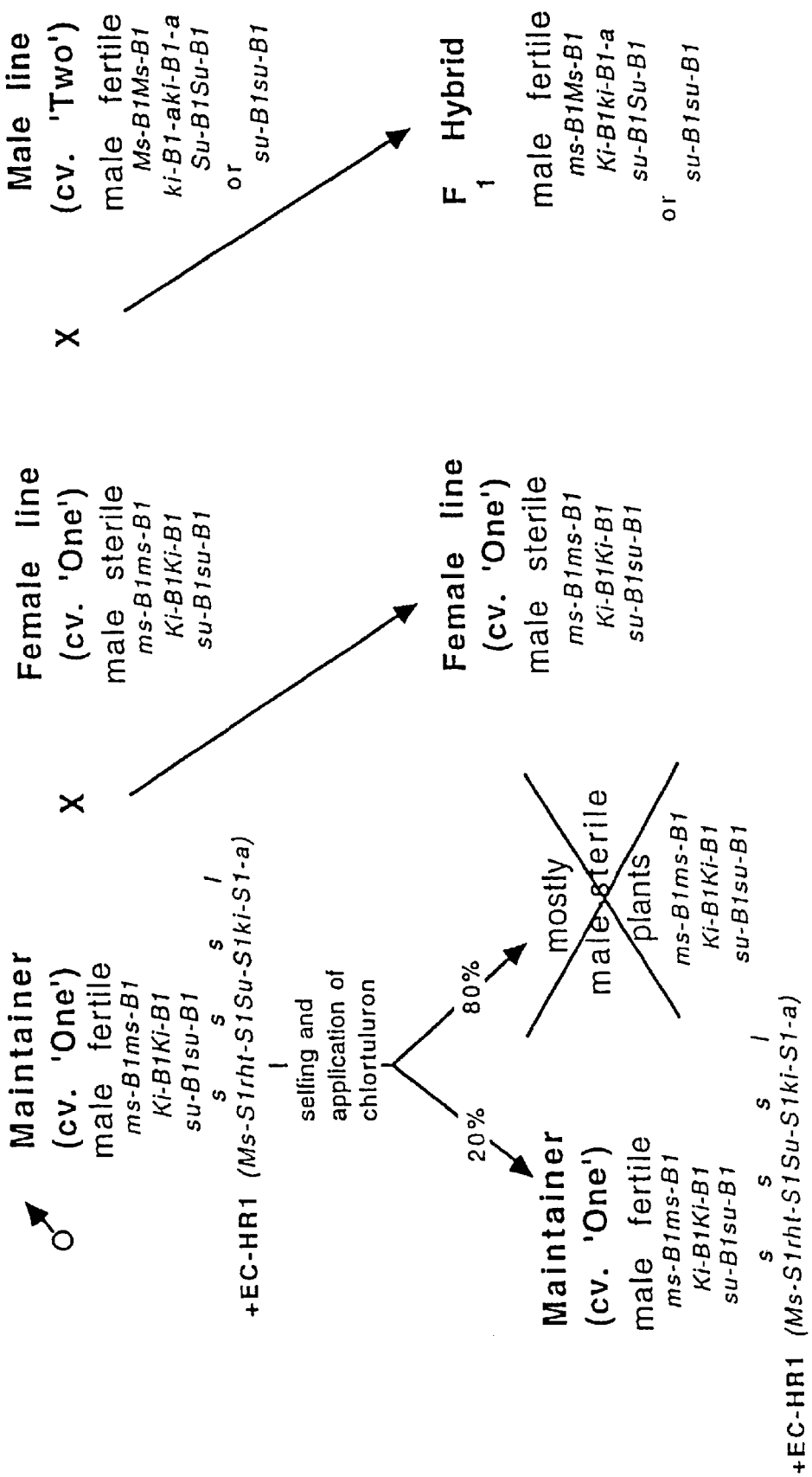

In accordance with the present invention a simple system has been developed for common or durum wheat as depicted in FIGS. 1a, 13a and 14a, by which the male-sterile female parental line (A-line) is maintained by pollinating it with the maintainer line (B-line), and all of the resulting progeny are male-sterile female plants. Similarly, the maintainer line is itself easily maintained by self-pollination, resulting in a mixture of seeds of which about 20%, when grown, develop into male-fertile plants identical to the maintainer line and carrying -the engineered chromosome, and about 80%, when grown, develop into male-sterile plants due to to the absence of the Ms-$S^s$1 allele. Utilizing the selectable markers to characterize the maintainer, the proportion of 80% male-sterile to 20% male-fertile plants is kept in each generation of the progeny of the selfed maintainer line.

Figure 1B:
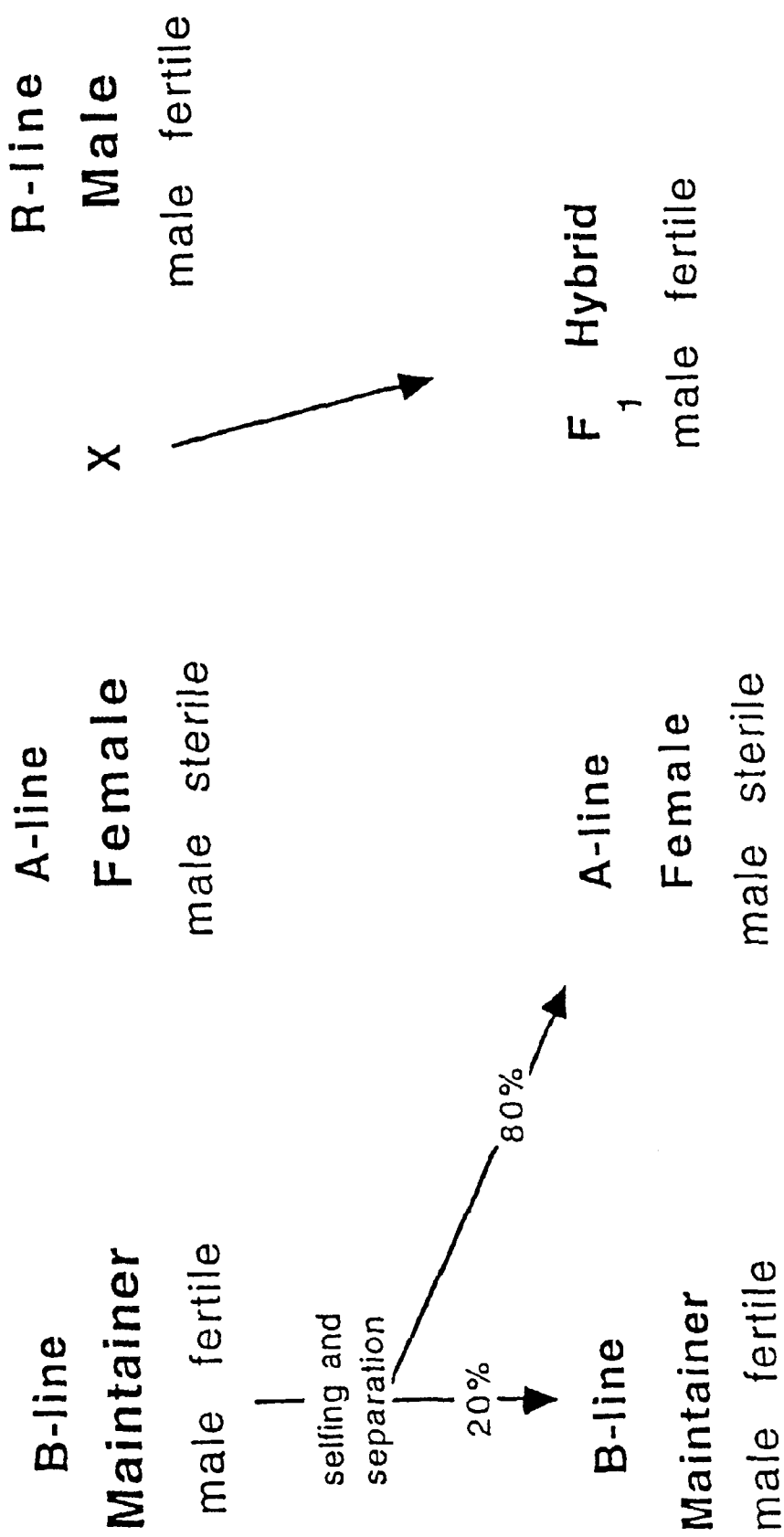

When the selectable marker is a color selectable marker such as blue aleurone or another seed characteristic, the present invention provides an alternative improved and preferred system for the maintenance of both the male-sterile female parental line (A-line) and the male-fertile maintainer line (B-line) (FIGS. 1b, c and 14a). Seeds of the two lines are obtained by self pollination of the maintainer: 80% of the seeds are red/white, and when grown, develop into male-sterile plants (A-line) and 20% are blue, and when grown, develop into male-fertile plants (B-line). Sorting out the seeds of the selfed maintainer by means of a color-sorting apparatus separates the two types of seeds. By this preferred method, seeds of the male-sterile female line are obtained directly from selfing of the maintainer line; no alternate planting of the maintainer and the female line is required and the production cost of seeds of the female parent is considerably reduced. Also, there is no decrease in the amount of the viable pollen in the maintainer plots since all the plants in the maintainer plots are male-fertile.

For hybrid wheat production, the male-sterile female parental line is crossed with any common or durum wheat cultivar (R-line), which by its nature is male-fertile homozygous for the Ms-B1 allele, to yield $F_1$ hybrid offspring that are all heterozygous Ms-B1ms-B1 and therefore, male-fertile.

Accordingly, in one aspect, the present invention provides a method for the maintenance of a male-sterile female parental line (FIGS. 13a, 14a and 15a) of common or durum wheat for use in the production of hybrid wheat, said method comprising:

(a) crossing a female parent with a male parent, said female parent being a male-sterile plant homozygous both for any one of the recessive ms-B1 male-sterility alleles on the short arm of chromosome 4B (4BS), and for the dominant pollen-killer Ki-B1 allele on the long arm of chromosome 6B (6BL), said male parent being the maintainer line and being isogenic to the female parent and homozygous for the same ms-B1 and Ki-B1 alleles of the female parent, and having an additional alien engineered chromosome selected from: (i) an engineered chromosome, herein referred to as EC, consisting of segments derived from two or more different alien chromosomes, carrying a dominant male-fertility allele Ms, a recessive allele ki which is susceptible to the killing action of the native pollen-killer allele on 6BL and one or two selectable markers by which plants having this chromosome can be selected; and (ii) an improved engineered chromosome, herein referred to as IEC, consisting of segments derived from two or more different alien chromosomes carrying, in addition to the Ms, ki and the selectable marker alleles, a seed marker by which seeds having this chromosome can be separated from seeds not having it; and (b) harvesting from the cross of (a) the progeny seed, all of which are homozygous for said male-sterility and pollen-killer alleles and lack the engineered chromosome EC or IEC, said seeds, when grown, developing into said male-sterile female line.

The present invention further provides an alternative method for maintaining a male-sterile female parental line (FIGS. 13b, 14b and 15b) of common or durum wheat for use in the production of hybrid wheat, said method comprising:

(a) crossing a female parent with a male parent, said female parent being a male-sterile plant homozygous both for any one of the recessive ms-B1 male-sterility alleles on the short arm of chromosome 4B (4BS), and for the dominant pollen-killer Ki-B1 allele on the long arm of chromosome 6B (6BL), said male parent being the maintainer line and being isogenic to the female parent and homozygous for the same ms-B1 allele of the female parent but monosomic both for chromosome 6B carrying the Ki-B1 allele and for a recombinant engineered chromosome selected from: (i) a recombinant engineered chromosome, herein referred to as REC, consisting of segments derived from two or more different alien chromosomes and from the distal segment of the native chromosome arm 6BL, carrying a Ms allele, a ki allele and one or two selectable markers by which plants having this chromosome can be selected; and (ii) an improved engineered chromosome, herein referred to as IREC, consisting of segments derived from two or more different alien chromosomes and from the distal segment of the native chromosome arm 6BL, carrying, in addition to the Ms, ki and the selectable marker alleles, a seed marker by which seeds having this chromosome can be separated from seeds not having it; and (b) harvesting from the cross of (a) the progeny seed, all of which are homozygous for said male-sterility and pollen-killer alleles and lack the recombinant engineered chromosome REC or IREC, said seeds, when grown, developing into said male-sterile female line.

The present invention also provides another alternative improved method for maintaining a male-sterile female parental line (FIG. 15a) of common or durum wheat for use in the production of $F_1$ hybrids of wheat, said method comprising:

(a) selfing an improved maintainer line which is isogenic to the female parent, i.e., homozygous both for any one of the recessive ms-B1 male-sterility alleles and for the dominant pollen-killer Ki-B1 allele, and having an additional improved engineered chromosome, herein designated IEC-HC (FIGS. 3a–5a), carrying in addition to Ms, rht and ki-S$^l$1-a alleles also the selectable seed marker Ba allele determining blue seed color, hence said improved engineered chromosome comprising either IEC-HC1 (4S$^s$S/4EL/6S$^l$L) carrying Ms-S$^s$1, rht-S$^s$1, Ba-E1 and ki-S$^l$1-a, IEC-HC2 (4S$^s$S/4A$^m$L/6S$^l$L) carrying Ms-S$^s$1, rht-S$^s$1, Ba-A$^m$1 and ki-S$^l$1-a or IEC-HC3 (4A$^m$S-4A$^m$L/6S$^l$L) carrying Ms-A$^m$1, rht-A$^m$1, Ba-A$^m$1 and ki-S$^l$1-a; and (b) harvesting from the selfed plants of (a) the progeny seed, all of which are homozygous for said male-sterility and pollen-killer alleles, 80% of which lack the IEC-HC and therefore are red/white and can be separated from the blue seeds containing the improved engineered chromosome by a sorting apparatus, said red/white seeds, when grown, developing into said male-sterile female line.

The present invention also provides another alternative improved method for maintaining a male-sterile female parental line (FIG. 15b) of common or durum wheat for use in the production of $F_1$ hybrids of wheat, said method comprising:

(a) selfing an improved recombinant maintainer line which is isogenic to the female parent, i.e., homozygous for any one of the recessive ms-B1 male-sterility alleles, but monosomic both for chromosome 6B carrying Ki-B1 allele and for the improved recombinant engineered chromosome of the IREC-HC type (FIGS. 3b, 4b, 5b) which further comprises, distally to the ki-S$^l$1-a allele, the distal region of the long arm of chromosome 6B (6BL) that pairs regularly with its homologous region of the native 6BL, said IREC-HC carrying in addition to Ms, rht and ki-S$^l$1-a alleles also the selectable seed marker Ba allele determining blue seed color, hence said improved recombinant engineered chromosome comprising either IREC-HC1 (4S$^s$S/4EL/6S$^l$L/6BL) carrying Ms-S$^s$1, rht-S$^s$1, Ba-E1 and ki-S$^l$1-a, IREC-HC2 (4S$^s$S/4A$^m$L/6S$^l$L/6BL) carrying Ms-S$^s$1, rht-S$^s$1, Ba-A$^m$1 and ki-S$^l$1-a, or IREC-HC3 (4A$^m$S-4A$^m$L/6S$^l$L/6BL) carrying Ms-A$^m$1, rht-A$^m$1, Ba-A$^m$1 and ki-S$^l$1-a;

(b) harvesting from the selfed plants of (a) the progeny seed, all of which are homozygous for said male-sterility allele, 50% of which are disomic for chromosome 6B and lack the IREC-HC and therefore are red/white, and when grown, develop into male-sterile plants, and the remainder 50% are monosomic for chromosome 6B and monosomic for the IREC-HC and therefore are blue, and when grown, develop into male-fertile plants, and growing said progeny seed of (a) for another generation in which the male-fertile plants will be selfed and also pollinate the male-sterile plants; and (c) harvesting from the plants of (b) the progeny seed, all of which are homozygous for the said male-sterility allele, about 75% of which are disomic for chromosome 6B and lack the IREC-HC and therefore are red/white and can be separated from the blue seeds containing the IREC-HC by a sorting apparatus, said red/white seeds, when grown, developing into male-sterile female line.

Any male-sterility ms-B1 allele may be used according to the invention such as, for example, the ms-B1-a, ms-B1-b and ms-B1-c alleles or any other allele of this locus or another locus of common or durum wheat inducing male sterility. Any Ba allele of one of the species of the Gramineae may be used according to the invention such as, for example, the Ba-A$^m$1 of *T. monococcum*, the Ba-E1 of *A. elongatum*, the Ba-R1 of rye and the Ba-H1 of barley. Any allele affecting seed characteristics may be used according to the invention. Any rht allele of one of the species of the Gramineae may be used according to the invention, such as rht-S$^s$1 of *Ae. searsii*, rht-S$^l$1 of *Ae. longissima* and rht-A$^m$1 of *T. monococcum*. Any herbicide resistance allele of one of the species of the Gramineae may be used according to the invention, such as Su-S$^s$1 of *Ae. searsii* or Su-S$^l$1 of *Ae. longissima*. Any ki allele of one of the species of the Gramineae, susceptible to the killing effect of Ki-B1 or any other pollen-killer gene may be used according to the invention.

In another aspect, the present invention provides a male-fertile maintainer line of common or durum wheat for the maintenance of a male-sterile female parental line for use in the production of hybrid wheat, said maintainer line being isogenic to the female parent and homozygous both for any one of the ms-B1 male-sterility alleles and for the pollen-killer Ki-B1 allele of the female parent, and having an additional alien engineered chromosome EC-H1 (4S$^s$S/6S$^l$L) carrying the Ms-S$^s$1, rht-S$^s$1 and ki-S$^l$1-a alleles. Since the male-fertility allele of the maintainer line is not transmitted through the pollen-grains, all of the offspring of a cross between the male-sterile female line and the male-fertile maintainer line are isogenic to the female parent and are male-sterile.

The present invention also provides a male-fertile maintainer line of common or durum wheat for the maintenance of a male-sterile female parental line for use in the production of hybrid wheat, said maintainer line being isogenic to the female parent and homozygous both for any one of the ms-B1 male-sterility alleles, for the su-B1 chlorotoluron susceptibility allele and for the pollen-killer Ki-B1 allele of the female parent, and having an additional alien engineered chromosome EC-HR1 (4S$^s$S/6S$^l$L) carrying the Ms-S$^s$1, rht-S$^s$1, Su-S$^s$1 and ki-S$^l$1-a alleles. Since the male-fertility allele of the maintainer line is not transmitted through the pollen-grains, all of the offspring of a cross between the male-sterile female line and the male-fertile maintainer line are isogenic to the female parent and are male-sterile.

The present invention further provides an alternative recombinant male-fertile maintainer line of common or durum wheat for maintaining a male-sterile female parental line for use in the production of hybrid wheat, said maintainer line being isogenic to the female line and homozygous for any one of the ms-B1 alleles, but is monosomic for chromosome 6B and therefore hemizygous for the Ki-B1 allele, and having an additional recombinant engineered chromosome REC-H1 (4S$^s$S/6S$^l$L/6BL), which further comprises, distally to the ki-S$^l$1-a allele, the distal region of 6BL that pairs regularly with its homologous region of the native 6BL. Consequently, the REC will be included in 50% of the gametes. Since the male-fertility allele of the recombinant maintainer line is not transmitted through the pollen-grains, all of the offspring of a cross between the male-sterile female line and the recombinant male-fertile maintainer line are isogenic to the female parent and are male-sterile. On the other hand, 50% of the progeny of the selfed recombinant maintainer will have the REC and therefore be male-fertile.

The present invention also provides an alternative recombinant male-fertile maintainer line of common or durum wheat for maintaining a male-sterile female parental line for use in the production of hybrid wheat, said maintainer line being isogenic to the female line and homozygous for any one of the ms-B1 and for the su-B1 alleles, but is monosomic for chromosome 6B and therefore hemizygous for the Ki-B1 allele, and having an additional recombinant engineered chromosome REC-HR1 (4S$^s$S/6S$^l$L/6BL), which further comprises, distally to the ki-S$^l$1-a allele, the distal region of 6BL that pairs regularly with its homologous region of the native 6BL. Consequently, the REC-HR1 will be included in 50% of the gametes. Since the male-fertility allele of the recombinant maintainer line is not transmitted through the pollen-grains, all of the offspring of a cross between the male-sterile female line and the recombinant male-fertile maintainer line are isogenic to the female parent and are male-sterile. On the other hand, 50% of the progeny of the selfed recombinant maintainer will have the REC-HR1 and therefore be male-fertile.

The present invention also provides an alternative improved maintainer line of common or durum wheat for the maintenance of a male-sterile female parental line for use in the production of hybrid wheat, said maintainer line being isogenic to the female parent and homozygous both for any one of the ms-B1 male-sterility alleles and for the pollen-killer Ki-B1 allele of the female parent, and having an additional improved engineered chromosome IEC-HC, either IEC-HC1 (4S$^s$S/4EL/6S$^l$L), IEC-HC2 (4S$^s$S/4A$^m$L/6S$^l$L) or IEC-HC3 (4A$^m$S-4A$^m$L/6S$^l$L) carrying the Ms-S$^s$1, rht-S$^s$1, Ba-E1 and the ki-S$^l$1-a, the Ms-S$^s$1, rht-S$^s$1, Ba-A$^m$1 and the ki-S$^l$1-a, and the Ms-A$^m$1, rht-A$^m$1, Ba-A$^m$1 and the ki-S$^l$1-a alleles, respectively. Any selectable marker allele can replace the Ba allele in the IEC-HC. When the selectable marker is a seed characteristic, such as seed color, progeny seed of the selfed maintainer developing into plants which are isogenic to the female parent and are male-sterile can be separated from those developing into the male-fertile maintainer line. Thus it is possible to maintain the male-sterile female parent by selfing the improved maintainer having such seed-selectable marker; 80% of the progeny seed of the selfed improved maintainer line are red/white, and when grown, develop into male-sterile female parent plants, and 20% are blue, and when grown, develop into the male-fertile improved maintainer plants.

The present invention also provides an alternative improved recombinant maintainer line of common or durum wheat for maintaining a male-sterile female parental line for use in the production of hybrid wheat, said maintainer line being isogenic to the female line and homozygous for any one of the ms-B1 alleles, but is monosomic for chromosome 6B and therefore hemizygous for Ki-B1 allele, and has an additional improved recombinant engineered chromosome IREC-HC, either IREC-HC1 (4S$^s$S/4EL/6S$^l$L/6BL), IREC-HC2 (4S$^s$S/4A$^m$L/6S$^l$L/6BL) or IREC-HC3 (4A$^m$S-4A$^m$L/6S$^l$L/6BL) carrying the Ms-S$^s$1, rht-S$^s$1, Ba-E1 and the ki-S$^l$1-a, the Ms-S$^s$1, rht-S$^s$1, Ba-A$^m$1 and the ki-S$^l$1-a, and the Ms-A$^m$1, rht-A$^m$1, Ba-A$^m$1 and the ki-S$^l$1-a alleles, respectively, and all having the distal segment of 6BL of common wheat. Any selectable marker allele can replace the Ba allele in the IREC-HC.

Figure 7A:
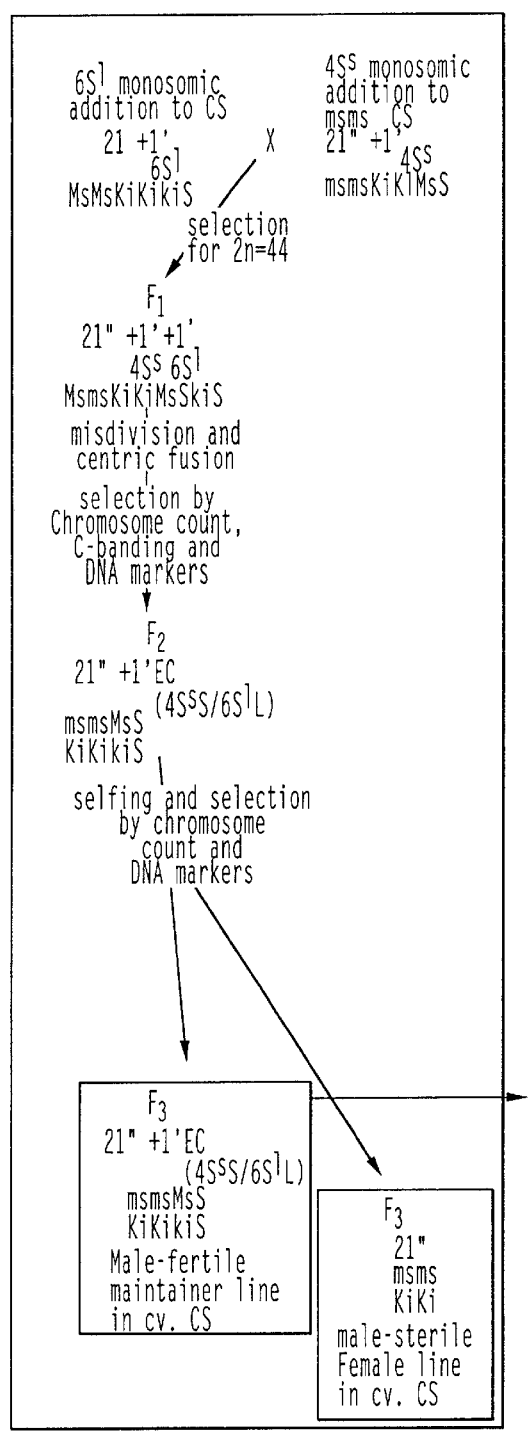
FIGS. 7a–7b depict schematic procedures for producing the maintainer line with the engineered chromosome EC-H1 (7a) and the recombinant engineered chromosome REC-H1 (7b), carrying Ms-$S^s$1 and rht-$S^s$1 from $4S^sS$ of *Ae. searsii* and ki-$S^l$1-a from $6S^lL$ of *Ae. longissima*, as well as the male-sterile female line in the common wheat cultivar Chinese Spring. EC-H1 is produced as a monosomic addition in disomic 6B plants and therefore also homozygous for Ki-B1; REC-H1 is produced as a monosomic substitution in monosomic-6B plants and therefore hemizygous for Ki-B1.

In another aspect of the present invention, there is provided a method for producing a male-fertile maintainer line of common or durum wheat having the engineered chromosome EC-H1 (FIG. 7a), comprising:

(a) crossing a male-fertile female parent derived from the common wheat cultivar Chinese Spring, said female parent being homozygous for both the dominant Ms-B1 male-fertility allele on chromosome arm 4BS, and the dominant Ki-B1 pollen-killer allele on 6BL, and having an additional alien chromosome 6S$^l$ carrying on its long arm the recessive pollen-killer allele ki-S$^l$1-a, with a male parent that is isogenic to the female parent but is homozygous for the recessive ms-B1-c male-sterility allele and also lacks chromosome 6S$^l$ and has instead, an additional alien chromosome 4S$^s$, carrying on its short arm the dominant alleles Ms-S$^s$1 and rht-S$^s$1;

(b) collecting the progeny seed of the cross of (a) and growing said seeds, thus producing male-fertile F$_1$ plants, some of which are double monosomic addition, i.e., they have the two alien chromosomes 4S$^s$ carrying Ms-S$^s$1 and rht-S$^s$1 and 6S$^l$ carrying ki-S$^l$1-a;

(c) selfing said F$_1$ progeny of (b), collecting a large number of the progeny seed thereof and growing said seeds, thus producing F$_2$ plants, some of which are monosomic addition for an alien translocated engineered chromosome, 25% of which are homozygous for the ms-B1-c male sterility allele and are the desired plants;

(d) selecting said desired plants of (c) by chromosome count, C-banding and use of DNA markers and selfing them;

(e) collecting the selfed progeny seed of (d) and growing said seeds, thus producing F$_3$ plants, all of which are homozygous for the ms-B1-c male-sterility allele, 20% of which are male-fertile because they have also said additional engineered chromosome EC-H1, these being the desired maintainer line plants; and (f) selecting the desired maintainer line plants of (e) by chromosome count and use of DNA markers.

Figure 8A:
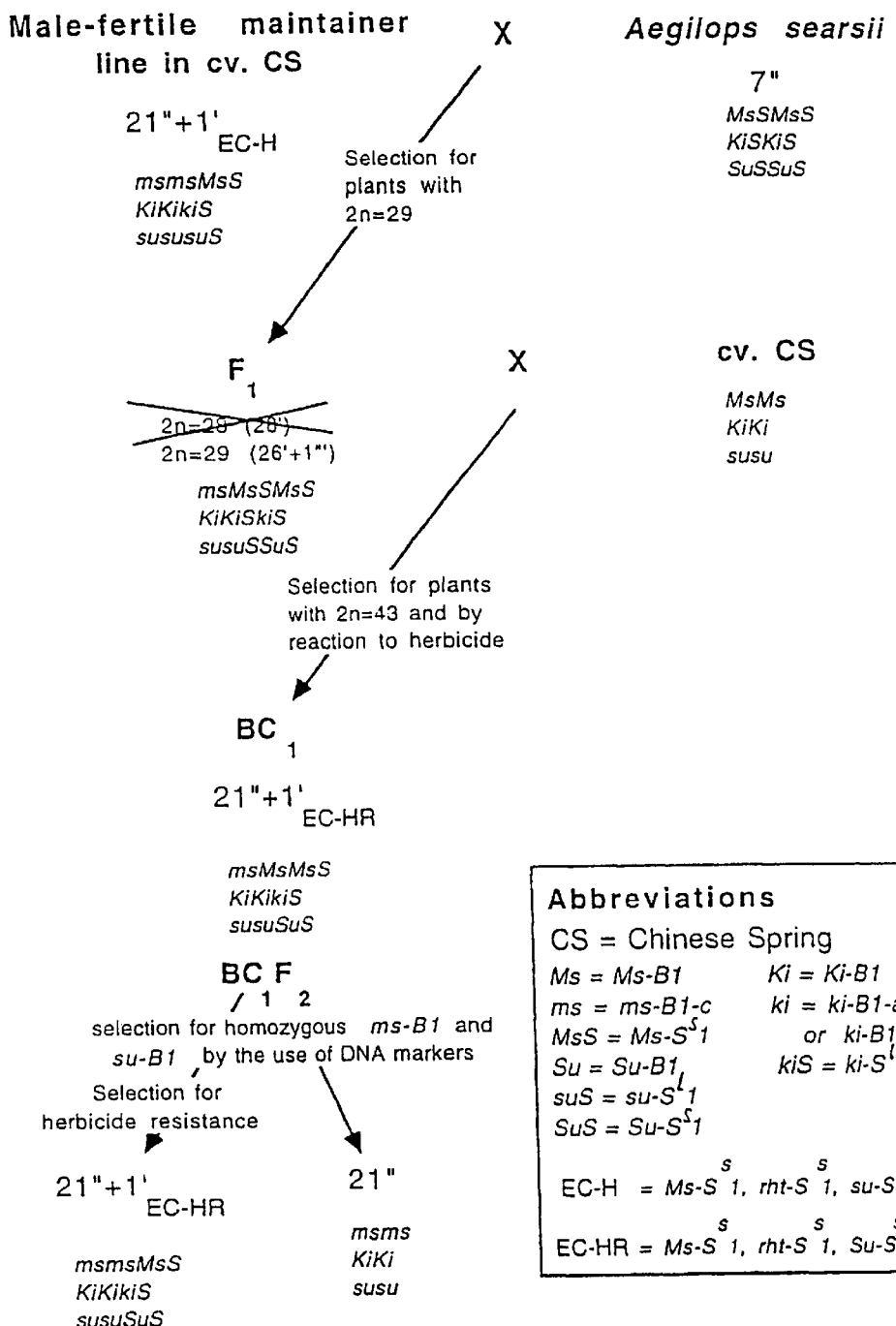
FIGS. 8a–8b depict schematic procedures for producing the maintainer line with the engineered chromosome EC-HR1 (8a) and the recombinant engineered chromosome REC-HR1 (8b), carrying Ms-$S^s$1 and rht-$S^s$1 from $4S^sS$ of Ae. searsii, Su-$S^s$1 from $6S^sL$ of Ae. searsii, and ki-$S^l$1-a from $6S^lL$ of Ae. longissima. EC-HR1 is produced as a monosomic addition in disomic 6B plants and therefore also homozygous for Ki-B1; REC-HR1 is produced as a monosomic substitution in monosomic-6B plants and therefore hemizygous for Ki-B1.

The present invention also provides a method for producing a male-fertile maintainer line of common or durum wheat having the engineered chromosome EC-HR1 (FIG. 8a), comprising:

(a) crossing a male-fertile female parent derived from the male-fertile maintainer line in the common wheat cultivar Chinese Spring, said female parent being homozygous for both the recessive ms-B1 male-sterility allele, the recessive chlorotoluron susceptibility allele su-B1 and the dominant Ki-B1 pollen-killer allele, and having, as a monosomic addition, the engineered chromosome EC-H1 carrying on its short arm the dominant male-fertility allele Ms-S$^s$1 and the semi-dominant rht-S$^s$1 allele and on its long arm the recessive chlorotoluron susceptibility allele su-S$^l$1 and the recessive pollen-killer allele ki-S$^l$1-a, with the line of the diploid species Aegilops searsii that possesses the dominant chlorotoluron resistance allele Su-S$^s$1 on 6S$^s$L as well as the Ms-S$^s$1 and rht-S$^s$1 alleles on 4S$^s$S;

(b) collecting the progeny seed of the cross of (a) and growing said seeds, thus producing F$_1$ plants, some of which have 2n=29 chromosomes, i.e., they have one chromosome set from CS, the engineered chromosome EC-H1 and a chromosome set from Aegilops searsii, having the genotype ms-B1Ms-S$^s$1Ms-S$^s$1, ki-B1ki-S$^l$1-a and su-B1su-S$^l$1Su-S$^s$1;

(c) selecting said F$_1$ progeny of (b) with 2n=29 chromosomes and backcrossing them to cv. CS as a male, collecting the progeny seed thereof and growing said seeds, thus producing BC$_1$ plants, some of which that are resistant to chlorotoluron are monosomic addition for the engineered chromosome EC-HR1, all of which are heterozygous ms-B1Ms-B1 and homozygous for su-B1 and Ki-B1 and are the desired plants;

(d) selecting said desired plants of (c) by chromosome count and use of DNA markers and selfing them;

(e) collecting the selfed progeny seed of (d) and growing said seeds, thus producing BC$_1$F$_2$ plants, 20% of which are resistant to chlorotoluron, i.e., carry the engineered chromosome, 25% of the resistant plants are homozygous for ms-B1 but are male-fertile because they carry the Ms-S$^s$1 of the engineered chromosome EC-HR1, these being the desired maintainer line plants; and (f) selecting the desired maintainer line plants of (e) by their chlorotoluron resistance and use of DNA markers.

Figure 7B:
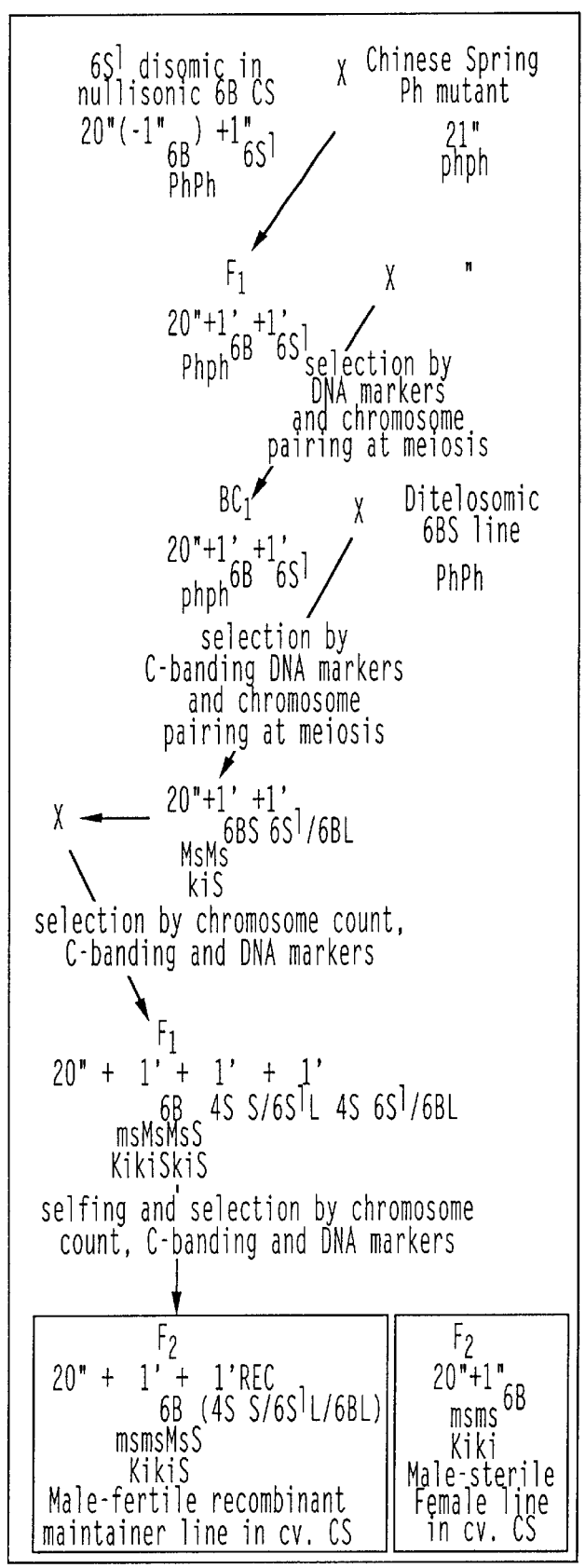

The present invention further provides a method for producing a male-fertile recombinant maintainer line of common or durum wheat having the recombinant engineered chromosome REC-H1 (FIG. 7b), comprising:

(a) crossing a male-fertile female parent derived from the common wheat cultivar Chinese Spring, said female parent being homozygous for the dominant Ms-B1 male-fertility allele on chromosome arm 4BS and for the dominant homoeologous-pairing suppressor allele Ph1l on chromosome arm 5BL, nullisomic for chromosome 6B and therefore deficient for the dominant Ki-B1 pollen-killer allele, and having a pair of 6S$^l$ chromosomes carrying the recessive pollen-killer allele ki-S$^l$1-a, with a male parent that is isogenic to the female parent but is disomic 6B and therefore homozygous for Ki-B1, lacks chromosome 6S$^l$, and is also homozygous for the mutant homoeologous-pairing allele ph1b;

(b) collecting the progeny seed of the cross of (a) and growing said seeds, thus producing male-fertile (Ms-B1Ms-B1) F$_1$ plants heterozygous for the homoeologous-pairing alleles (Ph1ph1b), all of which are monosomic for both 6B and 6S$^l$ chromosomes;

(c) backcrossing said F$_1$ plants of (b) to the male parent;

(d) collecting the progeny seed of the cross of (c) and growing said seeds, thus producing BC$_1$ plants, all of which are male-fertile (Ms-B1Ms-B1), 50% of which are homozygous for the ph1b allele, of which about 50% (because 6B pairs with 6S$^I$) are double monosomic for both 6B and 6S$^I$ chromosomes and are the desired BC$_1$ plants;

(e) selecting the desired BC$_1$ plants of (d) by using DNA markers and analysis of chromosome pairing at meiosis, and pollinating them by a ditelosomic 6BS line (i.e. deficient for 6BL arms) which is isogenic to the BC$_1$ plants but is homozygous Ph1Ph1;

(f) collecting the progeny seed of the cross of (e) and growing said seeds, thus producing plants, all of which are monotelosomic for chromosome arm 6BS, some of which are also monosomic for a recombinant chromosome consisting of the short arm and the proximal region of the long arm of 6S$^I$ (carrying ki-S$^I$1-a) and the distal region of chromosome arm 6BL (the recombination point is distal to ki-S$^I$1-a) and are the desired plants;

(g) selecting said desired plants of (f) by C-banding, use of DNA markers and analysis of chromosome pairing and crossing them as males with a female line which is the non-recombinant maintainer line, i.e., homozygous for both any one of the recessive male-sterility allele ms-B1 and the dominant pollen-killer allele Ki-B1 and has the engineered chromosome EC-H1 carrying Ms-S$^s$1, rht-S$^s$1 and ki-S$^I$1-a;

(h) collecting the progeny seed of the cross of (g) and growing said seeds, thus producing F$_1$ plants, some of which are triple monosomics, i.e., monosomnic for 6B, for the alien engineered chromosome EC-H1 and for the recombinant chromosome (6S$^I$/6BL) and are heterozygous Ms-B1ms-B1, hemizygous Ki-B1 and homozygous ki-S$^I$1-aki-S$^I$1-a and are the desired plants; and (i) selecting said desired plants of (h) by chromosome count, C-banding and by the use of DNA markers and selfing them, collecting the progeny seed thereof and growing said seeds, thus producing F$_2$ plants, some of which are double monosomics, having chromosome 6B and the recombinant engineered chromosome REC-H1 (4S$^s$S/6S$^I$L/6BL), carrying Ms-S$^s$1, rht-S$^s$1 and ki-S$^I$1-a, these being the desired maintainer line plants.

Figure 8B:
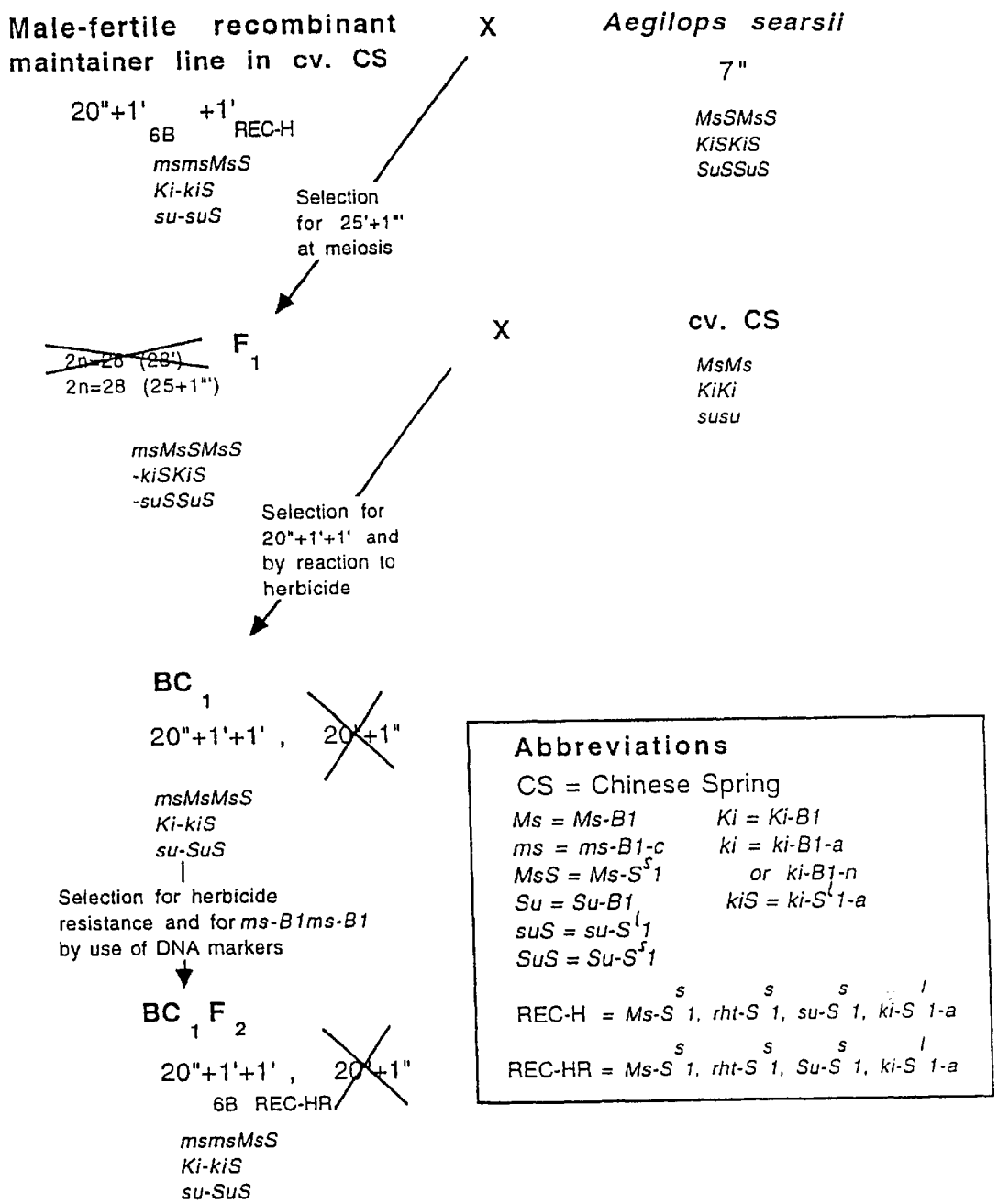

The present invention also provides a method for producing a male-fertile recombinant maintainer line of common or durum wheat having the recombinant engineered chromosome REC-HR1 (FIG. 8b), comprising:

(a) crossing a male-fertile female parent derived from the male-fertile recombinant maintainer line in the common wheat cultivar Chinese Spring, which is monosomic 6B monosomic addition REC-H1, said female parent being homozygous for the recessive ms-B1 male-sterility allele on chromosome arm 4BS and hemizygous for the recessive chlorotoluron susceptibility allele su-B1 and the dominant Ki-B1 pollen-killer allele, and having, as a monosomic substitution, the engineered chromosome REC-H1 (4S$^s$S/6S$^I$L/6BL) carrying on its short arm the dominant male-fertility allele Ms-S$^s$1 and the semi-dominant rht-S$^s$1 allele and on its long arm the recessive chlorotoluron susceptibility allele su-S$^I$1 and the recessive pollen-killer allele ki-S$^I$1-a, with the line of the diploid species *Aegilops searsii* that possesses the dominant chlorotoluron resistance allele Su-S$^s$1 as well as the Ms-S$^s$1 and rht-S$^s$1 alleles;

(b) collecting the progeny seed of the cross of (a) and growing said seeds, thus producing F$_1$ plants, 50% of which contain the recombinant engineered chromosome that pairs with 4S$^s$S and 6S$^s$S thus forms a trivalent at meiosis, having the genotype ms-B1Ms-S$^s$1Ms-S$^s$1, ki-S$^I$1-a su-S$^I$1 and Su-S$^s$1;

(c) selecting said F$_1$ progeny of (b) and backcrossing them to cv. Chinese Spring as a male;

(d) collecting the progeny seed thereof and growing said seeds, thus producing BC$_1$ plants, all of which are heterozygous ms-B1Ms-B1 and therefore male-fertile, some of which are monosomic 6B and therefore hemizygous for su-B1 and Ki-B1 and having the recombinant engineered chromosome REC-HR1 as monosomic substitution carrying Ms-S$^s$1 and rht-S$^s$1 on the short arm and Su-S$^s$1 and ki-S$^I$1-a on the long arm and are the desired plants;

(e) selecting said desired plants of (c) by their resistance to chlorotoluron and by the analysis of chromosome pairing at meiosis and selfing them;

(f) collecting the selfed progeny seed of (d) and growing said seeds, thus producing BC$^1$F$_2$ plants, 50% of which are monosomic 6B and monosomic for the recombinant chromosome REC-HR1 consisting of the short arm of 4S$^s$ (carrying Ms-S$^s$1 and rht-S$^s$1), the proximal region of the long arm of 6S$^I$ (carrying Su-S$^s$1 and ki-S$^I$1-a) and the distal region of chromosome arm 6BL (the recombination point is distal to ki-S$^I$1-a), 25% of these plants are homozygous for ms-B1 and hemizygous for su-B1 and Ki-B1 these being the desired maintainer line plants; and (g) selecting the desired recombinant maintainer line plants of (e) by chlorotoluron resistance, use of DNA markers and analysis of chromosome pairing.

Figure 9A:
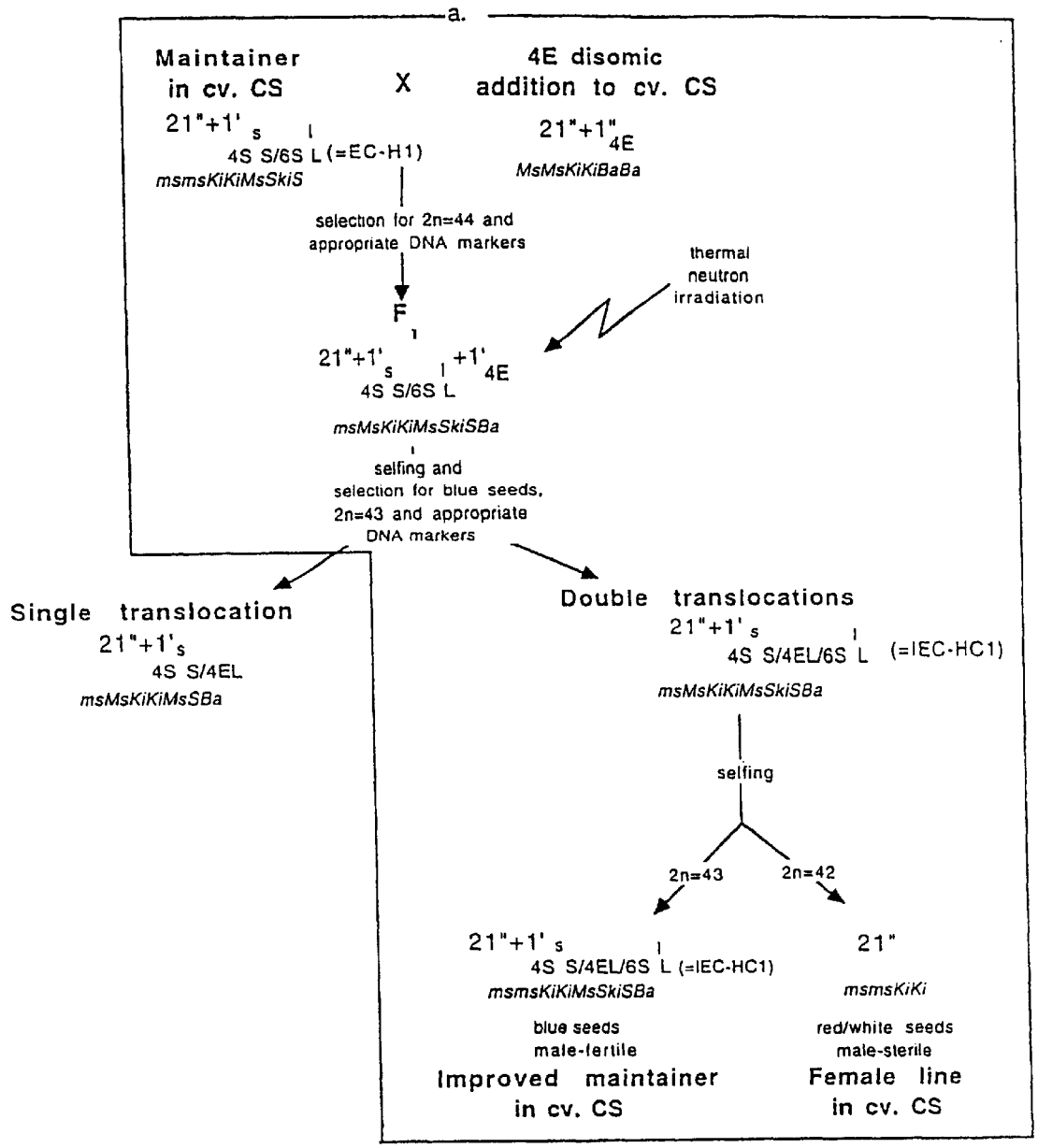
FIGS. 9a–9d depict three schematic procedures for producing the maintainer line with the improved engineered chromosome IEC-HC1 carrying Ms-$S^s$1 and rht-$S^s$1 from $4S^sS$ of Ae. searsii, Ba-E1 from 4EL of A. elongatum and ki-$S^l$1-a from $6S^lL$ of Ae. longissima, as well as the male-sterile female line in the common wheat cultivar Chinese Spring. The double breakage and reunion is induced in double monosomic addition for the EC-H1 and 4E chromosome (9a); single breakage and reunion is induced between the EC-H1 and an already irradiation-translocated chromosome $4S^sS$/4EL (9b); single breakage and reunion is induced between the EC-H1 and the translocated chromosome $4S^sS$/4EL obtained by mis-division and centric fusion (9c)
Figure 9B:
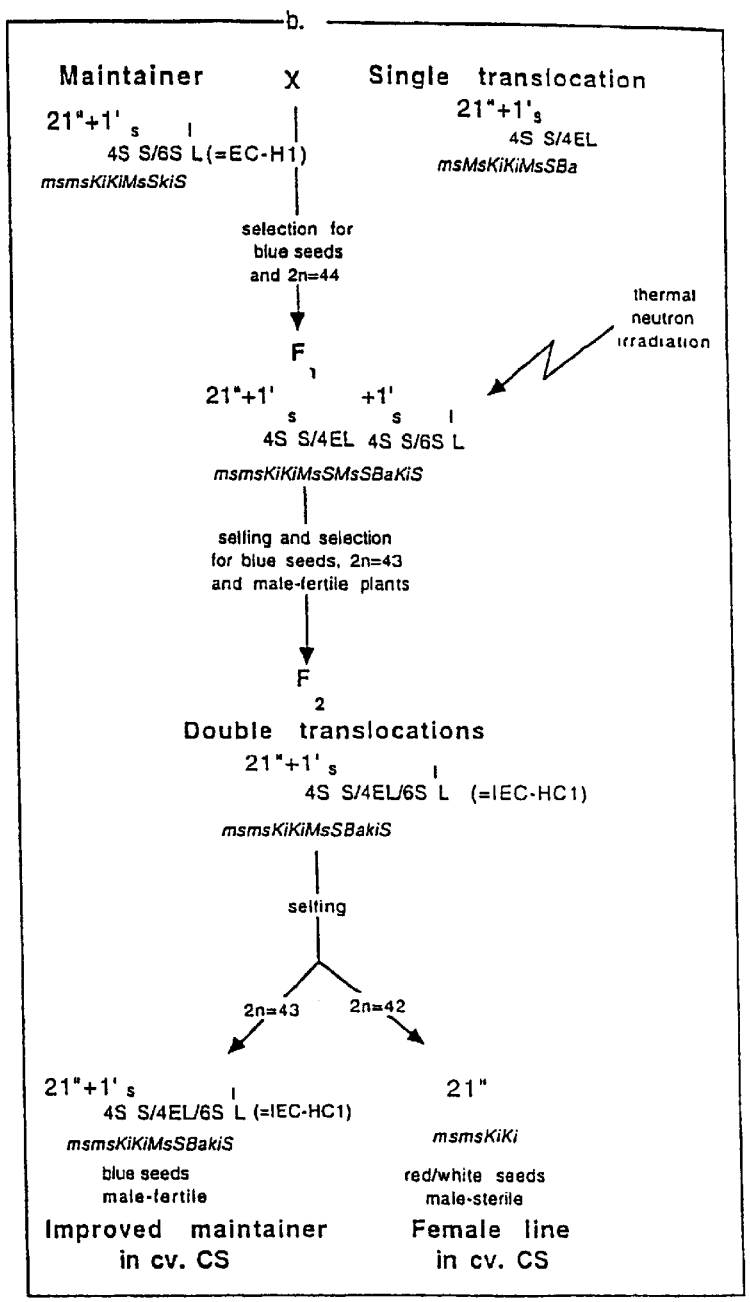

The present invention further provides a method for producing a male-fertile improved maintainer line of common or durum wheat having the improved engineered chromosome IEC-HC1 (FIGS. 9a–b), comprising:

(a) crossing a male-fertile female parent derived from the common wheat cultivar Chinese Spring, said female parent being the maintainer line, i.e., homozygous for both the recessive ms-B1 male-sterility allele on chromosome arm 4BS, and the dominant Ki-B1 pollen-killer allele on 6BL, and having an additional engineered chromosome EC-H1 carrying on its short arm the dominant alleles Ms-S$^s$1 and rht-S$^s$1 and on its long arm the recessive allele ki-S$^I$1-a, with a male parent that is isogenic to the female parent but is homozygous for the dominant male-fertility allele Ms-B1 and has an additional pair of the alien chromosomes 4E carrying on its long arm the dominant blue aleurone allele Ba-E1;

(b) collecting the progeny seed of the cross of (a) all of which are blue, irradiating them by thermal neutrons, and growing said seeds, thus producing male-fertile F$_1$ plants, all being heterozygous MsB1ms-B1 and homozygous for Ki-B1, 20% of which are double monosomic addition for the engineered chromosome EC-H1 and for chromosome 4E and are the desired plants;

(c) selecting said desired F$_1$ plants of (b) by chromosome count and by using DNA markers and selfing them;

(d) collecting the progeny seeds of (c), selecting the blue seeds and growing said seeds, thus producing F$_2$ plants, some of which have 43 chromosomes, some of these having the improved engineered chromosome IEC-HC1 containing 4S$^s$S/4EL/6S$^I$L carrying Ms-S$^s$1, rht-S$^s$1, Ba-E1 and ki-S$^I$1-a and are the desired plants while some others contain the translocated chromosome 4S$^s$S/4EL;

(e) selecting the desired plants of (d) by chromosome count and by the use of DNA markers and selfing them;

(f) collecting the progeny seed of (e) and selecting the blue seeds, which seeds when grown, develop into male-fertile plants carrying the improved engineered chromosome IEC-HC1, these being the desired improved maintainer line plants;

(g) if in step (d) no desired plant is obtained, then selecting plants of (d) having the translocated chromosome $4S^sS/4EL$ (originating from blue seeds and being male-fertile) by chromosome count and by the use of DNA markers and backcrossing them as male parent to the maintainer line having the EC-H1 to produce $F_1$ seeds;

(h) selecting from said $F_1$ seeds of (g) the blue seeds, irradiating them by thermal neutrons and germinating them and selecting seedlings with 44 chromosomes, i.e., having two allien addition chromosomes $4S^sS/4EL$ and $4S^sS/6S^lL$; and (i) repeating steps (d)–(f), thus obtaining the desired improved maintainer line having the improved engineered chromosome IEC-HC1 containing $4S^sS/4EL/6S^lL$, carrying Ms-$S^s1$, rht-$S^s1$,Ba-E1 and ki-$S^l1$-a.

Figure 9C:
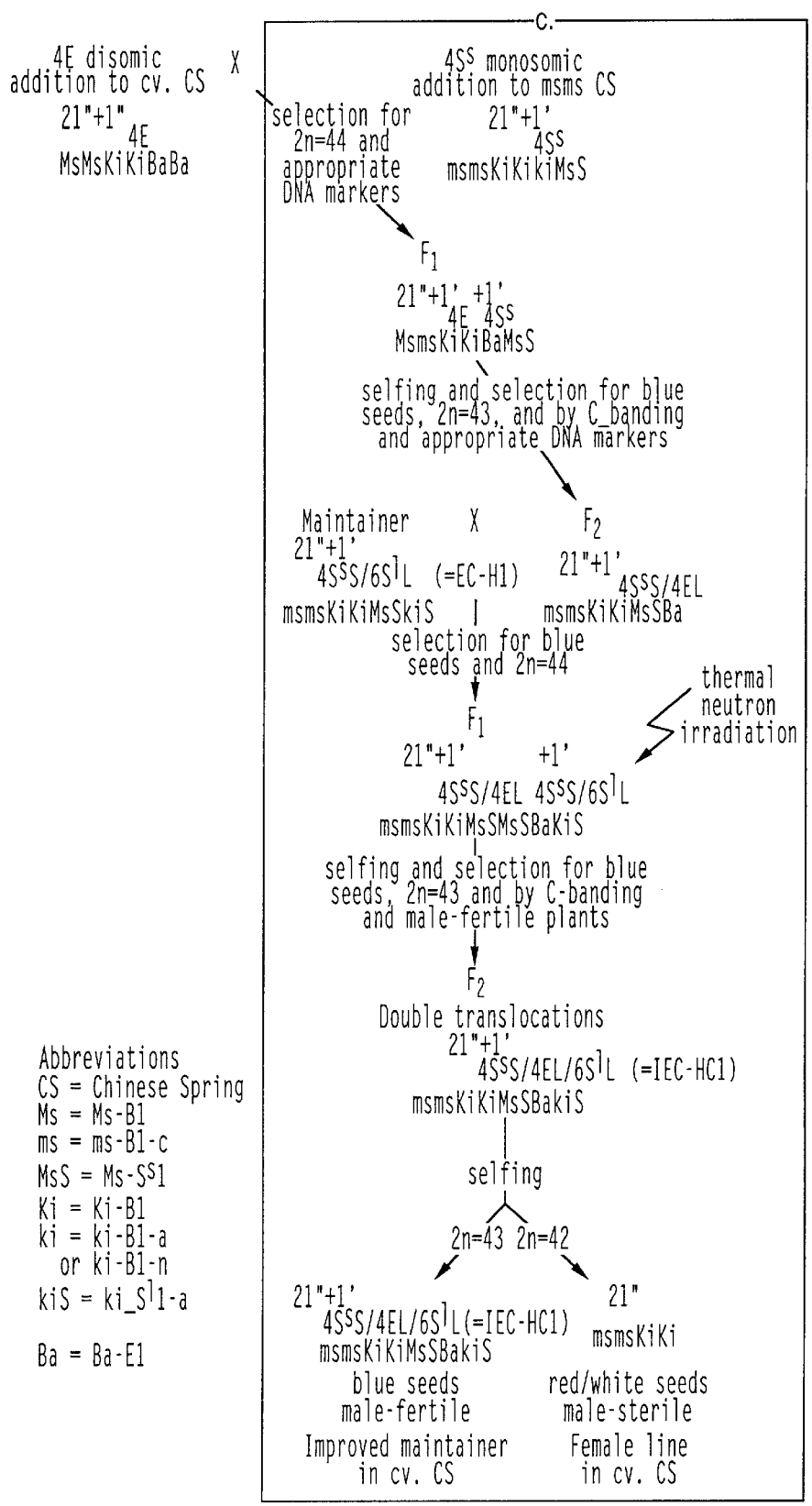
Figure 9D:
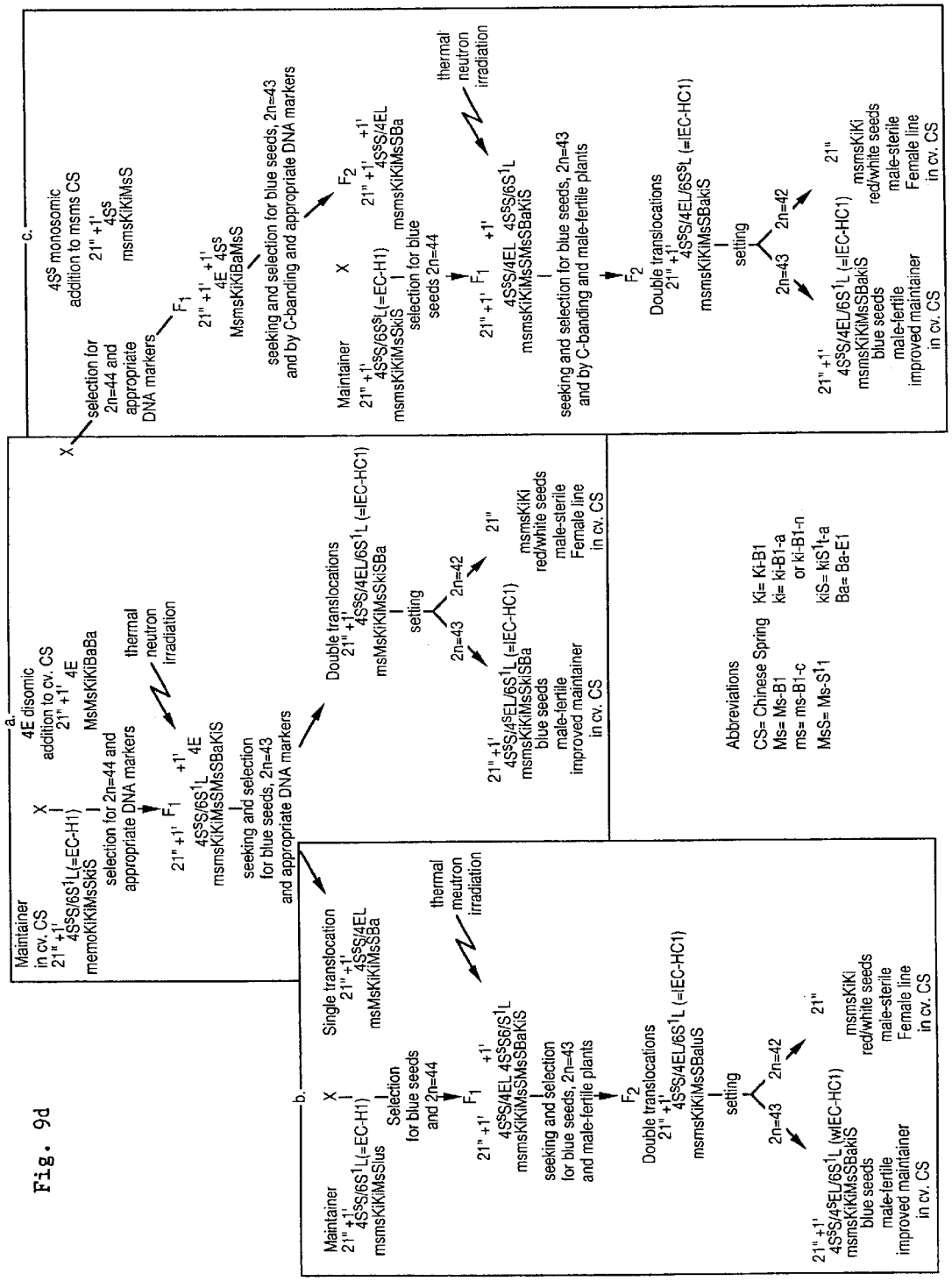

The present invention further provides another method for producing a male-fertile improved maintainer line of common or duruin wheat having the improved engineered chromosome IEC-HC1 (FIG. 9c), comprising:

(a) crossing a male-fertile female parent derived from the common wheat cultivar Chinese Spring, said female parent being homozygous for both the dominant male-fertility allele Ms-B1 and for the dominant pollen-killer Ki-B1 allele and having an additional pair of the alien chromosome 4E carrying on its long arm the dominant blue aleurone allele Ba-E1, with a male parent that is isogenic to the female parent, but is homozygous for the recessive male-sterility allele ms-B1-c and has an additional alien chromosome $4S^s$ carrying on its short arm the dominant alleles Ms-$S^s1$ and rht-$S^s1$;

(b) collecting the progeny seed of the cross of (a) and growing said seeds, thus producing $F_1$ plants, all of which are heterozygous Ms-B1ms-B1 and homozygous Ki-B1Ki-B1, 25% of which are double monosomic addition carrying chromosomes 4E and $4S^s$ and are the desired plants;

(c) selecting said desired $F_1$ plants of (b) by chromosome count and use of DNA markers and selfing them;

(d) selecting from the selfed seeds of (c) the blue ones and growing said seeds, thus producing $F_2$ plants, some of which having a translocated chromosome $4S^sS/4EL$ and are the desired plants;

(e) selecting said desired $F_2$ plants of (d) by chromosome count and use of DNA markers and crossing them as male with the maintainer line having the EC-H1 ($4S^sS/6S^lL$) and obtaining $F_1$ seeds, some of which are blue;

(f) selecting the blue seeds of (e), irradiating them with thermal neutrons and growing them into $F_1$ plants, all of which are homozygous for both ms-B1-c and Ki-B1, few of them having the double monosomic addition $4S^sS/4EL$ and $4S^sS/6S^lL$ and are the desired plants;

(g) selecting said desired plants of (f) by chromosome count and use of DNA markers and selfing them;

(h) collecting the progeny seed of (g), selecting the blue seeds and growing them, thus producing $F_2$ plants, all of which are homozygous for both ms-B1-c and Ki-B1 alleles, some of which having 43 chromosomes, some of these having the improved engineered chromosome IEC-HC1 containing $4S^sS/4EL/6S^lL$ carrying Ms-$S^s1$, rht-S1, Ba-E1 and ki-$S^l$ and are the desired plants;

(i) selecting the desired plants of (h) by chromosome count, C-banding and male-fertility and selfing them; and (j) collecting the progeny seed of (i) and selecting the blue seeds, said seeds when grown, developing into male-fertile plants carrying the IEC-HC1, these being the desired improved maintainer line plants.

Figure 10:
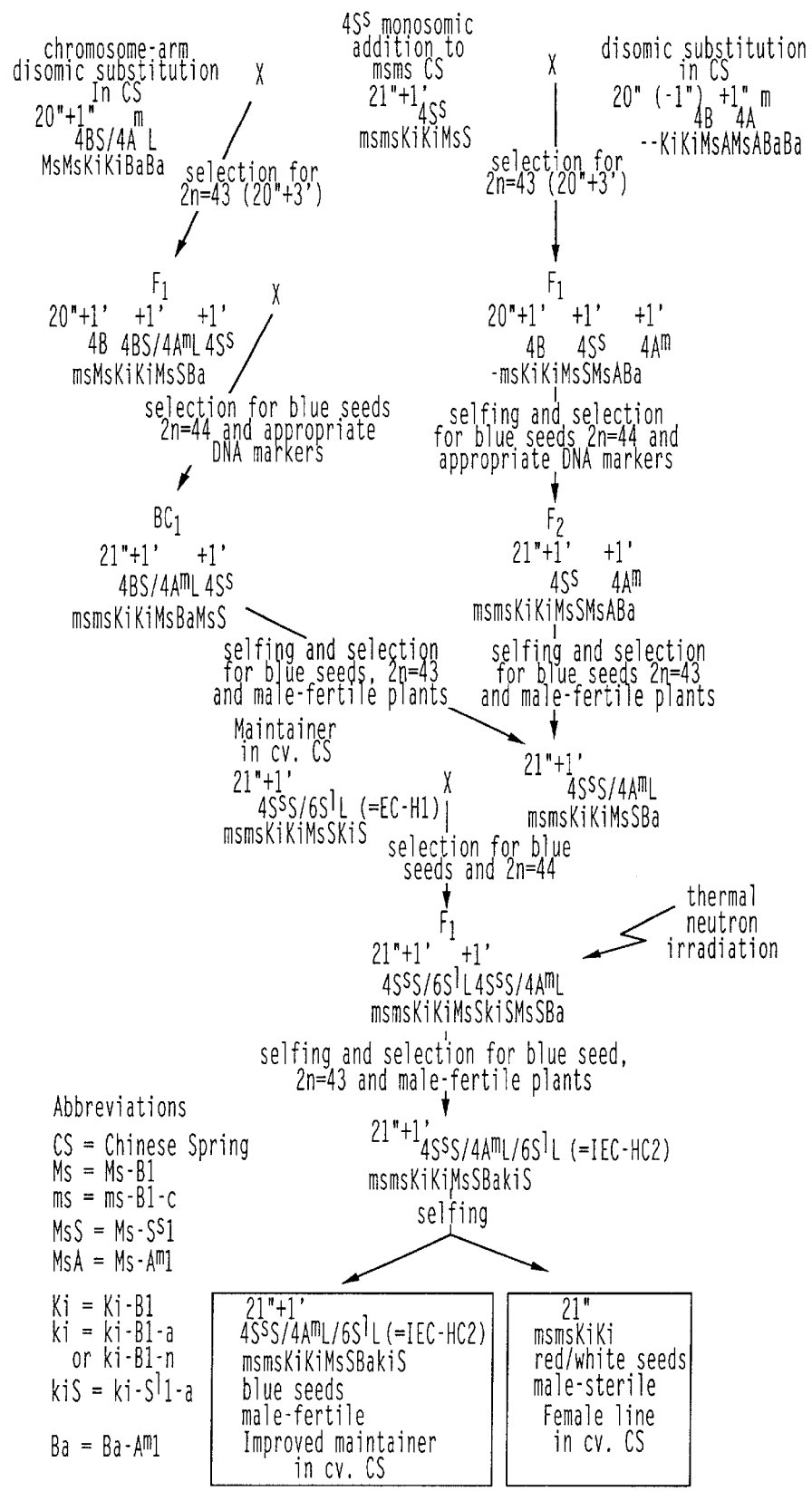
FIG. 10 depicts a schematic procedure for producing the maintainer line with the improved engineered chromosome IEC-HC2 carrying Ms-$S^s$1 and rht-$S^s$1from $4S^sS$ of Ae. searsii, Ba-$A^m$1 from $4A^mL$ of T. monococcum, and ki-$S^l$1-a from $6S^lL$ of Ae. longissima, as well as the male-sterile female line, in the common wheat cultivar Chinese Spring.

The present invention also provides a method for producing a male-fertile improved maintainer line of common or durum wheat having the improved engineered chromosome IEC-HC2 (FIG. 10), comprising:

(a) crossing a male parent disomic substitution line of the common wheat cv. Chinese Spring in which chromosome $4A^m$ of T. monococcum substitutes for chromosome 4B of common wheat and therefore said male parent is deficient for the male-fertility allele Ms-B1, homozygous for the pollen-killer allele Ki-B1 and for Ms-$A^m1$ and rht-$A^m$ on $4A^mS$ and Ba-$A^m1$ on $4A^mL$, with a female parent isogenic to the male parent but homozygous for the recessive ms-B1 male-sterility allele and having an additional alien chromosome $4S^s$ carrying on its short arm the dominant alleles Ms-$S^s1$ and rht-$S^s1$;

(b) collecting the progeny seed of the cross of (a), all of which being blue, and growing said seeds, thus producing $F_1$ plants, all of which are hemnizygous for ms-B1-c and homozygous for Ki-B1, some of which being triple monosomic 4B, $4S^s$ and $4A^m$ and are the desired plants;

(c) selecting said triple monosomic plants of (b) by chromosome count, thus producing male-fertile $F_1$ plants, and allowing them to self-pollinate;

(d) collecting $F_2$ seeds of (c), selecting the blue seeds and growing said selected seeds, thus producing $F_2$ plants, and further selecting from these $F_2$ plants those having 44 chromosomes (showing 21"+2' at meiosis) being the desired double monosomic addition $4S^s$ and $4A^m$;

(e) selfing said desired plants of (d), thus obtaining $F_3$ seeds and selecting the blue ones;

(f) growing the blue seeds of (e) and selecting plants having 43 chromosomes (21"+1), which are male-fertile and produce blue seeds, these plants having the translocated chromosome $4S^sS/4A^mL$ and are the desired plants;

(g) crossing the desired plants of (f) as male with the maintainer line which is homozygous ms-B1msB1Ki-B1KiB1 and having EC-H1 ($4S^sS/6S^lL$) carrying Ms-$S^s1$rht-$S^s1$ki-$S^l1$-a as female and obtaining $F_1$ seeds;

(h) selecting from the $F_1$ progeny seed of (f) blue seeds, irradiating them with thermal neutrons and growing them, and further selecting plants having 44 chromosomes (21"+1"), i.e., which are disomic for the short arm and double monosomic for the long arm of the alien addition chromosomes, and selfing them;

(i) growing the blue seeds of (h) and selecting male-fertile plants having 43 chromosomes and producing blue and red/white seeds, these plants having the IEC-HC2 and are the desired plants; and (j) selfing the-desired plants of (i), collecting seeds thereof and separating the blue seeds, said seeds, when grown, developing into male-fertile plants having the IEC-HC2, these being the desired improved maintainer line plants.

Figure 11:
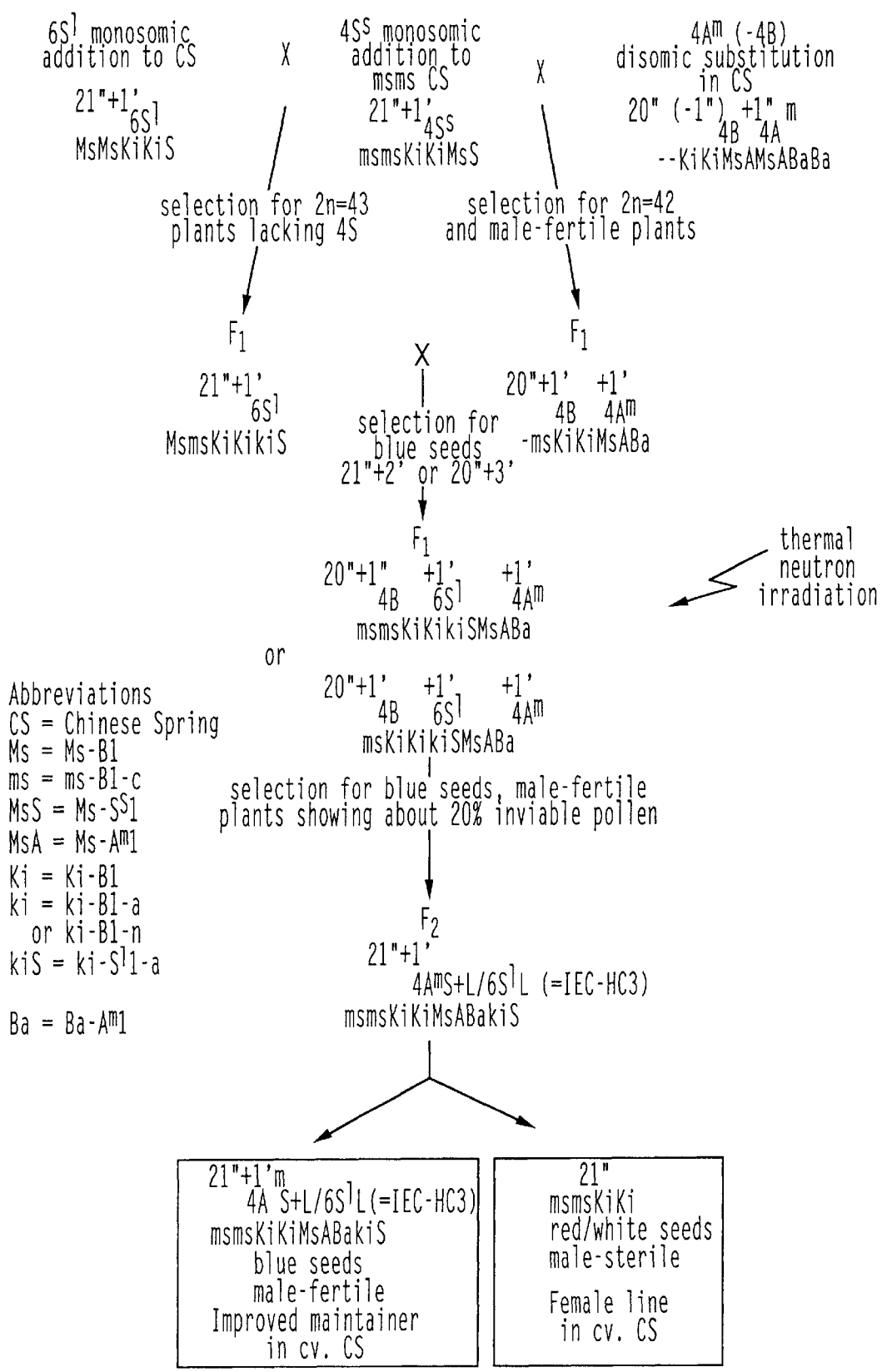
FIG. 11 depicts a schematic procedure for producing the maintainer line with the improved engineered chromosome IEC-HC3 carrying Ms-$A^m$1 and rht-$A^m$1 from $4A^mS$ of T. monococcum, Ba-$A^m$1 from $4A^mL$ of T. monococcum, and ki-$S^l$1-a from $6S^lL$ of Ae. longissima, as well as the male-sterile female line, in the common wheat cultivar Chinese Spring.

The present invention also, provides a method for producing a male-fertile maintainer line of common or durum wheat having the improved engineered chromosome EEC-HC3 (FIG. 11), comprising:
- (a) crossing a male parent disomic substitution line of the common wheat cv. Chinese Spring in which chromosome $4A^m$ of *T. monococcum* substitutes for chromosome 4B of common wheat and therefore said male parent is deficient for the male-fertility allele Ms-B1, homozygous for the pollen-killer allele Ki-B1 and for Ms-$A^m$1 and rht-$A^m$1 on $4A^m$S and Ba-$A^m$1 on $4A^m$L, with a female parent isogenic to the male parent but homozygous for the recessive ms-B1 male-sterility allele and having an additional alien chromosome $4S^s$ carrying on its short arm the dominant alleles Ms-$S^s$1 and rht-$S^s$1;
- (b) collecting the $F_1$ seeds of (a) all of which are blue, and growing said seeds all of which are hemizygous for ms-B1-c and homozygous for Ki-B1, of which 75% are monosomic 4B and monosomic substitution $4A^m$ carrying Ms-$A^m$1 and therefore male-fertile, and using said monosomic-monosomic substitution to pollinate a female parent heterozygous Ms-B1ms-B1 and homozygous for the Ki-B1 allele and having chromosome $6S^l$ as monosomic addition, wherein said female parent is obtained by crossing the $4S^s$ monosomic addition to ms-B1-cms-B1-c Chinese Spring as male with a female parent homozygous for Ms-B1 and Ki-B1 alleles and having chromosome $6S^l$ as a monosomic addition, 20% of the progeny having the desired constitution;
- (c) collecting the blue $F_1$ seeds from the cross of (b) and irradiating them with thermal neutrons, growing them and selecting from the $F_1$ plants those having 43 (21"+1') and 42 (20"+2') chromosomes and selfing these plants;
- (d) selecting from the selfed seeds of (c) the blue ones and growing them and selecting plants that are male-fertile, have about 20% inviable pollen and produce blue and red/white seeds; and
- (e) growing the seeds of (d) and separating the blue seeds, said seeds, when grown, developing into male-fertile plants with the IEC-HC3 (having 43 chromosomes), these being the desired improved maintainer line plants.

Figure 12:
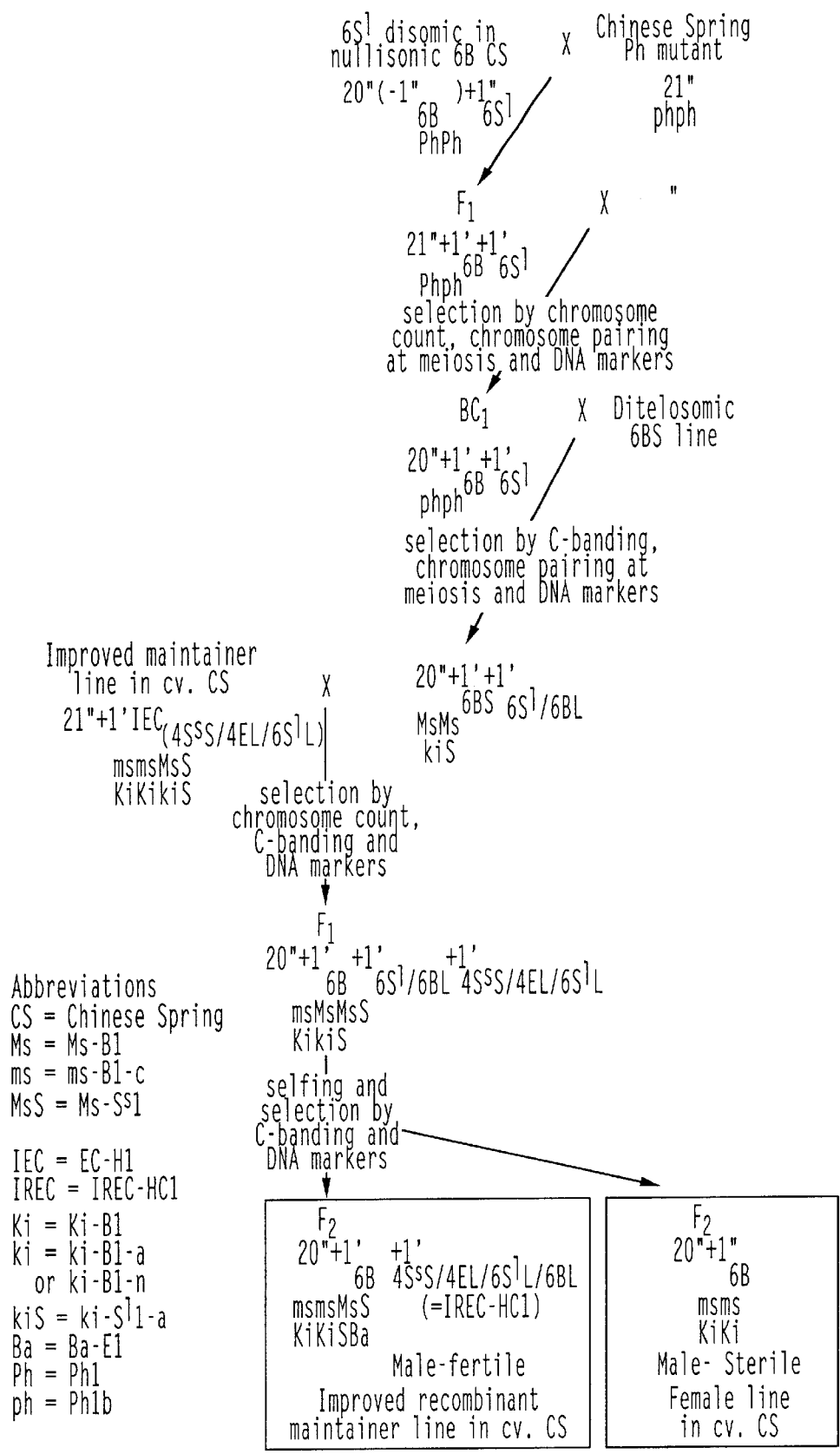
FIG. 12 depicts a schematic procedure for producing the maintainer line with the improved recombinant engineered chromosome IREC-HC1, carrying Ms-$S^s$1 and rht-$S^s$1 from $4S^sS$ of Ae. searsii and ki-$S^l$1-a from $6S^lL$ of Ae. longissima, as well as the male-sterile female line in the common wheat cultivar Chinese Spring.

The present invention further provides a method for producing a male-fertile maintainer line of common or durum wheat having an improved recombinant engineered chromosome IREC-HC (FIG. 12), comprising:
- (a) crossing a male-fertile female parent derived from the common wheat cultivar Chinese spring, said female parent being homozygous for the dominant Ms-B1 male-fertility allele on chromosome arm 4BS and for the dominant homoeologous-pairing suppressor allele Ph1 on chromosome arm 5BL, nullisomic for chromosome 6B and therefore deficient for the dominant Ki-B1 pollen-killer allele, and having a pair of $6S^l$ chromosomes carrying the recessive pollen-killer allele ki-$S^l$1-a, with a male parent, that is isogenic to the female parent but is disomnic 6B and therefore homozygous for Ki-B1, lacks chromosome $6S^l$, and is also homozygous for the mutant homoeologous-pairing allele ph1b;
- (b) collecting the progeny seed of the cross of (a) and growing said seed, thus producing male-fertile (Ms-B1Ms-B1) $F_1$ plants heterozygous for the homoeologous-pairing alleles (Ph1ph1b), all of which are monosomic for both 6B and $6S^l$ chromosomes;
- (c) backcrossing said $F_1$ plants of (b) to the male parent;
- (d) collecting the progeny seed of the cross of (c) and growing said seeds, thus producing $BC_1$ plants, all of which are male-fertile (Ms-B1Ms-B1), ½ of which are homozygous for the ph1b allele, of which about ½ (because 6B pairs with $6S^l$) are double monosomic for both 6B and $6S^l$ chromosomes and are the desired $BC_1$ plants;
- (e) selecting the desired $BC_1$ plants of (d) by chromosome pairing at meiosis and by DNA markers, and pollinating them by a ditelosomic 6BS line (i.e. deficient for 6BL arms) which is isogenic to the $BC_1$ plants but is homozygous Ph1Ph1;
- (e collecting the progeny seed of the cross of (e) and growing said seeds, thus producing plants which are monotelosomic for 6BS, some of which are also monosomic for a recombinant chromosome consisting of the short arm and the proximal region of the long arm of $6S^l$ (carrying ki-$S^l$1-a) and the distal region of chromosome arm 6BL (the translocation point is distal to ki-$S^l$1-a) and are the desired plants;
- (g) selecting said desired plants of (f) by C-banding and by analysis of chromosome pairing and use of DNA markers and crossing them as males with a female line which is the improved maintainer line, i.e., homozygous for both any one of the recessive male-sterility allele ms-B1 and the dominant pollen-killer allele Ki-B1 and has one of the improved engineered chromosomes IEC-HC1 ($4S^sS/4EL/6S^lL$), IEC-HC2 ($4S^sS/4A^mL/6S^lL$) or IEC-HC3 ($4A^mS$-$4A^mL/6S^lL$) carrying Ms-$S^s$1, Ba-E1 and ki-$S^l$1-a, Ms-$S^s$1, rht-$S^s$1, Ba-$A^m$1 or ki-$S^l$1-a, and Ms-$A^m$1, rht-$A^m$1, Ba-$A^m$1 and ki-$S^l$1-a, respectively;
- (h) collecting the progeny seed of the cross of (g) and growing said seeds, thus producing $F_1$ plants, some of which are triple monosomics, i.e., monosomic for 6B, for one of the improved engineered chromosomes IEC-HC1, IEC-HC2 or IEC-HC3 and for the recombinant chromosome ($6S^l/6BL$) and are heterozygous ms-B1Ms-B1 and hemizygous Ki-B1 and are the desired plants; and
- (i) selecting said desired plants of (h) by chromosome count, C-banding and by the use of DNA markers and selfing them, collecting the progeny seed thereof and growing said seeds, some of which are double monosomics, having chromosome 6B and the improved recombinant engineered chromosome IREC-HC, either IREC-HC1 ($4S^sS/4EL/6S^lL/6BL$), IREC-HC2 ($4S^sS/4A^mL/6S^lL/6BL$) or IREC-HC3 ($4A^mS$-$4A^mL/6S^lL/6BL$), these being the desired maintainer lines plants with the IREC-HC.

In another aspect the present invention provides a method for maintaining a constant ratio between male-fertile to male-sterile plants in each generation of the maintainer line or a recombinant maintainer line of common and durum wheat, comprising:
- (a) selfing a male-fertile maintainer line containing an engineered chromosome selected from the group of the engineered chromosome EC-H1 and the recombinant engineered chromosome REC-H1, carrying, in addition to the Ms-$S^s$1 and ki-$S^l$1-a alleles, the rht-$S^s$1 allele as a selectable marker that facilitates the separate harvest of seeds from the male-fertile progeny of the selfed maintainer, said seeds, when grown, developing into said maintainer line;
- (b) collecting the progeny seeds of (a) and growing said seeds thus producing plants, 20% of which (progeny of the maintainer line having the engineered chromosome EC-H1) and 50% of which (progeny of the maintainer line having the recombinant engineered chromosome REC-H1) contain the said engineered chromosome, and are the same as the said maintainer line and therefore carry the rht-S$^s$1 allele and are taller (by 6–8 cm) than those lacking the said engineered chromosome; and (c) harvesting the taller plants of (b), all of which are male-fertile, and obtaining the progeny seeds consisting of 20% (EC-H1) or 50% (REC-H1) seeds carrying the said engineered chromosome, thus keeping constant the ratio of male-fertile to male-sterile plants in each generation of the maintainer line or the recombinant maintainer line.

The present invention further provides a method for maintaining a constant ratio between male-fertile to male-sterile plants in each generation of the maintainer line or a recombinant maintainer line of common and durum wheat, comprising:

(a) selfing a male-fertile maintainer line containing an engineered chromosome selected from the group of the engineered chromosome EC-HR1 and the recombinant engineered chromosome REC-HR1, carrying, in addition to the Ms-S$^s$1 and ki-S$^l$1-a alleles, the Su-S$^s$1 allele as a selectable marker that facilitates the selection of plants having the same said maintainer genotype from the male-fertile progeny of the selfed maintainer line;

(b) collecting the progeny seeds of (a), germinating said seeds into a seedling progeny, 20% of which (progeny of the maintainer line having the engineered chromosome EC-HR1) and 50% of which (progeny of the maintainer line having the recombinant engineered chromosome REC-HR1) contain the said engineered chromosome, and spraying the seedlings with the herbicide chlorotoluron thus killing all the susceptible seedlings, i.e., those lacking the EC-HR1 or the REC-HR1; and (c) harvesting the chlorotoluron resistant plants of (b), all of which carry the EC-HR1 or the REC-HR1 and therefore are male-fertile, and obtaining the progeny seeds consisting of 20% (EC-HR1) or 50% (REC-HR1) seeds carrying the said engineered chromosome, thus keeping constant the ratio of male-fertile to male-sterile plants in each generation of the maintainer or the recombinant maintainer.

The present invention also provides a method for maintaining a constant ratio between male-fertile to male-sterile plants in each generation of the improved maintainer line or the improved recombinant maintainer line of common and durum wheat, comprising:

(a) selfing a male-fertile maintainer line containing an engineered chromosome selected from the group of the engineered chromosome IEC-HC1 and the recombinant engineered chromosome IREC-HC1, carrying, in addition to the Ms-S$^s$1 and ki-S$^l$1-a alleles, the Ba allele (inducing blue seeds) as a selectable marker that facilitates the selection of seeds from the male-fertile progeny of the selfed maintainer, said seeds, when grown, developing into said maintainer line;

(b) collecting the progeny seeds of (a), and separating the blue seeds carrying the IEC-HC1 or the IREC-HC1 from the red/white seeds lacking these chromosomes, by a sorting apparatus; and (c) planting the blue seeds of (b), all of which develop into male-fertile improved maintainer or improved recombinant maintainer plants.

In another aspect the present invention provides a method for preventing the breakage, through centromeric misdivision at meiosis, of the engineered chromosome, into two telocentric (one arm) chromosomes carrying either the Ms and rht alleles of the short arm of the engineered chromosome or the ki-S$^l$1-a allele and, in the case of EC-HR, also the Su allele whereas in the case of IEC, also the Ba allele, of the long arm. Separation between Ms and ki-S$^l$1-a may result in a male transmission of Ms and hence, in the production of certain amount of male-fertile female plants upon pollination of the female line by the maintainer or the improved maintainer or upon selfing the improved maintainer. In the two latter cases, the seeds carrying Ms, when grown, develop into male-fertile plants, will be red/white and unseparable from those lacking Ms, which seeds when grown, develop into male-sterile plants. In the case of EC-HR, plants having only the short arm of the engineered chromosome, carrying Ms-S$^s$1 and rht-S$^s$1, are susceptible to chlorotoluron and can be selected against in the application of the herbicide. The use of the recombinant maintainer or the improved recombinant maintainer, instead of the maintainer or the improved maintainer, eliminates the danger of male transmission of the Ms allele. In these maintainers the recombinant or the improved recombinant engineered chromosome pairs regularly with the native 6B chromosome and consequently, centromeric misdivision, which normally does not occur in paired chromosomes, is prevented. This sustains the linkage between Ms and ki-S$^l$1-a.

In another aspect the present invention provides a method for converting a desired cultivar of common and durum wheat into a male-sterile female parental line and a male-fertile maintainer line having an engineered chromosome EC-H, for said female line (FIG. 16a), said method comprising:

(a) crossing a maintainer line being homozygous ms-B1ms-B1Ki-B1Ki-B1 and having an alien engineered chromosome EC-H1 (4S$^s$S/6S$^l$L), carrying Ms-S$^s$1, rht-S$^s$1 and ki-S$^l$1-a, with the desired cultivar which is homozygous Ms-B1Ms-B1ki-B1ki-B1;

(b) collecting the progeny seed of the cross of (a) and growing said seeds, thus producing male-fertile F$_1$ plants, all of which are heterozygous ms-B1Ms-B1Ki-B1ki-B1-a, ¼ of which also carry the engineered chromosome EC-H1 and are the desired plants;

(c) selecting by chromosome counts and by the use of DNA markers said desired F$_1$ plants of (b) and pollinating them by the desired cultivar to produce BC$_1$ progeny, 1/16 of which are heterozygous ms-B1Ms-B1Ki-B1ki-B1-a and carry the engineered chromosome EC-H1 and are the desired genotype;

(d) growing said BC$_1$ plants of (c) and selecting said desired genotype by chromosome counts and by the use of DNA markers, and further backcrossing them as female with the desired cultivar through four subsequent generations to yield fifth generation backcross progeny (BC$_5$) while selecting at each generation for heterozygous ms-B1Ms-B1Ki-B1ki-B1-a offspring that have the engineered chromosome EC-H1 by chromosome counts and by the use of DNA markers; and (e) selfing:the desired BCS plants of (d), collecting the progeny seed thereof and growing said seeds thus growing BC$_5$F$_2$ plants, 1/16 of which are male-sterile homozygous both for the male-sterility ms-B1 and for the pollen-killer Ki-B1 alleles and are the desired male-sterile female line, and other BC$_5$F$_2$ plants with similar genotype but having also the engineered chromosome EC-H1 carrying Ms-S$^s$1, rht-S$^s$1 and ki-S$^l$1-a, these being the desired male-fertile maintainer line plants.

The present invention also provides a method for converting a desired cultivar of common and durum wheat into a male-sterile female parental line and a male-fertile maintainer line having an engineered chromosome EC-HR, for said female line (FIG. 17a), said method comprising:

(a) crossing a maintainer line being homozygous ms-B1ms-B1ms-B1su-B1Ki-B1Ki-B1 and having an alien engineered chromosome EC-HR1, carrying Ms-S$^s$1, rht-S$^s$1, Su-S$^s$1 and ki-S$^l$1-a, with the desired cultivar which is homozygous Ms-B1Ms-B1Su-B1Su-B1ki-B1ki-B1;

(b) collecting the progeny seed of the cross of (a) and growing said seeds, thus producing male-fertile $F_1$ plants, all of which are heterozygous ms-B1Ms-B1Su-B1su-B1Ki-B1ki-B1-a, ¼ of which also carry the engineered chromosome and are the desired plants;

(c) selecting by chromosome counts and by the use of DNA markers said desired $F_1$ plants of (b) and pollinating them by the desired cultivar to produce $BC_1$ progeny, 1/32 of which are heterozygous ms-B1Ms-B1Su-B1su-B1Ki-B1ki-B1-a and carry the engineered chromosome EC-HR1 and are the desired genotype;

(d) growing said $BC_1$ plants of (c) and selecting said desired genotype by chromosome counts and by the use of DNA markers, and further backcrossing them as female with the desired cultivar through four subsequent generations to yield fifth generation backcross progeny ($BC_5$) while selecting at each generation for heterozygous ms-B1Ms-B1Su-B1su-B1Ki-B1ki-B1-a offspring that have the engineered chromosome EC-HR1 by chromosome counts and by the use of DNA markers; and (e) selfing the desired $BC_5$ plants of (d), collecting the progeny seed thereof and growing said seeds thus growing $BC_5F_2$ plants, 1/64 of which are male-sterile homozygous both for the male-sterility ms-B1, for the chlorotoluron susceptibility su-B1 and for the pollen-killer Ki-B1 alleles and are the desired male-sterile female line, and other $BC_5F_2$ plants with similar genotype but having also the engineered chromosome EC-HR1 carrying Ms-S$^s$1, rht-S$^s$1, S$^l$1-S$^s$1 and ki-S$^l$1-a, these being the desired male-fertile maintainer line plants.

The present invention further provides a method for converting a desired cultivar of common and durum wheat into a male-sterile female parental line and a male-fertile recombinant maintainer line having a recombinant engineered chromosome REC-H for said female line (FIG. 16b), said method comprising:

(a) crossing as female a maintainer line with REC-H1, being homozygous ms-B1ms-B1 and monosomic for both 6B (hemizygous for Ki-B1) and the recombinant engineered chromosome REC-H1 (4S$^s$S/6S$^l$L/6BL), carrying Ms-S$^s$1, rht-S$^s$1 and ki-S$^l$1-a, with the desired cultivar which is homozygous Ms-B1Ms-B1ki-B1ki-B1;

(b) collecting the progeny seed of the cross of (a) and growing said seeds, thus producing male-fertile $F_1$ plants, all of which are heterozygous ms-B1Ms-B1, ½ of which are disomic for chromosome 6B and therefore are heterozygous Ki-B1ki-B1-a, and ½ of which are double monosomic for chromosome 6B and for the recombinant engineered chromosome REC-H1 and are hemizygous for the ki-B1-a but also carry Ms-S$^s$1, rht-S$^s$1 and ki-S$^l$1-a of the recombinant engineered chromosome;

(c) selecting said two types of $F_1$ progeny of (b) by analysis of chromosome pairing and use of DNA markers, and pollinating them by the desired cultivar to produce two types of $BC_1$ progeny, those derived from the disomic $F_1$, ¼ of which are heterozygous ms-B1Ms-B1Ki-B1ki-B1-a, and those derived from the double monosomic $F_1$, ¼ of which are double monosomic, heterozygous ms-B1Ms-B1 and hemizygous for ki-B1-a and carry also MsS$^s$1, rht-S$^s$1 and ki-S$^l$1-a of the recombinant engineered chromosome REC-H1;

(d) selecting said desired plants of the two groups of (c) by analysis of chromosome pairing and by use of DNA markers, and further backcrossing them as female with the desired cultivar through four subsequent generations to yield two types of fifth generation backcross progeny ($BC_5$) while selecting at each generation for heterozygous ms-B1Ms-B1Ki-B1ki-B1-a in the disomic type and for ms-B1Ms-B1 in the double monosomic type that has the recombinant engineered chromosome REC-H1, by chromosome pairing analysis and by use of DNA markers;

(e) pollinating the desired double monosomic $BC_5$ plants of (d) by the desired disomic $BC_5$ of (d) to produce two groups of $BC_5F_2$, a group of disomic plants, ⅛ of which are homozygous ms-B1ms-B1 and heterozygous Ki-B1ki-B1-a and are the desired disomic plants and a group of double monosomic plants, ⅛ of which is homozygous ms-B1ms-B1 and hemizygous for Ki-B1 and also carries Ms-S$^s$1, rht-S$^s$1 and ki-S$^l$1-a of the recombinant engineered chromosome REC-H1 and therefore are male-fertile and are the desired recombinant maintainer line; and (f) growing said double monosomic $BC_5F_2$ seeds of (e) and the disomic $BC_5F_2$ seeds of (e) and selecting by analysis of chromosome pairing and by the use of DNA markers the desired male-fertile recombinant maintainer line and the male-sterile female line, respectively.

The present invention also provides a method for converting a desired cultivar of common and durum wheat into a male-sterile female parental line and a male-fertile recombinant maintainer line having a recombinant engineered chromosome REC-HR, for said female line (FIG. 17b), said method comprising:

(a) crossing as female a maintainer line with REC-HR1, being homozygous ms-B1ms-B1 and monosomic for both 6B (hemizygous for su-B1 and Ki-B1) and the recombinant engineered chromosome REC-HR1, carrying Ms-S$^s$1, rht-S$^s$1 Su-S$^s$1 and ki-S$^l$1-a, with the desired cultivar which is homozygous Ms-B1Ms-B1Su-B1Su-B1ki-B1ki-B1;

(b) collecting the progeny seed of the cross of (a) and growing said seeds, thus producing male-fertile $F_1$ plants, all of which are heterozygous ms-B1Ms-B1, ½ of which are disomic for chromosome 6B and therefore are heterozygous Su-B1su-B1Ki-B1ki-B1 and ½ of which are double monosomic for chromosome 6B and for the recombinant engineered chromosome REC-HR1 and are hemizygous for the Su-B1 and ki-B1-a but also carry Ms-S$^s$1, rht-S$^s$1, Su-S$^s$1 and ki-S$^l$1-a of the recombinant engineered chromosome REC-HR1;

(c) selecting said two types of $F_1$ progeny of (b) by analysis of chromosome pairing and use of DNA markers, and pollinating them by the desired cultivar to produce two types of $BC_1$ progeny, those derived from the disomic $F_1$, ¼ of which are heterozygous ms-B1Ms-B1 and those derived from the double monosomic $F_1$, ¼ of which are double monosomic, heterozygous ms-B1Ms-B1 and hemizygous for Su-B1 and ki-B1 and carry also Ms-$S^s$1, rht-$S^s$1, SU-$S^s$1 and ki-$S^l$1-a of the recombinant engineered chromosome REC-HR1;

(d) growing said $BC_1$ progeny of (c) and selecting said desired plants of the two groups of (c) by analysis of chromosome pairing and by use of DNA markers, and further backcrossing them as female with the desired cultivar through four subsequent generations to yield two types of fifth generation backcross progeny ($BC_5$) while selecting at each generation for heterozygous ms-B1Ms-B1su-B1Su-B1Ki-B1ki-B1 in the disomic type and for ms-B1Ms-B1 in the double monosomic type that has the recombinant engineered chromosome REC-HR1, by chromosome pairing analysis and by use of DNA markers;

(e) pollinating the desired double monosomic $BC_5$ plants of (d) by the desired disomic $BC_5$ of (d) to produce two groups of $BC_5F_2$, a group of disomic plants, 1/16 of which are homozygous ms-B1ms-B1 and heterozygous su-B1Su-B1Ki-B1ki-B1 and are the desired disomic plants and a group of double monosomic plants, 1/16 of which is homozygous ms-B1ms-B1 and hemizygous for su-B1 and Ki-B1 and also carries Ms-$S^s$1, rht-$S^s$1, Su-$S^s$1 and ki-$S^l$1-a of the recombinant engineered chromosome REC-HR1 and therefore are male-fertile and are the desired recombinant maintainer line;

(f) growing said double monosomic $BC_5F_2$ seeds of (e) and the disomic $BC_5F_2$ seeds of (e) and selecting by analysis of chromosome pairing and by the response to chlorotoluron the desired male-fertile recombinant maintainer line and the male-sterile female line;

(g) growing the progeny of the disomic plants, all of which are homozygous ms-B1ms-B1 and therefore male-sterile, ¼ of which are homozygous su-B1su-B1 and Ki-B1Ki-B1 and are the desired male-sterile female line; and (h) growing said disomic $BC_5F_3$ of (g) and selecting by the use of DNA markers the desired male-sterile female line.

The present invention also provides a method for converting a desired cultivar of common and durum wheat into a male-sterile female parental line and a male-fertile improved maintainer line for said female line of the IEC-HC type (FIG. 18a), said method comprising:

(a) crossing an improved maintainer line being homozygous ms-B1ms-B1Ki-B1Ki-B1 and having an improved engineered chromosome either IEC-HC1 (4$S^s$S/4EL/6$S^l$L, carrying Ms-$S^s$1, rht-$S^s$1, Ba-E1 and ki-$S^l$1-a), IEC-HC2 (4$S^s$S/4$A^m$L/6$S^l$L, carrying Ms-$S^s$1, rht-$S^s$1, Ba-$A^m$1 and ki-$S^l$1-a) or IEC-HC3 (4$A^m$S-4$A^m$L/6$S^l$L, carrying Ms-$A^m$1, rht-$A^m$1, Ba-$A^m$1 and ki-$S^l$1-a) with the desired cultivar which is homozygous Ms-B1Ms-B1ki-B1ki-B1;

(b) collecting the progeny seed of the cross of (a) and growing said seeds, thus producing male-fertile $F_1$ plants, all of which are heterozygous ms-B1Ms-B1Ki-B1ki-B1-a, ¼ of which also carry the improved engineered chromosome of the IEC-HC type and are the desired plants;

(c) selecting by seed color said desired $F_1$ plants of (b) and pollinating them by the desired cultivar to produce $BC_1$ progeny, 1/16 of which are heterozygous ms-B1Ms-B1Ki-B1ki-B1-a and carry the improved engineered chromosome of the IEC-HC type and are the desired genotype;

(d) growing said $BC_1$ plants of (c) and selecting said desired genotype by seed color, chromosome counts and by the use of DNA markers, and further backcrossing them as female with the desired cultivar through four subsequent generations to yield fifth generation backcross progeny ($BC_5$) while selecting at each generation for heterozygous ms-B1Ms-B1Ki-B1ki-B1-a offspring that have the improved engineered chromosome of the IEC-HC type by seed color, chromosome counts and by the use of DNA markers; and (e) selfing the desired $BC_5$ plants of (d), collecting the progeny seed thereof, some of which are blue and some of which are red/white and growing said seeds thus growing $BC_5F_2$ plants, 1/16 of which are male-sterile homozygous both for the male-sterility ms-B1 and for the pollen-killer Ki-B1 alleles, originated from red/white seeds and are the desired male-sterile female line, and other $BC_5F_2$ plants with similar genotype but originated from blue seeds thus having also the improved engineered chromosome of the IEC-HC type carrying Ms, rht, Ba and ki-$S^l$1-a, these being the desired male-fertile improved maintainer line plants.

The present invention further provides a method for converting a desired cultivar of common and durum wheat into a male-sterile female parental line and a male-fertile improved recombinant maintainer line of the IREC-HC type for said female line (FIG. 18b), said method comprising:

(a) crossing as female a maintainer line with IREC-HC, being homozygous ms-B1ms-B1 and monosomic for both 6B (hemizygous for Ki-B1) and one of the improved recombinant engineered chromosomes IREC-HC1 (4$S^s$S/4EL/6$S^l$L/6BL, carrying Ms-$S^s$1, rht-$S^s$1, Ba-E1 and ki-$S^l$1-a), IREC-HC2 (4$S^s$S/4$A^m$L/6$S^l$L/6BL, carrying Ms-$S^s$1, rht-$S^s$1, Ba-$A^m$1 and ki-$S^l$1-a) and IREC-HC3 (4$A^m$S-4$A^m$L/6$S^l$L/6BL, carrying Ms-$A^m$1, rht-$A^m$1, Ba-$A^m$1 and ki-$S^l$1-a) with the desired cultivar which is homozygous Ms-B1Ms-B1ki-B1ki-B1;

(b) collecting the progeny seed of the cross of (a) and growing said seeds, thus producing male-fertile $F_1$ plants, all of which are heterozygous ms-B1Ms-B1, ½ of which are disomic for chromosome 6B and therefore are heterozygous Ki-B1ki-B1-a, and ½ of which are double monosomic for chromosome 6B and for the recombinant engineered chromosome of the IREC-HC type and are hemizygous for the ki-B1-a but also carry Ms, rht, Ba and ki-$S^l$1-a alleles of the recombinant engineered chromosome;

(c) selecting said two types of $F_1$ progeny of (b) by seed color, analysis of chromosome pairing and use of DNA markers, and pollinating them by the desired cultivar to produce two types of $BC_1$ progeny, those derived from the disomic $F_1$, ¼ of which are heterozygous ms-B1Ms-B1Ki-B1ki-B1-a, and those derived from the double monosomic $F_1$, ¼ of which are double monosomic, heterozygous ms-B1Ms-B1 and hemizygous for ki-B1-a and carry also Ms, rht, Ba and ki-$S^l$1-a alleles of the recombinant engineered chromosome of IREC-HC type;

(d) selecting said desired plants of the two groups of (c) by seed color, analysis of chromosome pairing and by use of DNA markers, and further backcrossing them as female with the desired cultivar through four subsequent generations to yield two types of fifth generation backcross progeny (BC$_5$) while selecting at each generation for heterozygous ms-B1Ms-B1Ki-B1ki-B1-a in the disomic type and for ms-B1Ms-B1 in the double monosomic type that has the improved recombinant engineered chromosome of IREC-HC type, by seed color, chromosome pairing analysis and by use of DNA markers;

(e) pollinating the desired double monosomic BC$_5$ plants of (d) by the desired disomic BC$_5$ of (d) to produce two groups of BC$_5$F$_2$, a group of disomic plants, ⅛ of which are homozygous ms-B1ms-B1 and heterozygous Ki-B1ki-B1-a, originated from red/white seeds and are the desired disomic plants and a group of double monosomic plants, originated from blue seeds, ⅛ of which is homozygous ms-B1ms-B1 and hemizygous for Ki-B1 and also carries Ms, rht, Ba and ki-S$^l$1-a alleles of the improved recombinant engineered chromosome of the IREC-HC type and therefore are male-fertile and are the desired improved recombinant maintainer line; and (f) growing said double monosomic BC$_5$F$_2$ seeds of (e) and the disomic BC$_5$F$_2$ seeds of (e) and selecting by analysis of chromosome pairing and by the use of DNA markers the desired male-fertile improved recombinant maintainer line and the male-sterile female line, respectively.

In the methods of the invention for producing the maintainer line or for converting a desired cultivar into a male-sterile female parental line and a male-fertile maintainer, the selection of the plants carrying the desired ms-B1 allele in any one of the progeny generations is by use of DNA probes that map on the distal end of chromosome arm 4BS, and serve to mark any mutant male sterility ms-B1 allele, permitting the selection of plants carrying said mutant allele. Any DNA probe which marks the sub-terminal region of 4BS can be used, such as for example PSR921 (M. D. Gale, Cambridge Laboratory, JII, Norwich, U.K.).

The use of these DNA markers is by virtue of the fact that some of the known mutant alleles involve terminal deletions of 4BS, and since the deletion bringing about the mutant allele ms-B1-c also includes the loci of these markers, it is easy to identify the homozygous plant (ms-B1-c ms-B1-c) by the absence (null phenotype) of these DNA markers. Hence, in crossing a plant homozygous for the dominant normal allele (Ms-B1Ms-B1) as female with a plant heterozygous (Ms-B1ms-B1-c) for the mutant allele as male, 50% of the F$_1$ are homozygous (Ms-B1Ms-B1) and 50% heterozygous (Ms-B1ms-B1-c). These F$_1$ plants are backcrossed, i.e. pollinated by the male parent (Ms-B1ms-B1-c) and ⅛ of the resulting backcross progeny (BC$_1$) are expected to be homozygous for ms-B1-c ms-B1-c. These homozygous plants are identified and selected by the use of a. DNA marker. Each additional backcross yields 50% homozygous recessive progeny which can be selected by the use of the above marker.

In the above methods of the invention, the selection of the plants carrying the desired ki-S$^l$1-a allele in any one of the progeny generations is by the use of DNA probes that map to a locus tightly linked to the said allele on 6S$^l$L, and serve to mark the said allele. An example of such DNA probe is FSR915 (M. D. Gale, Cambridge Laboratory, JII, Norwich, U.K.). The selection of plants carrying the desired ki-S$^l$1-a allele is carried out also by the proportion of aborted pollen grains.

Yet another aspect of the present invention is a method for producing hybrid plants of common or durum wheat, comprising:

(a) crossing a male parent with a male-sterile female parent of the same species, wherein said male parent is selected from any desired common or durum wheat cultivar, which, by its nature, is homozygous for the dominant wild-type male-fertility (Ms-B1) allele, and said male-sterile female parent is a line of said wheat species being homozygous for both any one of the recessive mutant male-sterility (ms-B1) alleles and the dominant pollen-killer (Ki-B1) allele, said male-sterile female parent being maintained by a maintainer line of the invention as noted above; and (b) collecting the progeny seed of the cross of (a), which seeds, when grown, develop into progeny hybrid plants all of which are male-fertile and are heterozygous for the said mutant male-sterility allele, i.e., ms-B1Ms-B1.

EXAMPLES

In the examples below, the Aegilops lines used were a line of *Aegilops searsii* Feldman & Kislev ex Hammer, containing the Ms-S$^s$1 (male-fertility), the rht-S$^s$1 (taller plant) and the SuS$^s$1 (chlorotoluron resistance) alleles, herein designated AES-5, collected in Yattir, Southern Judea, Israel, and a line of *Aegilops longissima* Schweinf. & Muschl. containing the ki-S$^l$1-a (sensitive to the pollen killing effect of Ki-B1) allele, herein designated AEL-1, collected near Revivim, Central Negev, Israel.

Seeds of AES-5 and AEL-1 were deposited under the Budapest Treaty on the International Recognition of the Deposit of Microorganisms for the Purpose of Patent Procedure at NCIMB Ltd., Aberdeen, Scotland, United Kingdom, and were assigned the numbers 40952 and 40953, respectively, on May 13, 1998.

The present invention will now be described in more detail in the following non-limiting examples and their accompanying drawings.

Example 1

The Hybrid System

Figure 1C:
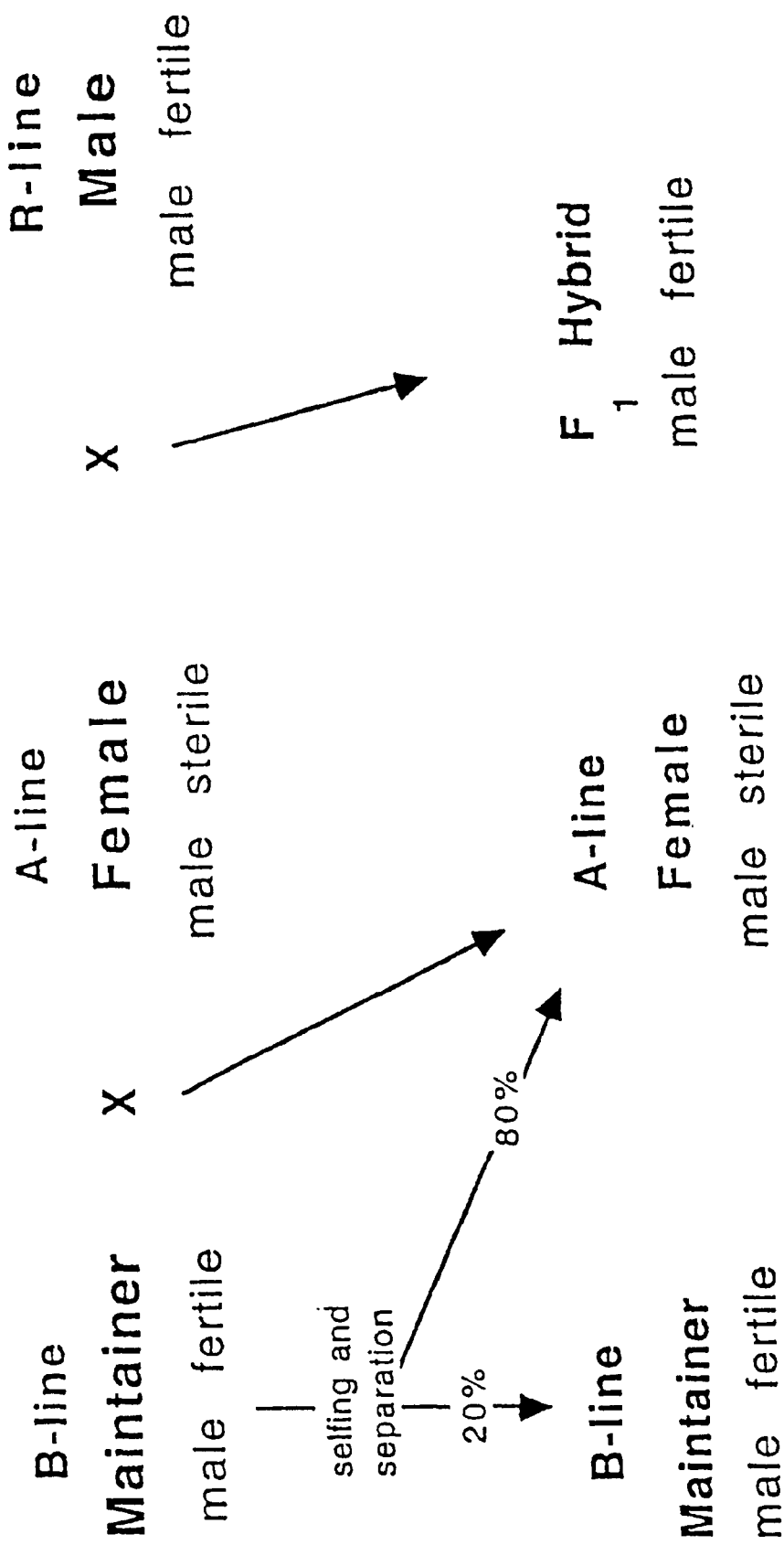

The three schemes for hybrid seed production from a male-sterile female parent and a male parent is depicted in a general way in FIG. 1. The conditions required for the successful production of hybrid seeds by genetic means are as follows: 1) complete and stable male-sterility of the female parent, called the 'A-line' or 'Female line'; 2) complete and stable male-fertility restoration by the male parent, called the 'R-line', or 'Male line'; and 3) easy propagation of the female A-line by a male-fertile maintainer line, called the 'B-line' or 'Maintainer line'. The F$_1$ hybrid seeds produced are all male-fertile. The female A-line is propagated either by pollination with the maintainer B-line, by selfing the maintainer B-line, or by both methods and the maintainer B-line is itself maintained by selfing, and the desired proportion of male-fertile plants among the progeny of the selfed maintainer is kept each generation by the use of a selectable marker(s) characterizing the maintainer.

An example of such a scheme for the production of hybrid common or durum wheat is shown more specifically in FIGS. 13, 14 and 15. A cultivar, herein designated cv. 'One', equipped with genes for male-sterility, i.e. homozygous for one of the male-sterility recessive mutant alleles (ms-B1ms-B1) on the short arm of chromosome 4B and homozygous for the dominant pollen-killer allele (Ki-B1) on the long arm of 6B, is used as the male-sterile female A-line. Three such male-sterility alleles have been described (review in Wilson and Driscoll, 1983). These alleles are 'Pugsley' (Pugsley & Oram, 1959—spontaneous appearance; ms-B1-a), 'Probus' (Fossati & Ingold, 1970—induced by X rays; ms-B1-b) and 'Cornerstone' (Driscoll, 1977—induced by gamma-irradiation; ms-B1-c). The alleles ms-B1-b and ms-B1-c are terminal deletions. Several additional mutant alleles were previously induced by us either by gamma-irradiation or by treatment with ethyl methanesulfonate (EMS). The EMS treated mutants can be distinguished from the various deletions of the Ms-B1 locus by the presence in these mutants of a terminal C-band on 4BS. DNA markers such as Xpsr921 that are located on the distal region of 4BS, are absent in ms-B1-c and in several of our gamma-irradiated mutants (and possibly also in ms-B1-b), i.e., it is located in the deleted segment and its absence can mark homozygosity for the deletion. The Ki-B1 allele, present En the cultivar Chinese Spring, is located on the long arm of chromosome 6B about 50 cM from the centromere (Loegering & Sears, 1963). DNA markers such as Xpsr915 are tightly linked to the ki-B1 allele. When the male-sterile female line is maintained by a maintainer that carries the engineered chromosome of the EC-HR type the female line should be also homozygous for the recessive chlorotoluron susceptibility allele su-B1. This allele, present in the common wheat cultivar Chinese Spring and in several other genotypes of tetraploid wheat, is located on the long arm of chromosome 6B, about 0.5 cM from the centromere (Snape et al, 1991).

Figure 2A:
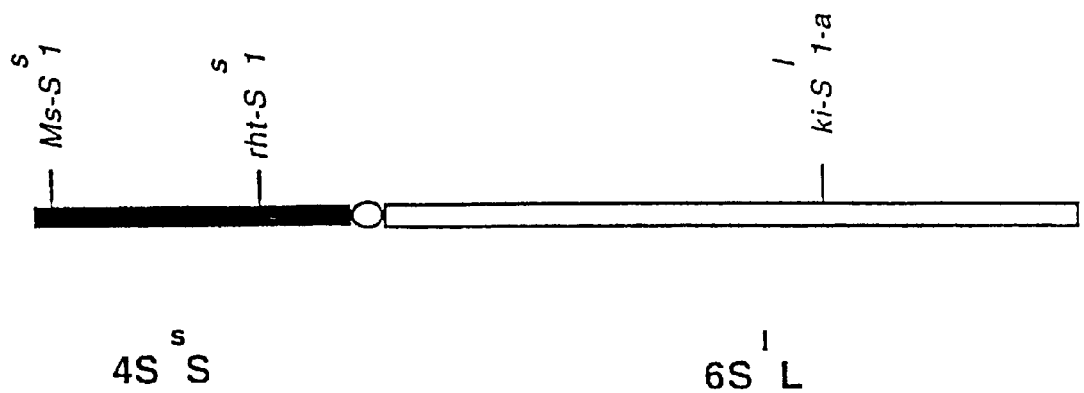
FIGS. 2a–2d depict schematic drawings of the engineered chromosomes EC-H1 (2a), EC-HR1 (2b) and the recombinant engineered chromosomes REC-H1 (2c) and REC-HR1 (2d).

The maintainer B-line is of the same cultivar as the A-line, i.e., cv. 'One', is homozygous for the same ms-B1 and Ki-B1 alleles present in the A-line but has an additional alien engineered chromosome of the EC-H type (FIG. 2a) consisting of 4S$^s$S of *Aegilops searsii*, that carries the dominant male-fertility allele Ms-S$^s$1 and the dominant or semi-dominant rht-S$^s$1 allele that confers taller plants, and of 6S$^l$L of *Ae. longissima* that carries the recessive pollen-killer allele ki-S$^l$1-a, rendering pollen-grains carrying it amenable to killing by the Ki-B1 allele of common or durum wheat. Because of the presence of ki-S$^l$1-a, the alien engineered chromosome is not transmitted through the pollen grains. Hence, pollinating the male-sterile female line (A-line) by the maintainer (B-line) yields progeny, all of which are identical to the female line and are male-sterile (FIG. 13a). On the other hand, self pollination of the maintainer line yields 80% male-sterile and 20% male-fertile offspring (FIG. 13a). Due to the presence of the rht-S$^s$1 allele in the engineered chromosome, the male-fertile offspring of the maintainer are taller by 6–8 cm than the male-sterile offspring. This height difference facilitates the selective harvest, by combine harvester, of the male-fertile offspring, thus keeping constant, in each generation, the proportion of the male-fertile plants among the progeny of the selfed maintainer line.

Figure 2B:
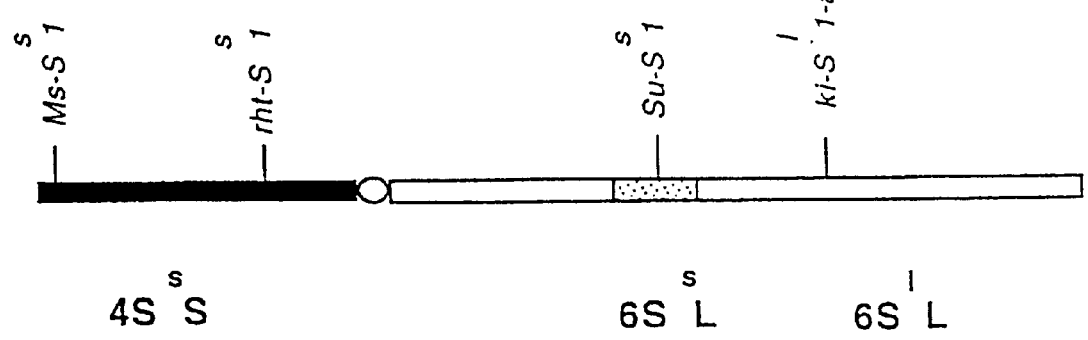

An alternative maintainer B-line is of the same cultivar as the A-line, i.e., cv. 'One', is homozygous for the same ms-B1, su-B1 and Ki-B1 alleles present in the A-line but has an additional alien engineered chromosome of the EC-HR type (FIG. 2b) consisting of 4S$^s$S of *Aegilops searsii*, that carries the dominant male-fertility allele Ms-S$^s$1 and the dominant or semi-dominant rht-S$^s$1 allele, and of 6S$^l$S of *Aegilops longissima* that carries the dominant chlorotoluron resistance allele Su-S$^s$1 that was found to confer excellent resistance to this herbicide and was transferred from 6S$^s$L of *Ae. searsii* to the 6S$^l$L of *Ae. longissima*, and the recessive pollen-killer allele ki-S$^l$1-a, rendering pollen-grains carrying it amenable to killing by the Ki-B1 allele of common or durum wheat. Because of the presence of ki-S$^l$1-a, the alien engineered chromosome is not transmitted through the pollen grains. Hence, pollinating the male-sterile female line (A-line) by the maintainer (B-line) yields progeny, all of which are identical to the female line and are male-sterile (FIG. 14a). On the other hand, self pollination of the maintainer line yields 80% male-sterile and 20% male-fertile offspring (FIG. 14a). Due to the presence of the Su-S$^s$1 allele in the engineered chromosome, the male-fertile offspring of the maintainer are resistant to the herbicide chlorotoluron and to other phenylurea derivatives, whereas the male-sterile offspring are susceptible to them. This resistance facilitates, in each generation, the killing of all the susceptible seedlings, lacking the engineered chromosome in the progeny of the selfed maintainer line.

Figure 2C:
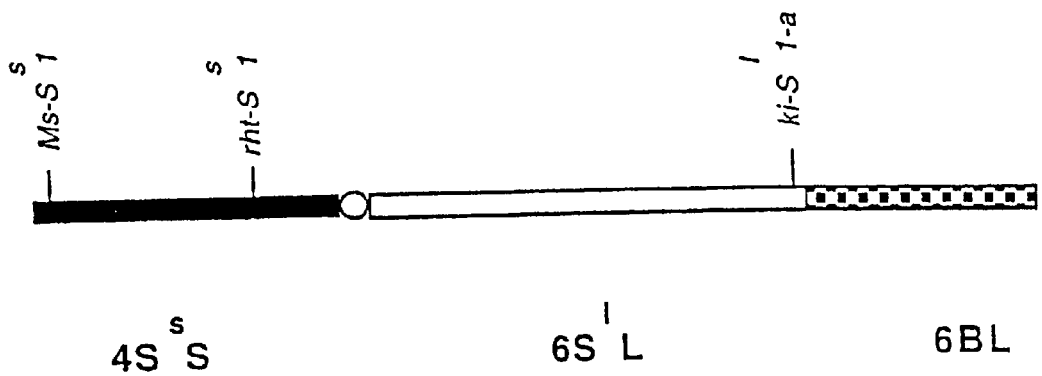

Alternatively, the maintainer line may be the same as the A-line but monosomic for chromosome 6B, i.e., is homozygous for ms-B1 and hemizygous for Ki-B1, and has one dose of the recombinant engineered chromosome of the REC-H type (FIG. 2c) consisting of 4S$^s$S of *Aegilops searsii*, that carries the dominant alleles Ms-S$^s$1 and rht-S$^s$1, of 6S$^l$L of *Ae. longissima* that carries the recessive pollen-killer allele ki-S$^l$1-a, rendering pollen-grains carrying it amenable to killing by the Ki-B1 allele of common and durum wheat, and of a distal region of chromosome arm 6BL, that pairs regularly with its homologous region of the native single 6B chromosome. The regular pairing of the recombinant engineered chromosome REC-H with 6B ensures its even segregation and consequently, its inclusion in 50% of the gametes. Because of the presence of ki-S$^l$1-a, the recombinant engineered chromosome is not transmitted through the pollen-grains. Hence, pollinating the male-sterile female line (A-line) by the recombinant maintainer yields progeny, all of which are identical to the female line and are male-sterile. On the other hand, self pollination of the recombinant maintainer line yields ½ male-sterile and ½ male-fertile offspring (FIG. 13b).

The male-fertile offspring, having the rht-S$^s$1 allele, are taller by 6–8 cm than the male-sterile offspring and therefore can be harvested separately. This keeps constant, in each generation, the proportion of the male-fertile plants among the progeny of the selfed maintainer.

Figure 2D:
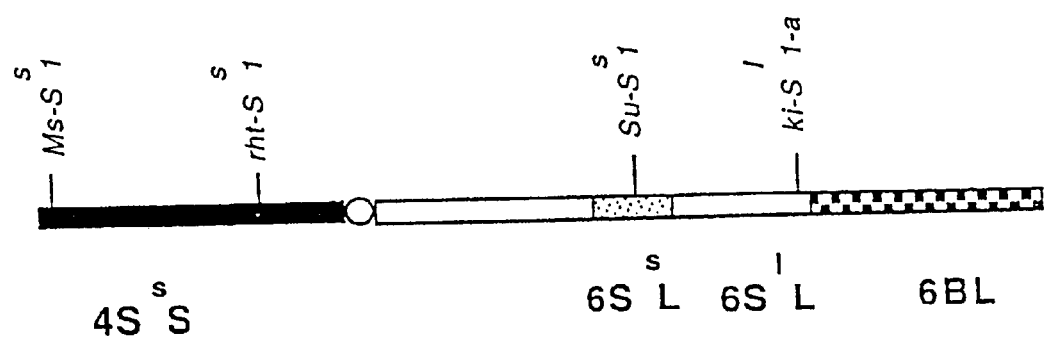
Figure 3A:
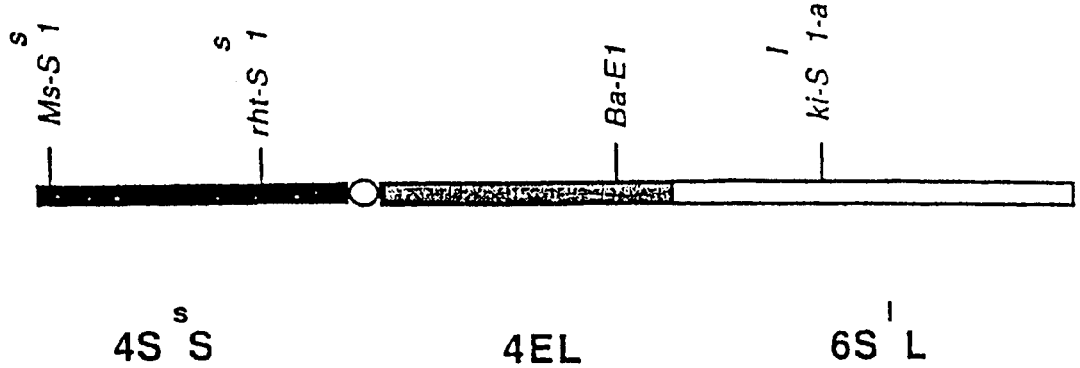
FIGS. 3a–3b depict schematic drawings of the improved engineered chromosome IEC-HC1 (3a) and the improved recombinant engineered chromosome IREC-HC1 (3b).
Figure 3B:
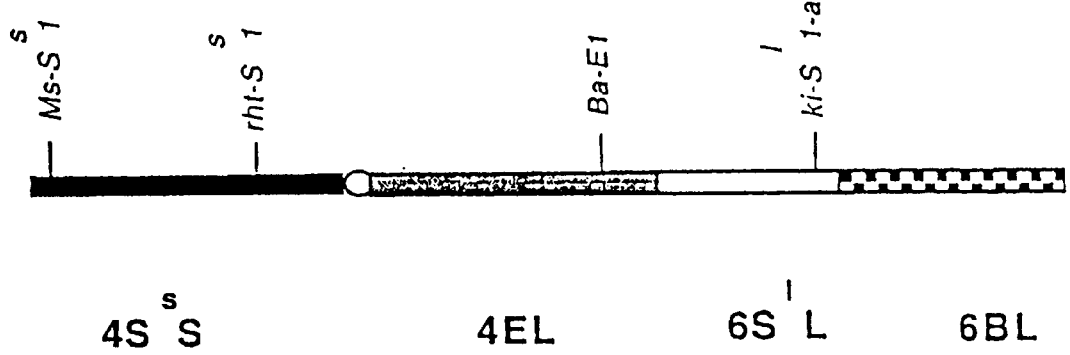
Figure 4A:
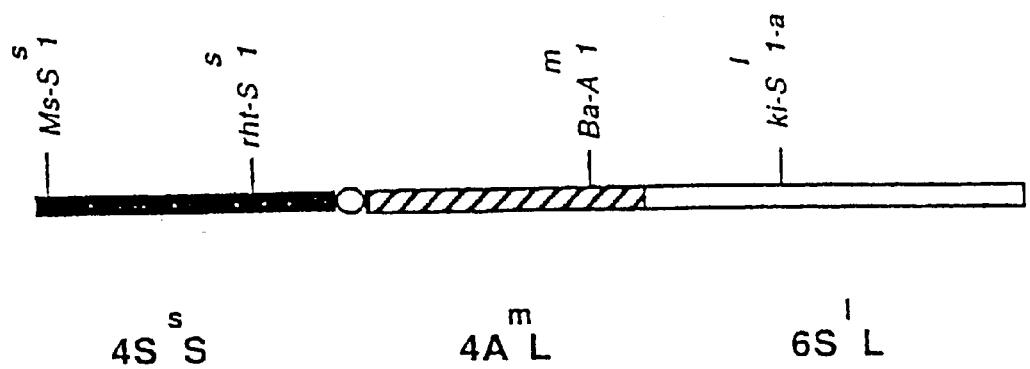
FIGS. 4a–4b depict schematic drawings of the improved engineered chromosome IEC-HC2 (4a) and the improved recombinant engineered chromosome IREC-HC2 (4b).
Figure 4B:
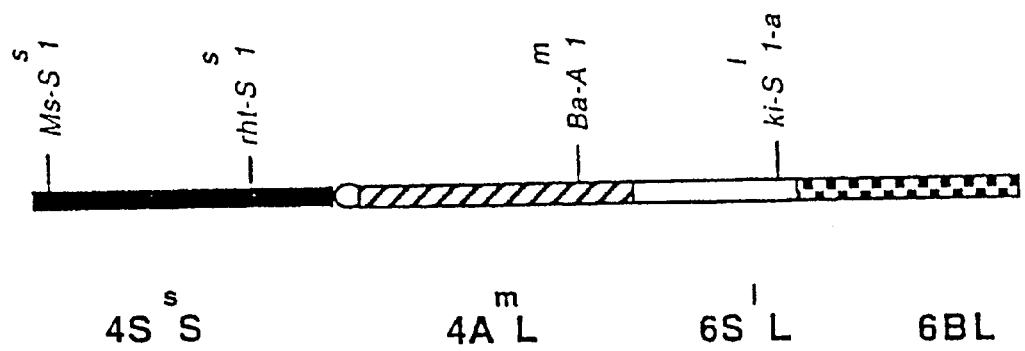
Figure 5A:
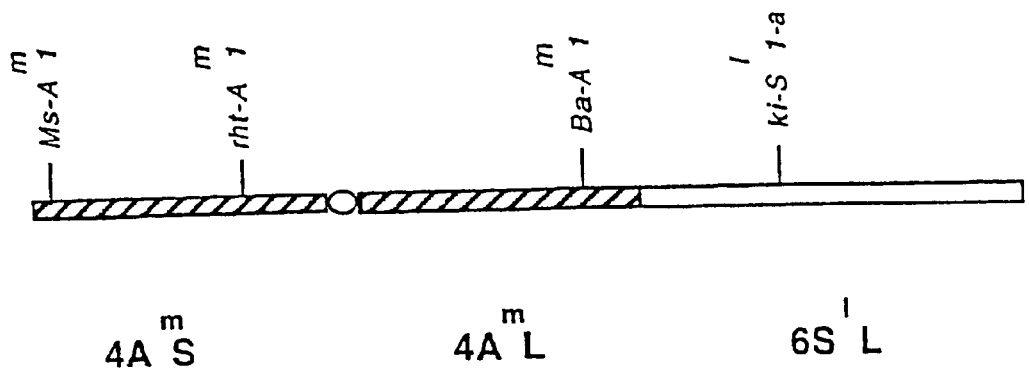
FIGS. 5a–5b depict schematic drawings of the improved engineered chromosome IEC-HC3 (5a) and the improved recombinant engineered chromosome IREC-HC3 (5b).
Figure 5B:
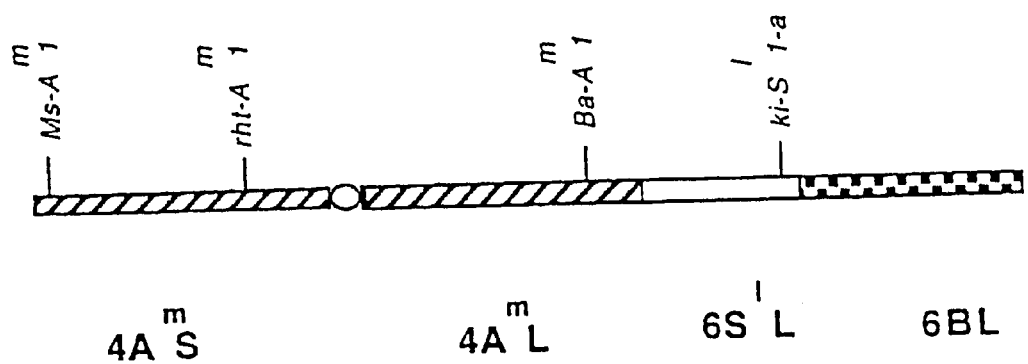
Figure 6:
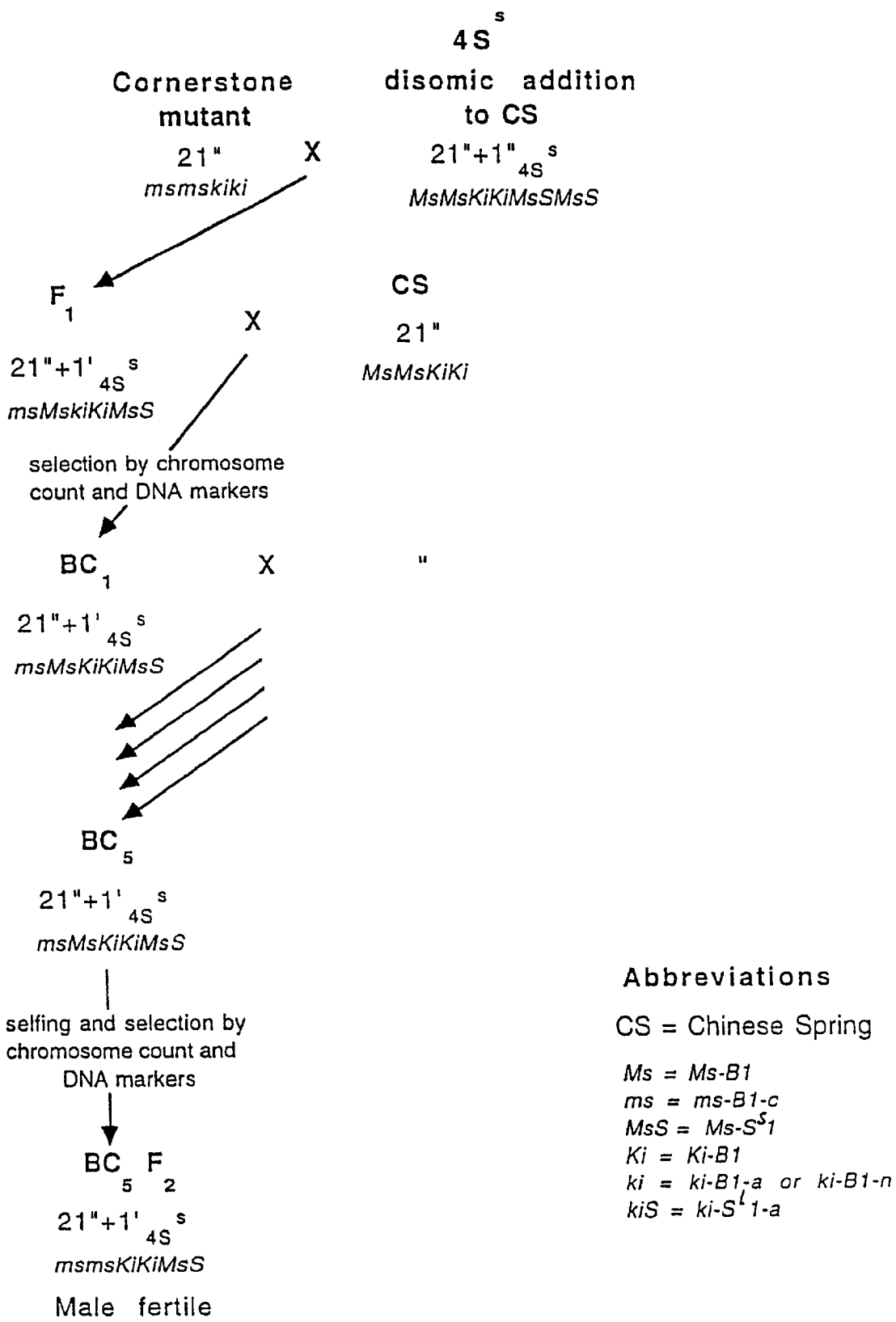
FIG. 6 depicts a schematic procedure for transferring the recessive male-sterility allele ms-B1-c from the Cornerstone mutant into the $4S^s$ monosomic addition line of the common wheat cultivar Chinese Spring (CS).

Another maintainer line may be the same as the A-line but monosomic for chromosome 6B, i.e., is homozygous for ms-B1 and hemizygous for su-B1 and Ki-B1, and has one dose of the recombinant engineered chromosome of the REC-HR type (FIG. 2d) consisting of 4S$^s$S of *Aegilops searsii*, that carries the dominant alleles ms-S$^s$1 and rht-S$^s$1, and of 6S$^l$L of *Aegilops longissima* that carries the dominant chlorotoluron resistance allele Su-S$^s$1 allele that was transferred from 6S$^s$L of *Ae. searsii* to 6S$^l$L of *Ae. longissima* and the the recessive pollen-killer allele ki-S$^l$1-a, rendering pollen-grains carrying it amenable to killing by the Ki-B1 allele of common and durum wheat, and of a distal region of chromosome arm 6BL, that pairs regularly with its homologous region of the native single 6B chromosome. The regular pairing of the recombinant engineered chromosome REC-HR with 6B ensures its even segregation and consequently, its inclusion in 50% of the gametes. Because of the presence of ki-S$^l$1-a, the recombinant engineered chromosome is not transmitted through the pollen-grains. Hence, pollinating the male-sterile female line (A-line) by the recombinant maintainer yields progeny, all of which are identical to the female line and are male-sterile. On the other hand, self pollination of the recombinant maintainer line yields ½ male-sterile and ½ male-fertile offspring (FIG. 14b).

The male-fertile offspring, having the Su-S$^s$1 allele, are resistant to chlorotoluron. Applying this herbicide to a maintainer plot will kill all the male-sterile offspring that lack the engineered chromosome, leaving only the male-fertile maintainer plants.

Figure 15A:
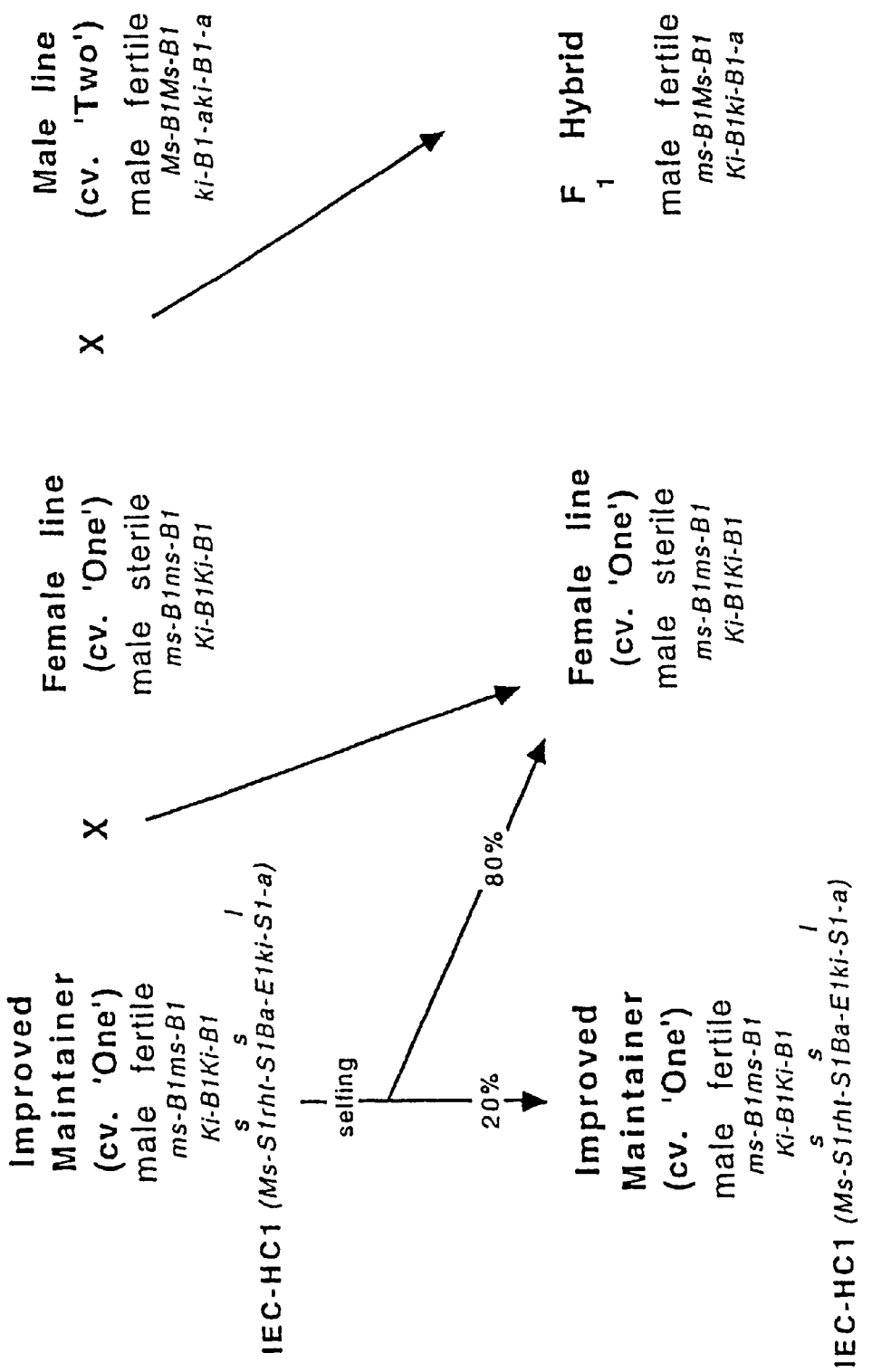

Other maintainers contain an improved engineered chromosome of the IEC-HC type (FIGS. 3a, 4a and 5a) carrying, in addition to the Ms, rht and ki-S$^l$1-a alleles, as additional selectable marker, the blue aleurone (Ba) allele, that confers blue coloring of the seeds. Three types of such improved engineered chromosomes are being produced: (1) IEC-HC1, consisting of 4S$^s$S (carrying the Ms-S$^s$1 and rht-S$^s$1 alleles), 4EL (carrying the Ba-E1 allele), and 6S$^l$L (carrying the ki-S$^l$1-a); (2) IEC-HC2, consisting of 4S$^s$S (carrying the Ms-S$^s$1 and rht-S$^s$1 alleles), 4A$^m$L (carrying the Ba-A$^m$1 allele), and 6S$^l$L (carrying the ki-S$^l$1-a); (3) IEC-HC3, consisting of 4A$^m$S (carrying the Ms-A$^m$1 and rht-A$^m$1 alleles), 4A$^m$L (carrying the Ba-A$^m$1 allele), and 6S$^l$L (carrying the ki-S$^l$1-a). Because of the presence of ki-S$^l$1-a, the improved engineered chromosomes are not transmitted through the pollen grains. Hence, pollinating the male-sterile female line (A-line) by the improved maintainer (B-line) yields progeny, all of which are identical to the female line and are male-sterile (FIG. 15a). On the other hand, self pollination of the maintainer line yields 80% male-sterile and 20% male-fertile offspring (FIG. 15a). Due to the presence of the Ba allele, it is feasible to separate, by sorting apparatus, the red/white seeds, which seeds when grown, develop into male-sterile plants, from the blue seeds, which seeds when grown, develop into male-fertile plants. Thus, planting, in each, generation, only the blue seeds, assures that all the maintainer plants will be male-fertile.

The possibility to separate the red/white seeds of the maintainer, which when grown, develop into male-sterile plant (A-line) from the blue seeds, which when grown, develop into the male-fertile line (B-line) (FIGS. 1b and 15a), provides an alternative and preferred way to obtain the seeds of the male-sterile female line directly from the progeny of the selfed maintainer. In this way the production cost of the female seeds is considerably reduced.

Other maintainers contain an improved recombinant engineered chromosome of the IREC-HC type (FIGS. 3b, 4b and 5b) carrying on the long arm of the improved recombinant engineered chromosome a terminal segment of chromosome arm 6BL that pairs regularly with the native chromosome 6B which exists as a monosomic addition in this maintainer. This pairing ensures regular segregation of the improved recombinant engineered chromosomes during meiosis and consequently their inclusion in 50% of the gametes. Because of the presence of the ki-S$^l$1-a, the IRECs are not transmitted through the pollen grains. Hence, pollinating the male-sterile female line (A-line) by the improved recombinant maintainer (B-line) yields progeny, all of which are identical to the female line and are male-sterile (FIG. 15b). On the other hand, self pollination of the recombinant maintainer line yields 50% male-sterile and 50% male-fertile offspring (FIG. 15b). Due to the presence of the Ba allele, it is feasible to separate, by sorting apparatus, the red/white seeds from the blue seeds. Thus, planting, in each generation, only the blue seeds, assures that all the maintainer plants will be male-fertile.

As in many other grasses, also in wheat, the centromere of a univalent (unpaired) chromosome occasionally undergoes a transverse division (misdivision) at meiosis rather than the normal longitudinal one, resulting in the breakage of the univalent into two telocentrics or isochromosomes. The frequency of this event in monosomic or monosomic addition plants, i.e. having a univalent chromosome at meiosis, is usually low (several percentages). Since the EC of the EC-H, EC-HR and IEC-HC types exists in the maintainer line as a monosomic addition and as such it remains unpaired at meiosis, the selfed progeny of the maintainer may contain plants having only one arm of the EC. Plants having the long arm, ECL (carrying Ba and ki-S$^l$1-a alleles) will be male-sterile. On the other hand, plants having the short arm, ECS (carrying the Ms and the rht alleles) will be male-fertile. Since plants with ECS do not carry the ki-S$^l$1-a allele, male gametes having the ECS may be functional and either by pollinating female plants or by selfing, and thus, contaminate the female line. In the case of EC-HR, plants having the short arm and lacking the long arm of the EC are susceptible to chlorotoluron and can be selected against by the application of this herbicide to the progeny of the selfed maintainer. In the case of IEC-HC, plants having the short arm and lacking the long arm of the EC produce red/white seeds that can be separated by a sorting apparatus from the blue seeds in the progeny of the selfed maintainer.

On the other hand, the recombinant engineered chromosome of both the REC-H and the IREC-HC types, pairs regularly at meiosis with the native 6B chromosome, and consequently its centromere undergoes only a longitudinal division at second meiotic anaphase; telocentrics are not formed and the female line is not contaminated with male-fertile plants.

To increase the proportion of seeds in the progeny of the selfed improved recombinant maintainer, said seeds, when grown, developing into male-sterile plants, it is necessary to self the improved recombinant maintainer and grow the progeny seeds another season. In this way (as depicted in FIG. 15b) the amount of desired seeds may be above 70%. In the improved recombinant maintainer with the IREC-HC type it is possible to carry out two-step selection: to harvest the tall plants (carrying the IREC-HC with the rht allele) first. The short plants will be harvested in a second harvest and their seeds will be separated by seed sorter on the basis of their color. The red/white seeds lack the IREC-HC and, when grown, develop into the male-sterile female line.

The male parent (R-line, cv. 'Two') is any normal common or durum wheat cultivar, which by its nature is homozygous for the male-fertility Ms-B1 allele, and homozygous either for the dominant Ki-B1 allele or for one of the recessive ki-B1 alleles (ki-B1-a or ki-B1-n).

Thus, by the scheme shown in FIGS. 13a–b, 14a–b and 15a–b, hybrid seeds of common or durum wheat are rapidly and efficiently produced as the F$_1$ progeny, all of which are heterozygous for the male-sterility alleles (Ms-B1ms-B1) and therefore, are male-fertile. So far, all cultivars that were used as male parents were able to fully restore the male fertility of the F$_1$ hybrid.

Example 2

Testing the Expression of Male-fertility, Brought About by One Dose of the Male-fertility Allele Ms-S$^s$1 of *Aegilops searsii* in ms-B1ms-B1 Genotype of Common Wheat In order to test the feasibility of the above hybrid production system and maintenance of the male-sterile female parent (A-line), it was first necessary to produce an alien monosomic addition line in which chromosome 4S$^s$ of *Aegilops searsii* was added to the full complement of common wheat, homozygous for the male-sterility allele ms-B1-c. This was carried out by crossing the disomic 4S$^s$ addition line (derived from crosses of *Aegilops searsii* acc. TE-10 with the common tall wheat cultivar Chinese Spring and kindly provided by Prof. G. Hart, Soil and Crop Science, Texas A & M University, College Station, Tex.) which is homozygous for Ms-B1, rht1 and rht2 and carries two doses of Ms-S$^s$1 and rht-S1, with the ms-B1-cms-B1-c Rht1Rht1rht2rht2 male-sterile genotype of the semi-dwarf common wheat cv. Gamenia (kindly provided by Dr. M. MacKay, curator of the Australian Winter Cereal Collection, RRM 944, Calala Lane, Tamworth, NSW 2340, Australia). The resultant F$_1$ plants were all heterozygous Ms-B1ms-B1-c and carried one additional chromosome of 4S$^s$ with the Ms-S$^s$1 allele. These plants were selfed and F$_2$ plants homozygous for ms-B1-c (as was indicated by the phenotype of the DNA markers) were selected. All euploid homozygous ms-B1-cms-B1-c plants were, as expected, male-sterile, but those homozygous that had an additional 4S$^s$ chromosome carrying Ms-S$^s$1 were all male-fertile, indicating the complete dominance of Ms-S$^s$1 over two doses of ms-B1-c.

Example 3

Testing the Height Difference Between Common Wheat Plants Homozygous for the Reduced Height Allele Rht1 or Rht2 and Isogenic Plants but Having Chromosome 4S$^s$ of *Ae. searsii* that Carries rht-S$^s$1 Allele

*Aegilops searsii* is a short-stature plant. Nevertheless it contains the rht-S$^s$1 allele that promotes plant height. This allele is homoeoallelic to the rht alleles of common wheat that are located on the short arm of chromosomes of group 4, about 15 cM from the centromere (McIntosh, 1993). The rht-S$^s$1 is linked to the male-fertility Ms-S$^s$1 allele which is located on the terminal region of 4S$^s$S. Since chromosome 4S$^s$ does not pair with its wheat homoeologues in normal common wheat background, the rht-S$^s$1 and the Ms-S$^s$1 alleles are permanently linked in the different types of the alien engineered chromosomes. The existence of the rht-S$^s$1 allele on the engineered chromosome may promote taller plants and hence, may serve as a selectable marker allele that facilitates the differential harvest of the male fertile offspring of the maintainer, i.e., those carrying the engineered chromosome. This will keep constant, in each generation, the proportion of the male-fertile plants in the progeny of the selfed maintainer.

To test the effect of rht-S$^s$1 on plant height of common wheat, homozygous for one of the Rht alleles, we crossed the disomic 4S$^s$ addition line The resultant F$_1$ plants were all heterozygous for one of the Rht alleles and carried one additional chromosome of 4S$^s$ with the rht-S$^s$1 allele. These, plants were selfed and F$_2$ plants either homozygous or heterozygous for the Rht (as was indicated by their height) were selected. All euploid plants were shorter (on the average by 6–8 cm) from those that had the additional 4S$^s$ chromosome carrying the rht-S$^s$1 allele, indicating that the presence of rht-S$^s$1 in semi-dwarf common wheat genotype promotes taller plant height which can be used as a selectable marker.

Example 4

Testing the Effect of Chlorotoluron on Common Wheat Plants Homozygous for the Chlorotoluron Susceptibility Allele su-B1 and on Isogenic Plants that Have Also the Engineered Chromosome Carrying the Dominant Resistance Allele Su-S$^s$1

Different cultivars of common wheat show different reaction to the herbicide chlorotoluron and to other phenyl derivatives of urea; several cultivars carrying the dominant allele Su-B1 (e.g., Cappelle Desprez) are resistant while others carrying the recessive allele su-B1 (e.g., Chinese Spring) are susceptible (Snape et al, 1991). The gene is located on the long arm of chromosome 6B (6BL) about 0.5 cM from the centromere. Different lines of diploid *Aegilops species*, whose genome is closely related to the B genome of wheat, also exhibit different reaction to chlorotoluron: while most lines are susceptible to the herbicide, one line of *Ae. searsii* is resistant to the chemical. Since chromosome 6S$^s$L of *Ae. searsii* pairs almost regularly with 6S$^l$L of *Ae. longissima*, it is possible to transfer the resistance allele to the 6S$^l$L arm of the engineered chromosome EC-H (FIGS. 8a,b), thus producing the engineered chromosome of the EC-HR type. Since chromosome arms 4S$^s$S and 6S$^s$L do not pair with their wheat homoeologues in a normal common wheat background, the Su-S$^s$1 allele is permanently linked to the other alleles of the engineered chromosome, i.e., Ms-S$^s$1, rht-S$^s$1 and Ki-S$^l$1-a. The presence of the chlorotoluron resistance allele on the engineered chromosome facilitates the selective killing, in each generation, of the male-sterile plants that lack the engineered chromosome while unaffecting the male-fertile maintainer plants (with the engineered chromosome) in the progeny of the selfed maintainer. This will assure, that in each generation, only the male-fertile offspring of the selfed maintainer, will grow.

To test the effect of chlorotoluron on the various genotypes we sprayed this herbicide at a rate which is double of the recommended at commercial fields on plants of common wheat homozygous for the herbicide susceptibility allele su-B1 and the line of *Ae. searsii* carrying the chlorotoluron resistance allele Su-S$^s$1. All plants carrying the recessive su-B1 allele died within 10–14 days from spraying while those carrying the dominant Su-S$^s$1 allele survived.

Example 5

The Effect of the Blue Aleurone on Seed Color and Separation Between Blue and Red/White Seeds Seed color of common or durum wheat is red or white; the red color results from the presence of a pigment in the testa. Several species related to common and durum wheat, e.g., *T. monococcum, A. elongatum, A. glaucum, A, tricophorum, A. junceum, Secale montanum, Secale cereale* and *Hordeum spontaneum*, contain lines with blue seeds. The blue pigment results from production of anthocyanins in the triploid aleurone layer of the endosperm (for review see Zeven, 1991). The blue pigment indicates the genotype of the aleurone, a phenomenon known as xenia, i.e., a red/white seeded plant pollinated with a blue aleurone plant produces blue seeds. The blue color is determined by the blue aleurone (Ba) allele (designation after Keppenne and Baenziger, 1990, in accordance with Dr. R. A. McIntosh, co-ordinator of gene symbol for wheat), located on the long arm of chromosome 4A$^m$ of *T. monococcum* or 4E of *E. pontica* (Zeven, 1991). The Ba locus in barley (designated Bl) is located on the long arm of chromosome 4H, 29 cM from the centromere (Grain Genes data base, ref: BCN-25-93). Hence, based on the gene syntheny existing among the Triticeae species, it is assumed that, also in *T. monococcum* and *E. pontica* this gene is located at about the same distance from the centromere. The seeds of monosomic addition lines of 4A$^m$ or 4E to common wheat are blue indicating the complete dominance of the Ba allele. This allele has a dosage effect which is revealed by the intensity of the color: three doses of Ba give a dark blue seed, two doses (resulting from transmission of the allele through the female gamete)

give a medium-blue seed, while one dose (resulting from transmission of the allele through the male gamete) gives a light-blue seed. The environment in which the plants were grown, e.g., dry and warm conditions during grain-filling period, as well as the plant's genetic background, may reduce the expression of the Ba allele, causing some mis-classification of seeds with one dose of Ba. Seeds with two or three doses of Ba have been always classified correctly. The Ba allele, either with Ba-E1 or Ba-A$^m$1, is translocated to the alien recombinant engineered chromosome that ordinarily does not pair with its wheat homoeologues. Hence the Ba allele, being permanently linked to the Ms-S$^s$1 and rht-S$^s$1 alleles or to the Ms-A$^m$1 and rht-A$^m$1 alleles as well as to the ki-S$^l$1-a allele can be used as an excellent selectable marker. The blue seeds can be separated from the red/white seeds by the use of a sorting apparatus (such as Sortex 5000). It can be used for separation of a large quantities of seeds and hence can be used for commercial applications.

Example 6

Testing the Killing of ki-S$^l$1-a—Carrying Pollen by the Dominant Pollen-killer Allele Ki-B1 of Common wheat Loegering and Sears (1963) found that chromosome arm 6BL of the common wheat cultivar Chinese Spring carries a dominant pollen-killer allele that kills pollen-grains having the recessive ki allele (=ki-B1-a) of cv. Timstein. In crossing several common wheat cultivars with the two tester lines, Chinese Spring and Timstein, they found, at least, three alleles in the pollen-killer locus: the dominant Ki (=Ki-B1), the recessive ki (=ki-B1-a) and the neutral (=ki-B1-n) alleles.

Since the dominant allele kills only pollen and not eggs, it can be used to block the transmission of pollen carrying the alien dominant male-sterility allele Ms-S$^s$1. This requires the establishment of a permanent linkage between the Ms-S$^s$1 and the ki-B1-a alleles. Such linkage can be achieved by constructing an alien chromosome that carries these two alleles, and which does not ordinarily pair with its wheat homoeologous chromosomes. A prerequisite condition for the construction of such an engineered chromosome is the availability of a recessive pollen-killer allele in one of the wild relatives of wheat.

While producing a series of Ae. longissima addition lines in the background of Chinese Spring, the present inventors noticed that chromosome 6 of Ae. longissima (6S$^l$) was transmitted through the pollen only in plant deficient for chromosome 6B. Analysis of pollen abortion, in pollen stained with Alexander reagent (Stain Technology, 44: 117), in a 6S$^l$ monosomic addition line, showed about 20% aborted pollen-grains, presumably those carrying the 6S$^l$ chromosome, while in a 6S$^l$S monotelosomic addition line only 2–3% aborted pollen was noticed. No disomic addition plants were found among the progeny of selfed monosomic addition plants. This indicates that while the transmission of 6S$^l$ through the egg is not affected, the transmission of 6S$^l$ through the pollen assumed that chromosome 6S$^l$ of several accessions of Ae. longissima carries a recessive pollen-killer allele, designated herein as ki-S$^l$1-a, which pollen-grains carrying it are amenable to killing by the Ki-B1 allele of common wheat.

Example 7

Construction of the Engineered Chromosome EC-H1 Comprising 4S$^s$S that Carries the Ms-S$^s$1 and rht-S$^s$1 Alleles and 6S$^l$L that Carries the ki-S$^l$1-a Allele A chromosome, either native or alien, that exists in common wheat in a single dose, as in monosomic or monosomic-addition lines, may undergo centromeric mis-division at meiosis, in low frequency, i.e. a transverse rather than a longitudinal division of the centromere, resulting in the production of one or two stable telocentric chromosomes. If two non-homologous chromosomes existing each in a single dose, undergo simultaneously mis-division, the resultant telocentrics of the different chromosomes may fuse to yield a translocated chromosome (Sears, 1972). The frequency of this centric fusion varies from less than 1% (Sears, 1972) to more than 23% (Lukaszewski, 1993).

We have utilized this phenomenon in the construction of the engineered chromosome 4S$^s$S/6S$^l$L. Pollinating a monosomic 6S$^l$ addition line, carrying ki-S$^l$1-a, with a 4S$^s$ disomic addition line, carrying Ms-S$^s$1 and rht-S$^s$1, resulted in F$_1$ progeny having chromosome 4S$^s$ and ¼ of which have also chromosome 6S$^l$, i.e., double monosomic addition line. The presence of 4S$^s$ and 6S$^l$ in these plants was confirmed by the use of the DNA probes PSR921 and PSR915, respectively.

About 2000 F$_2$ plants were obtained and screened first by chromosome counting. The monosomic additions, namely those seedlings that had 2n=43, were subjected to a further screening by DNA markers to eliminate those having either 4S$^s$L or 6S$^l$S. Several plants were found to possess 4S$^s$S and 6S$^l$L. C-banding analysis confirmed the presence of the desired centric fusion.

As expected, this chromosome is not transmitted through the pollen-grains and all pollinations of euploid plants by those carrying the engineered chromosome as a monosomic addition line, yielded only euploid progeny, while selfing of the monosomic addition line yielded about 20% seedlings with 43 chromosomes.

Example 8

Construction of the Engineered Chromosome EC-HR1 Comprising 4S$^L$S that Carries the Ms-S$^s$1 and rht-S$^s$1 Alleles and 6S$^l$L that Carries the Su-S$^s$1 ki-S$^l$1-a Alleles To construct the engineered chromosome EC-HR1, the dominant chlorotoluron resistance allele Su-S$^s$1 is transferred from chromosome arm 6S$^s$L of a selected line of Ae. searsii into the 6S$^l$L arm of the engineered chromosome EC-H1. This is achieved by crossing a male-fertile female parent derived from the male-fertile maintainer line in the common wheat cultivar Chinese Spring. This female parent is homozygous for the ms-B1, su-B1 and Ki-B1 alleles and has, as a monosomic addition, the engineered chromosome EC-H1 (4S$^s$S/6S$^l$L) carrying on its short arm the Ms-S$^s$1 and rht-S$^s$1 alleles and on its long arm the su-S1ki-S$^l$1-a alleles, with a line of the diploid species Ae. searsii carrying the chlorotoluron resistance allele on the long arm of chromosome 6S$^s$, i.e., on 6S$^s$L, as well as the Ms-S$^s$1 and rht-S$^s$1 alleles on 4S$^s$S. About 20% of the F$_1$ progeny have the engineered chromosome EC-H1 and therefore contain 2n=29 chromosomes and can be distinguished from the other F$_1$ plants having 2n=28. The F$_1$ plants with the engineered chromosome exhibit 26 univalents (26') and a trivalent (1''') at first meiotic metaphase due to the pairing of the engineered chromosome (4S$^s$S/6S$^l$L) with chromosome arms 4S$^s$S and 6S$^s$L of Ae. searsii. While pairing of 4S$^s$ of the EC with 4S$^s$S of Ae. searsii does not change the allelic constitution of the short arm of the EC, that between 6S$^l$L and 6S$^s$L, yields, after crossing over between the centromere and the Su locus and a second crossing over between the Su and the ki loci, the desired EC-HR1 chromosome. Pollinating the 2n=29 F$_1$ plants once or twice with Chinese Spring, homozygous for su-B1 yields plants with 2n=43 (21"+1') containing the desired engineered chromosome EC-HR1 as a monosomic addition. Applying chlorotoluron to the progeny of the selfed monosomics addition plants kills all plants with 2n=42 (lacking the EC-HR1 and therefore the chlorotoluron resistance allele) and leaving unaffected only those plants with 2n=43, i.e., those carrying the EC-HR1.

Example 9

Construction by Centric Fusion of the Alien Chromosomes $4S^sS/4EL$ and $4S^sS/4A^mL$ We have also utilized the phenomenon of centric fusion to produce alien chromosomes with constitution of $4S^sS/4EL$ and $4S^sS/4A^mL$. Pollinating a 4E monosomic addition line to common wheat with heterozygous Ms-B1ms-B1Ki-B1Ki-B1 and carrying the Ba-E1 allele with $4S^s$ disomic addition line homozygous ms-B1ms-B1Ki-B1Ki-B1 and carrying Ms-$S^s$1 and rht-$S^s$1, resulted in $F_1$ progeny having chromosome $4S^s$ and ¼ of which have also chromosome 4E, i.e., double monosomic addition. The presence of 4E and $4S^s$ in these plants was confirmed by the blue seeds and by DNA markers, respectively. Blue $F_2$ seeds (on $F_1$ plants) were selected, germinated and the desired plants were selected by chromosome count. The monosomic additions (2n=43) were subjected to further screening by DNA markers to eliminate those having chromosome arms either $4S^sL$ or 4ES. Several plants were found to posses $4S^sS$ and 4EL. C-banding analysis confirmed the presence of the desired centric fusion. In the production of $4S^sS/4A^mL$ we pollinated $4S^s$ monosomic addition by disomic (4B) $4A^m$ substitution line, and selected in the $F_1$ the triple monosomic combination: monosomic 4B, and double monosomic addition $4S^s$ and $4A^m$. These selected $F_1$ plants were selfed to produce the double monosomic addition $4S^s$ and $4A^m$. The presence of $4S^s$ and $4A^m$ in these plants was confirmed by the blue seed color and by DNA markers.

Blue $F_2$ seeds (on $F_1$ plants) were germinated and the seedlings were screened by chromosome count. The monosomic (2n=43) addition were selected and further screened by DNA markers to eliminate those having either $4S^sL$ or $4A^mS$. Several plants were found to posses the $4S^sS$ and $4A^mL$. C-banding analysis confirmed the presence of the desired centric fused chromosome.

Example 10

Production of the Recombinant Engineered Chromosome REC-H1 that Comprises $4S^sS$ (Carrying Ms-$S^s$1 and rht-$S^s$1, $6S^lL$ (Carrying ki-$S^l$1-a) and a Distal Region of 6BL The homoeologous chromosome arms 6BL and $65^lL$ do not pair in the presence of the Ph1 gene of common wheat. This dominant allele, located on the long arm of chromosome 5B, prevents pairing of homoeologous chromosomes while allowing regular pairing of homologues. A recessive mutation (ph1b) was induced in this locus by X-rays irradiation of the cultivar Chinese Spring which, in homozygous condition, does not suppress homoeologous pairing (Sears, 1977). This mutation was used to induce homoeologous pairing and recombination between 6BL and $6S^lL$.

A $6S^l$ (6B) disomic substitution line, in which a pair of chromosomes $6S^l$ of Ae. longissima replaced a pair of chromosomes 6B of the common wheat cv. Chinese Spring, was pollinated by the mutant line ph1bph1b. The $F_1$ hybrid, which is monosomic 6B—monosomic substitution $6S^l$ and heterozygous Ph1ph1b, was backcrossed as a female with the mutant line and double monosomics which are homozygous for ph1b were selected by the use of the DNA probe WPG90 (this probe was produced by us and can be obtained upon request). These selected $BC_1$ progeny plants were pollinated by a ditelosomic 6BS line to yield progeny, some of which are monotelosomic 6BS and monosomic for a recombinant chromosome $6S^l/6BL$, i.e., the recombinant chromosome comprises the short arm of $6S^l$, the proximal region of the long arm of $6S^l$ and the distal region of 6BL (the translocation breakpoint is distal to the locus of ki-$S^l$1-a on $6S^lL$). Selection for this translocated chromosome is carried out by the lack of pairing with 6BS and by the DNA markers located on $6S^lL$, distally to ki-$S^l$1-a and DNA markers on the distal region of 6BL. The selected genotype which is monotelosomic 6BS—monosomic $6S^l/6BL$ and homozygous for the dominant male-fertility allele Ms-B1, deficient for the Ki-B1 and hemizygous for ki-$S^l$1-a, was crossed as a male with a line carrying the engineered chromosome EC-H1 (see Example 6) as monosomic addition. Some of the progeny are triple monosomics, i.e., monosomics for 6B, $4S^sS/6S^lL$ and $6S^l/6BL$, and among these plants selection was made for heterozygous ms-B1-c Ms-B1 Ms-$S^s$1 and Ki-B1ki-$S^l$1-a, using DNA markers. In these selected progeny plants, pairing occurs in the proximal region of $6S^l$ of the two translocated chromosomes, resulting in the production of the recombinant engineered chromosome REC-H1 ($4S^sS/6S^lL/6BL$). Selfing of the selected progeny yielded, among others, double monosomic plants, having 6B and REC-H1 which are homozygous ms-B1-c ms-B1-c, hemizygous for Ki-B1 and for ki-$S^l$1-a.

Similarly, the selected monotelosomic 6BS-monosomic $6S^l/6BL$ was crossed as a male with lines carrying the improved engineered chromosome IEC-HC1, IEC-HC2 and IEC-HC3 as a monosomic addition Some of the progeny of each cross are triple monosomics, i.e., monosomic for 6B, $6S^l/6BL$ and for the improved engineered chromosome, and among these plants selection was carried out for heterozygous ms-B1Ms-B1 and Ki-B1Ki-B1, using DNA markers. In these selected plants, pairing occurs in the proximal region of $6S^l$ of the two translocated chromosomes, resulting in the production of the improved recombinant engineered chromosomes IREC-HC1 ($4S^sS/4EL/6S^lL/6BL$), IREC-HC2 ($4S^sS/4A^mL/6S^lL/6BL$) and IREC-HC3 ($4A^mS-4A^mL/6S^lL/6BL$). Selfing of the selected plants yielded, among others, double monosomic plants, having 6B and the improved recombinant engineered chromosome which are homozygous ms-B1-c ms-B1-c and hemizygous for Ki-B1 and for ki-$S^l$1-a.

Example 11

Production of the Recombinant Engineered Chromosome REC-HR1 that Comprises $4S^sS$ (carrying Ms-$S^s$1 and rht-$S^s$1), $6S^lL$ (Carrying Su-$S^s$1 and ki-$S^l$1-a) and a distal region of 6BL Production of REC-HR1 is done by crossing a monosomic addition line carrying the recombinant engineered chromosome REC-H1 with a line of Ae. searsii carrying the chlorotoluron resistance allele Su-$S^s$1, selecting $F_1$ plants with 25'+1''' and pollinating them with Chinese Spring (similarly to Example 8).

Example 12

Production of the Improved Engineered Chromosomes IEC-HC1 ($4S^sS/4EL/6S^lL$) IEC-HC2 ($4S^sS/4A^mL/6^lL$) and IEC-HC3 ($4A^mS-4A^mL/6S^lL$)

Production of these improved engineered chromosomes involves the production of a terminal translocation interchanging the distal region of 6S$^l$L (containing the ki-S$^l$1-a allele) with the homoeologous region of 4EL or 4A$^m$L of the centric-fused chromosomes. The translocation breakpoint is between the Ba allele of 4EL or 4A$^m$L (which is located about 30 cM from the centromere) and the ki-S$^l$1-a allele of 6S$^l$L (which is located about 50 cM from the centromere).

Terminal translocations are induced on several occasions by the use of X-ray or thermal neutron irradiation of seeds or pollen grains (for review see Keppenne and Baenziger, 1990; Sharma and Knott, 1966). The thermal neutrons are considerably more effective in inducing translocations and do not cause any reduction in germination.

Plants monosomic addition for the centric-fused chromosome 4S$^s$S/6S$^l$L (see example 6), homozygous for the ms-B1 and Ki-B1 alleles which carry also Ms-S$^s$1, rht-S$^s$1 and ki-S$^l$1-a, are pollinated by either (i) monosomic addition for the fused chromosome 4S$^s$S/4EL or 4S$^s$S/4A$^m$L homozygous for ms-B1 and Ki-B1 and carrying also Ms-S$^s$1, rht-S$^s$1 and Ba-E1 or Ba-A$^m$1, respectively, or (ii) by monosomic addition 4A$^m$ and carry also Ms-A$^m$1, rht-A$^m$1 and Ba-A$^m$1. Depending on the parental combinations, the $F_1$ progeny contains also the disomic S addition and double monosomic L addition 4S$^s$S/6S$^l$L+4S$^s$S/4EL, 4S$^s$S/6S$^l$L+4S$^s$S/4A$^m$L or 4S$^s$S/6S$^l$L+4A$^m$. A large number of blue seeds are selected and irradiated by 10$^{13}$ N$^{th}$ cm$^{-2}$ of thermal neutrons. The treated seeds are germinated and selection is carried out by chromosome counts and by the use of DNA probes for monosomic addition. These plants are allowed to self and selection is carried out in their progeny for blue seeds, which seeds when grown, developing into male-fertile plants, all of which carries the desired translocation.

Example 13

Figure 16:
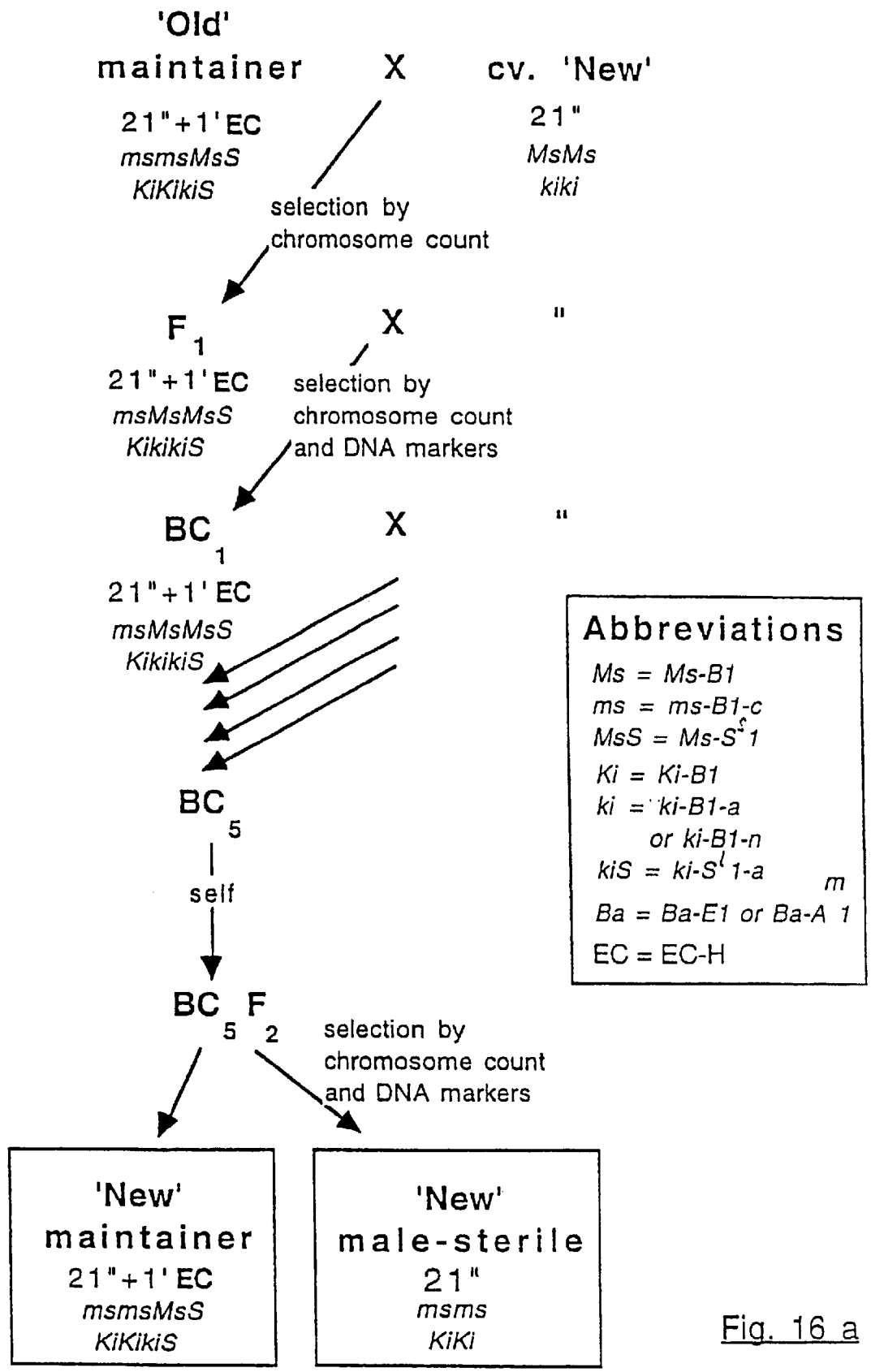
FIGS. 16a–16b depict schematic procedures for conversion of a desired cultivar (cv. 'New') into a male-sterile line and a maintainer line carrying EC-H (16a); and conversion of a desired cultivar (cv. 'New') into a male-sterile line and a recombinant maintainer line carrying REC-H (16b).
Figure 17A:
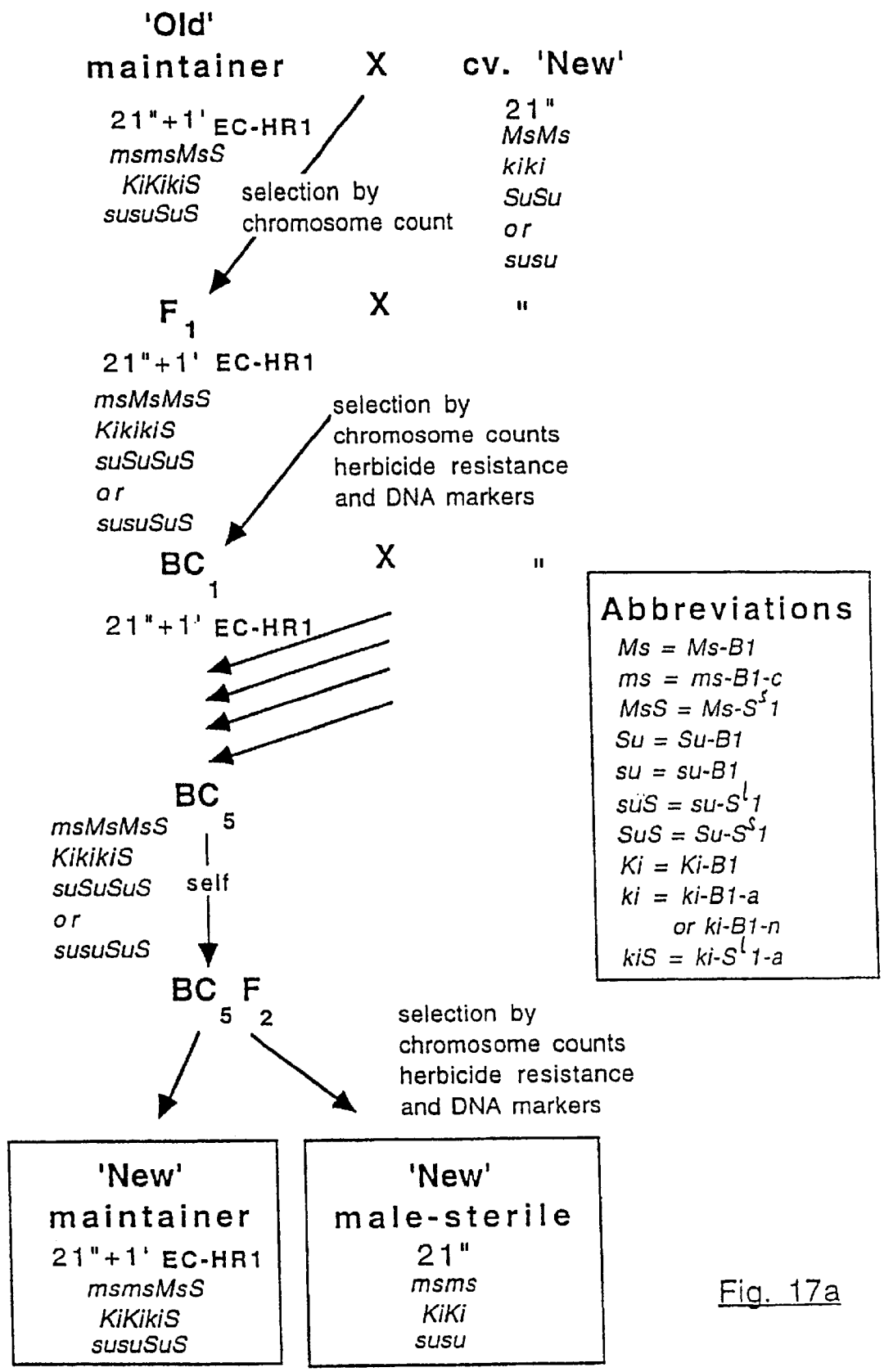
FIGS. 17a–17b depict schematic procedures for conversion of a desired cultivar (cv. 'New') into a male-sterile line and a maintainer line carrying EC-HR (17a); and conversion of a desired cultivar (cv. 'New') into a male-sterile line and a recombinant maintainer line carrying REC-HR (17b).
Figure 18A:
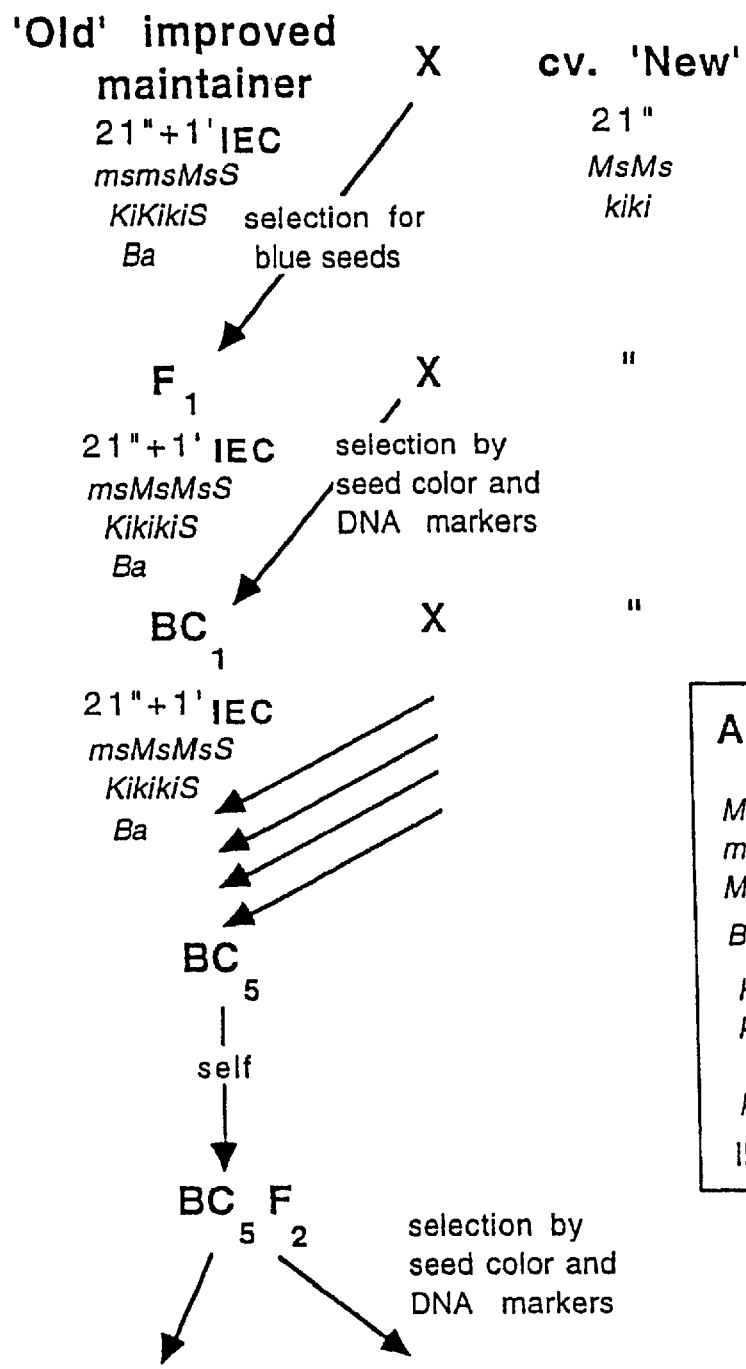
FIGS. 18a–18b depict schematic procedures for conversion of a desired cultivar (cv. 'New') into a male-sterile line and an improved maintainer line carrying IEC-HC (18a); and conversion of a desired cultivar (cv. 'New') into a male-sterile line and an improved recombinant maintainer line carrying IREC-HC (18b).

Conversion of a Desired Common or Durum Wheat Cultivar into a Male-sterile Female Line and a Maintainer Line Either with EC-H, EC-HR or IEC-HC A procedure for the conversion of a desired common wheat cultivar into a male-sterile female parental line and a maintainer line in which the allelic complement of existing female and maintainer lines is replaced by the allelic complement of the desired cultivar to provide a male-sterile female line and a maintainer line or an improved maintainer line having the desired cultivar's allelic complement, is set forth schematically in FIGS. 16a, 17a and 18a.

In this procedure, a maintainer line either with EC-H1, EC-HR1 or one of the types of IEC-HC homozygous for the recessive male-sterility allele ms-B1-c and for the dominant pollen-killer allele Ki-B1 and having the alien engineered chromosome 4S$^s$S/6S$^l$L, that carries the dominant alleles Ms-S$^s$1 and rht-S$^s$1 and the recessive pollen-killer allele ki-S$^l$1-a and in the case of EC-HR1 also the Su-S$^s$1 allele, or the improved engineered chromosomes 4S$^s$S/4EL/6S$^l$L, 4S$^s$S/4A$^m$L/6S$^l$L or 4A$^m$S-4A$^m$L/6S$^l$L carrying the dominant alleles Ms-S$^s$1 and rht-S$^s$1, the dominant blue aleurone Ba-E1 and the recessive pollen-killer allele ki-S$^l$1-a, the Ms-S$^s$1, rht-S$^s$1, Ba-A$^m$1 and ki-S$^l$1-a alleles, or the Ms-A$^m$1, rht-A$^m$1, Ba-A$^m$1 and ki-S$^l$1-a alleles, respectively, as a monosomic addition, is pollinated by the desired cultivar which is homozygous Ms-B1Ms-B1 and ki-B1-aki-B1-a. The $F_1$ hybrids are all heterozygous for the male-sterility alleles, Ms-B1ms-B1-c and for the pollen-killing alleles Ki-B1ki-B1-a, some of which carry also the engineered chromosome. These plants are selected and pollinated again by the desired cultivar to yield BC$_1$ progeny, ¼ of which are heterozygous Ms-B1ms-B1-cKi-B1ki-B1-a, some of which having also the engineered chromosome. The monosomic addition seedlings are selected by chromosome count (i.e., selection for seedlings with 2n=43). Heterozygosity in both loci is determined by the use of DNA markers and progeny test. The selected progeny plants are further backcrossed as female, with the desired cultivar, through four subsequent generations to yield fifth generation backcross progeny (BC$_5$). At each generation, the progeny is analyzed as described for the BC$_1$ progeny and plants heterozygous Ms-B1ms-B1-cKi-B1ki-B1-a that have the engineered chromosome as a monosomic addition are selected. Selfing of the BC$_5$ yields progeny, ⅜₄ of which are homozygous ms-B1-cms-B1-cKi-B1Ki-B1 and are the desired male-sterile female line. Another group (⅛₀) of this progeny that has a similar genotype and has also the engineered chromosome is the desired maintainer.

Example 14

Figure 16B:
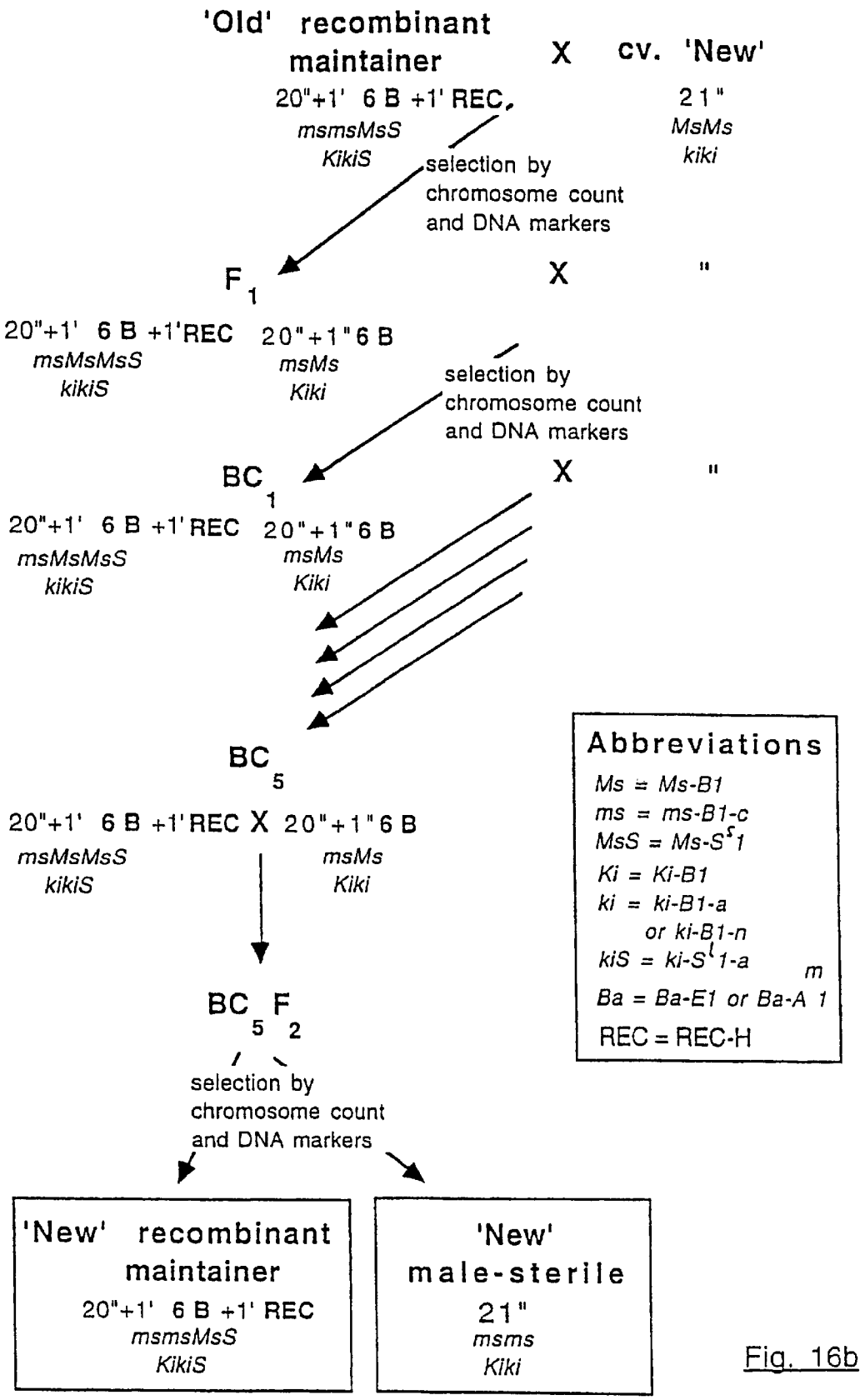
Figure 17B:
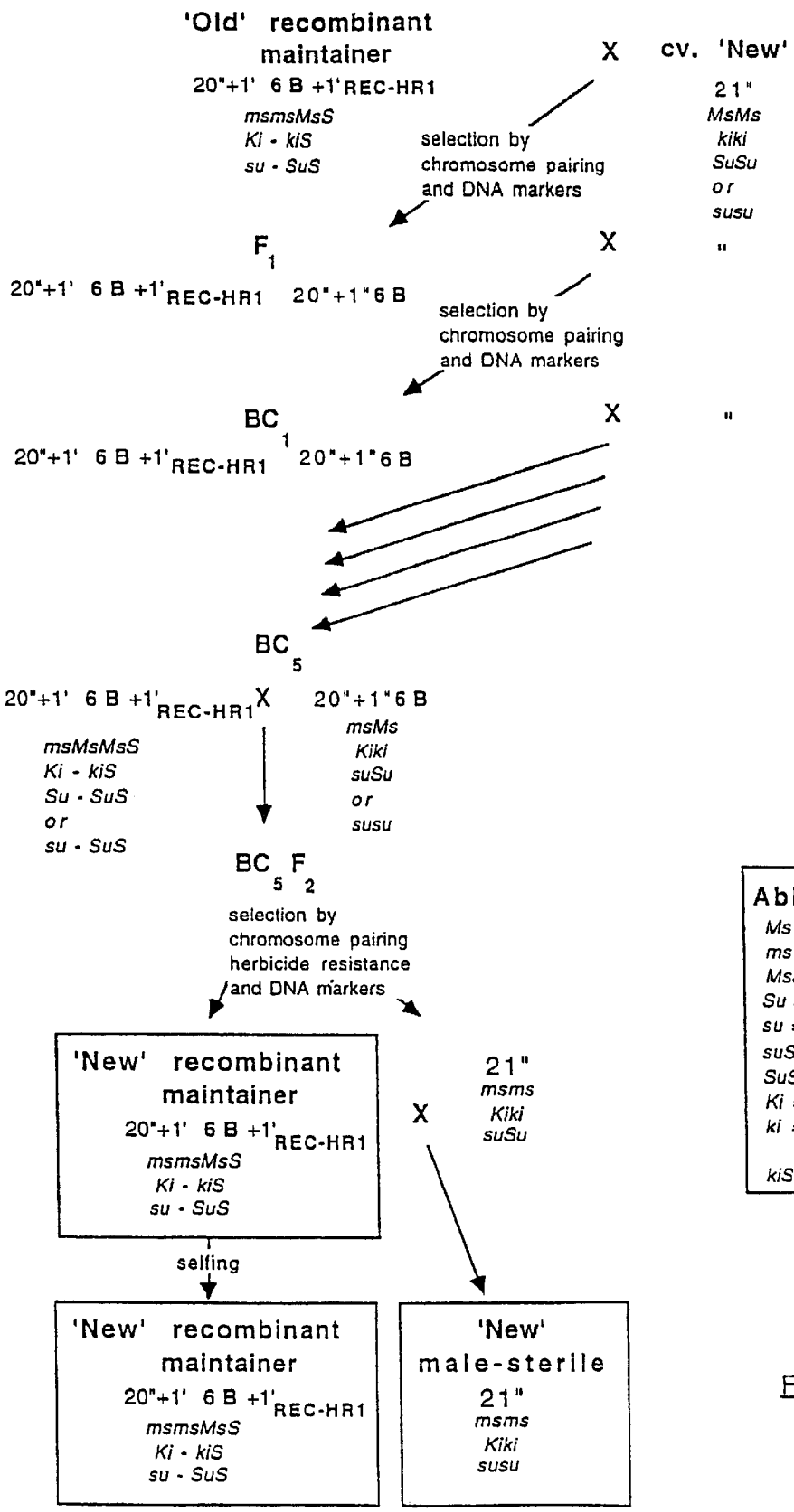
Figure 18B:
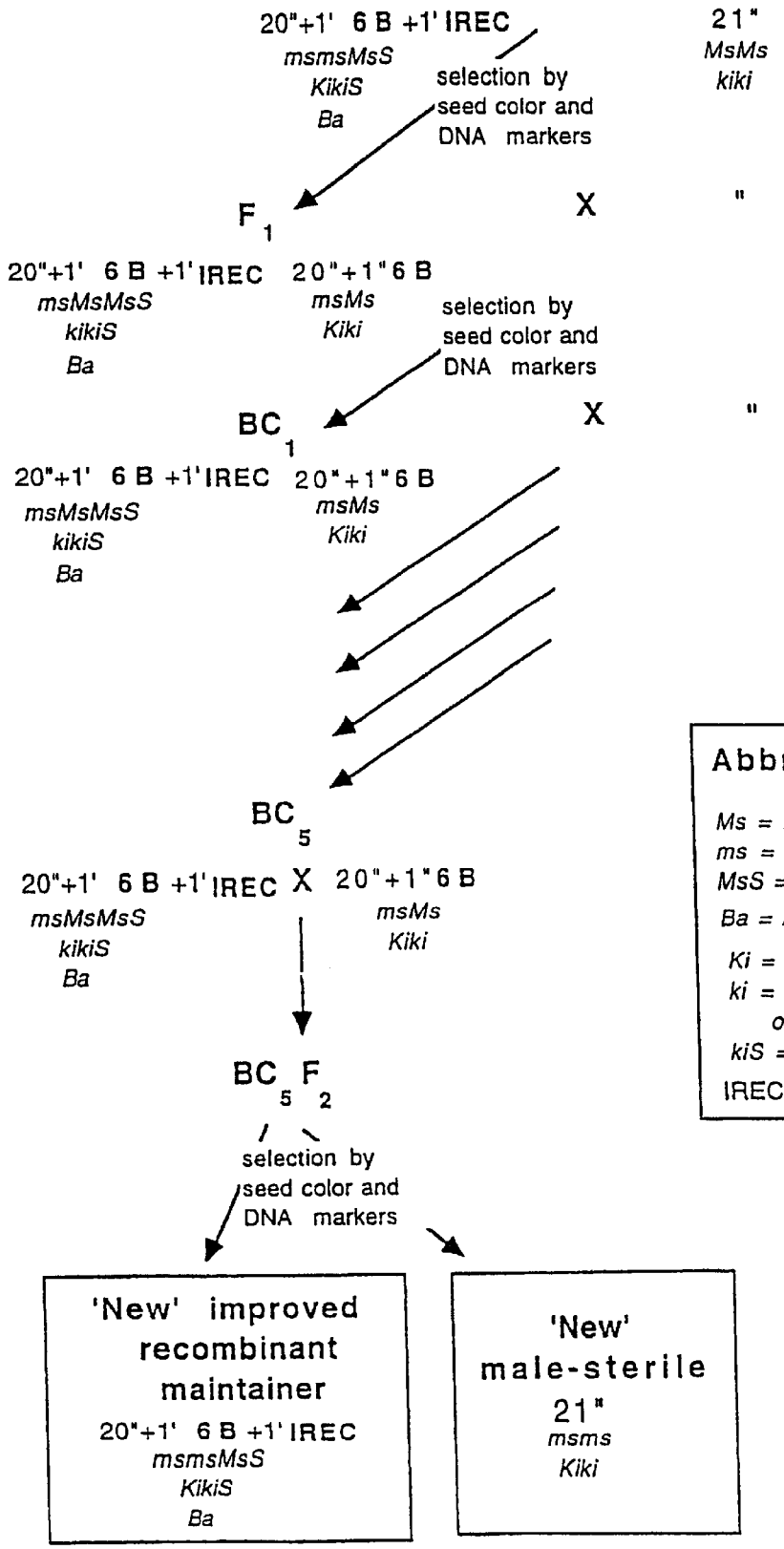

Conversion of a Desired Common or Durum Wheat Cultivar into a Male-sterile Female Line and a Recombinant Maintainer Line Either with REC-H, REC-HR or IREC-HC A procedure for the conversion of a desired common wheat cultivar into a male-sterile female parental line and a recombinant maintainer line in which the allelic complement of existing female and maintainer lines is replaced by the allelic complement of the desired cultivar to provide a male-sterile female line and a recombinant maintainer line having the desired cultivar's allelic complement, is set forth schematically in FIGS. 16b, 17b and 18b.

In this procedure, a recombinant maintainer line which is monosomic 6B—monosomic substitution 4S$^s$S/6S$^l$L/6BL, is homozygous for the recessive male-sterility allele ms-B1-c, possesses thee dominant male-fertility allele Ms-S$^s$1 and is hemizygous for the dominant pollen-killer allele Ki-B1 and for the recessive pollen-killer allele ki-S$^l$1-a and in the case of REC-HR1 also for the Su-S$^s$1 allele, or one of the improved recombinant maintainer lines which is monosomic substitution for the improved recombinant engineered chromosomes 4S$^s$S/4EL/6S$^l$L/6BL, 4S$^s$S/4A$^m$L/6S$^l$L/6BL or 4A$^m$S-4A$^m$L/6S$^l$L/6BL carrying either Ms-S$^s$1, rht-S$^s$1, Ba-E1 and ki-S$^l$1-a alleles, Ms-S$^s$1, rht-S$^s$1, Ba-A$^m$1 and ki-S$^l$1-a alleles or Ms-A$^m$1, rht-A$^m$1, Ba-A$^m$1 and ki-S$^l$1-a alleles, respectively, is pollinated by the desired cultivar which is homozygous Ms-B1Ms-B1 and ki-B1-aki-B1-a. The $F_1$ hybrids are all heterozygous for the male-sterility alleles (Ms-B1ms-B1-c), ½ of which are double monosomics for 6B (receiving this chromosome from their male parent and therefore, hemizygous for ki-B1-a) and for the REC or the IREC, and ½ are disomic 6B and heterozygous Ki-B1ki-B1-a. These disomic and double monosomic plants are selected and pollinated by the desired cultivar to yield BC$_1$ progeny, ½ of which are heterozygous Ms-B1ms-B1-c. This BC$_1$ progeny comprises two types: one type derived from pollinating the double monosomic $F_1$ plants ½ of which are double monosomic for 6B, and therefore, hemizygous for ki-B1-a, and for the REC or the IREC; and another type, derived from pollinating the disomic $F_1$ plants, one half of which are heterozygous Ki-B1ki-B1-a. The heterozygous Ms-B1ms-B1-c BC$_1$ plants monosomic 6B—monosomic substitution for either 4S$^s$S/6S$^l$L/6BL, 4S$^s$S/4EL/6S$^l$L/6BL, 4S$^s$S/4A$^m$L/6S$^l$L/6BL or 4A$^m$S-4A$^m$L/6S$^l$L/6BL and the disomic 6B which are heterozygous Ki-B1ki-B1-a, which are selected by cytological analysis and the use of DNA markers, are further backcrossed as female, with the desired cultivar through four subsequent generations to yield fifth generation backcross progeny (BC$_5$). At each generation, the progeny is analyzed as described for the BC$_1$ progeny and plants heterozygous Ms-B1ms-B1-c and either hemizygous ki-B1-a, that have the REC or the IREC as monosomic substitution, or disomic 6B, heterozygous Ki-B1ki-B1-a, are selected. The selected double monosomic 6B—REC or IREC BC$_5$ plants are then pollinated by the disomic 6B BC$_5$ to yield BC$_5$F$_2$ progeny, of which ⅛ are double monosomic 6B—REC or IREC carrying ms-B1-cms-B1-c Ms-S$^s$1 Ki-B1 and ki-S$^l$1-a and are either the desired recombinant maintainer line or the improved recombinant maintainer line, respectively, and ⅛ are disomic having ms-B1-cms-B1-c and Ki-B1ki-B1-a, and are the desired male-sterile female line.

REFERENCES

Driscoll, C. J. (1972) Crop Sd. 12:516–517.

Driscoll, C. J., (1985) Crop Sd. 25, 1115–1116.

Franckowiak, J. D., Maan, S. S. and Williams, N. D. (1976) Crop Sci. 16:725–728.

Hermsen, J. G. Th (1965) Euphytica 14:221–224.

Keppenne, V. D. and Baenziger, P. S. (1990) Genome 33: 525–529.

Kihara, H. (1951) Cytologia 16:117–193.

Loegering, W. Q. and Sears, E. R. (1963) Can. J. Genet. Cytol. 5: 65–72.

Lukaszewski, A. J. (1993) Genome 36: 821–824.

McIntosh, R. A. (1998) Proc. 8th Int. Wheat Genet. Symp., Beijing, China. pp. 1333–1500.

Sasakuma, T., Maan, S. S. and Williams, N. D. (1978) Crop Science 18: 850–853.

Sears, E. R. (1972) Stadler Symposium 4: 23–38.

Sears, E. R (1977) Can. J. Genet. Cytol. 19: 585–593.

Sharma, D. and Knott, D. R. (1966) Can. J. Genet. Cytol. 8: 137–143.

Snape, J. W., Leckie, D., Parker, B. B. and Nevo, E. (1991) In Casely, J. C., Cussans, G. W. and Atkin, R. K. (eds.) Herbicide Resistance in Weeds and Crops, Butterworth-Heinemann, Oxford, pp. 305–317.

Tsujimoto, H. and Tsunewaki, K. (1983) Proc. 6th Int. Wheat Genet. Symp., Kyoto, Japan. pp. 1077–1081.

Wilson, P. and Driscoll, C. J. (1983) in Frenkel, R. (ed.) Monographs on Theoretical and Applied Genetics, Vol. 6, Heterosis, Springer-Verlag, pp. 94–123.

Zeven, A. C. (1991) Euphytica 56: 243–258.

[For Pugsley and Oram, 1959; Fossatti and Ingold, 197; and Driscoll, 1977 see above review by Wilson and Driscoll, 1983].

What is claimed is:

1. A method for the maintenance of a male-sterile female parental line of common or durum wheat for use in the production of hybrid wheat, said method comprising:

(a) crossing a female parent with a male parent, said female parent being a male-sterile plant homozygous both for any one of the recessive ms-B1 male-sterility alleles on the short arm of chromosome 4B (4BS), and for the dominant pollen-killer Ki-B1 allele on the long arm of chromosome 6B (6BL), said male parent being the maintainer line and being isogenic to the female parent and homozygous for the same ms-B1 and Ki-B1 alleles as the female parent, and having an additional alien engineered chromosome selected from: (i) an engineered chromosome, herein referred to as EC, consisting of segments derived from two or more different alien chromosomes, carrying a dominant male-fertility allele Ms, a recessive allele ki which is susceptible to the killing action of the native pollen-killer allele on 6BL and one or two selectable markers by which plants having this chromosome can be selected; and (ii) an improved engineered chromosome, herein referred to as IEC, consisting of segments derived from two or more different alien chromosomes carrying, in addition to the Ms, ki and the selectable marker alleles, a seed marker by which seeds having this chromosome can be separated from seeds not having it; and (b) harvesting from the cross of (a) the progeny seed, all of which are homozygous for said male-sterility and pollen-killer alleles and lack the engineered chromosome EC or IEC, said seeds, when grown, developing into said male-sterile female line.

2. The method according to claim 1 wherein said engineered chromosome, herein designated EC-H, carries as a selectable marker a rht allele determining normal plant height.

3. The method according to claim 1 wherein said improved engineered chromosome, herein designated IEC-HC, carries as a selectable marker a rht allele and as a seed marker a Ba allele determining blue color of the seeds.

4. The method according to claim 2 wherein said engineered chromosome EC-H is the engineered chromosome EC-H1 consisting of 4S$^s$S/6S$^l$L that carries Ms-S$^s$1 and rht-S$^s$1 on the short arm and ki-S$^l$1-a on the long arm.

5. The method according to claim 3 wherein said improved engineered chromosome IEC-HC is selected from the group consisting of IEC-HC1, consisting of 4S$^s$S/4EL/6S$^l$L that carries Ms-S$^s$1, rht-S$^s$1, Ba-E1 and ki-S$^l$1-a; IEC-HC2 consisting of 4S$^s$S/4A$^m$L/6S$^l$L that carries Ms-S$^s$1, rht-S$^s$1, Ba-A$^m$1 and ki-S$^l$1-a; and IEC-HC3 consisting of 4A$^m$S-4A$^m$L/6S$^l$L that carries Ms-A$^m$1, rht-A$^m$1, Ba-A$^m$1 and ki-S$^l$1-a.

6. A method for the maintenance of a male-sterile female parental line of common or durum wheat for use in the production of hybrid wheat, said method comprising:

(a) crossing a female parent with a male parent, said female parent being a male-sterile plant homozygous both for any one of the recessive ms-B1 male-sterility alleles on the short arm of chromosome 4B (4BS), and for the dominant pollen-killer Ki-B1 allele on the long arm of chromosome 6B (6BL), said male parent being the maintainer line and being isogenic to the female parent and homozygous for the same ms-B1 allele as the female parent but monosomic both for chromosome 6B carrying the Ki-B1 allele and for a recombinant engineered chromosome selected from: (i) a recombinant engineered chromosome, herein referred to as REC, consisting of segments derived from two or more different alien chromosomes and from the distal segment of the native chromosome arm 6BL, carrying a Ms allele, a ki allele and one or two selectable markers by which plants having this chromosome can be selected; and (ii) an improved recombinant engineered chromosome, herein referred to as IREC, consisting of segments derived from two or more different alien chromosomes and from the distal segment of the native chromosome arm 6BL, carrying, in addition to the Ms, ki and the selectable marker alleles, a seed marker by which seeds having this chromosome can be separated from seeds not having it; and (b) harvesting from the cross of (a) the progeny seed, all of which are homozygous for said male-sterility and pollen-killer alleles and lack the recombinant engineered chromosome REC or IREC, said seeds, when grown, developing into said male-sterile female line.

7. The method according to claim 6 wherein said recombinant engineered chromosome is designated REC-H and carries as a selectable marker a rht allele determining normal plant height.

8. The method according to claim 6 wherein said improved recombinant engineered chromosome is designated IREC-HC and carries as a selectable marker a rht allele and as a seed marker a Ba allele determining blue color of the seeds.

9. The method according to claim 7 wherein said recombinant engineered chromosome, REC-H, is the recombinant engineered chromosome REC-H1, consisting of 4SsS/6SlL/6BL that carries Ms-Ss1 and rht-Ss1 on the short arm and ki-Sl1-a on the long arm.

10. The method according to claim 8 wherein said improved recombinant engineered chromosome IREC is selected from the group consisting of IREC-HC1, consisting of $4S^sS/4EL/6S^lL/6BL$ that carries $Ms-S^s1$, $rht-S^s1$, Ba-E1 and $ki-S^l1-a$; IREC-HC2 consisting of $4S^sS/4A^{m}L/6S^lL/6BL$ that carries $Ms-S^s1$, $rht-S^s1$, $Ba-A^{m}1$ and $ki-S^l1-a$; and IREC-HC3 consisting of $4A^{m}S-4A^{m}L/6S^lL/6BL$ that carries $Ms-A^{m}1$, $rht-A^{m}1$, $Ba-A^{m}1$ and $ki-S^l1-a$.

11. The method according to claim 2 wherein engineered chromosome EC-H, carries a chlorotoluron resistance allele Su as a further selectable marker, and is designated EC-HR.

12. The method according to claim 11 wherein engineered chromosome EC-HR, carries Ms-Ss1, rht-Ss1, Su-Ss1 and ki-Sl1-a and is designated EC-HR1.

13. The method according to claim 7 wherein recombinant engineered chromosome REC-H, carries a chlorotoluron resistance allele Su as a further selectable marker, and is designated REC-HR.

14. The method according to claim 13 wherein said recombinant engineered chromosome REC-HR consists of $4S^sS/6S^lL/6BL$ that carries $Ms-S^s1$, $rht-S^s1$, $Su-S^s1$ and $ki-S^l1-a$, said recombinant engineered chromosome being herein designated REC-HR1.

15. A method for the maintenance of a male-sterile female parental line of common or durum wheat for use in the production of hybrid wheat, said method comprising:

(a) selfing a maintainer line which is isogenic to the female parent, i.e., homozygous both for any one of the recessive ms-B1 male-sterility alleles and for the dominant pollen-killer Ki-B1 allele, and having an additional improved engineered chromosome, herein designated IEC, carrying, in addition to Ms, ki and the selectable marker alleles, a seed marker by which seeds having said chromosome IEC can be separated from seeds not having it;

(b) harvesting from the selfed plants of (a) the progeny seed, all of which are homozygous for said male-sterility and pollen-killer alleles; and (c) separating the seeds containing the IEC and therefore containing the seed marker from the seeds not containing the IEC and therefore lacking the seed marker, said seeds lacking the seed marker developing into said male-sterile female line when grown.

16. A method according to claim 15 wherein said seed marker allele is a Ba allele determining blue seed color and the blue seeds are separated from seeds lacking the Ba allele by a sorting apparatus.

17. A method according to claim 15 wherein said improved engineered chromosome IEC is selected from the group consisting of IEC-HC1, consisting of $4S^sS/4EL/6S^lL$ that carries $Ms-S^s1$, $rht-S^s1$, Ba-E1 and $ki-S^l1-a$; IEC-HC2 consisting of $4S^sS/4A^{m}L/6S^lL$ that carries $Ms-S^s1$, $rht-S^s1$, $Ba-A^{m}1$ and $ki-S^l1-a$; and IEC-HC3 consisting of $4A^{m}S-4A^{m}L/6S^lL$ that carries $Ms-A^{m}1$, $rht-A^{m}1$, $Ba-A^{m}1$ and $ki-S^l1-a$.

18. A method for the maintenance of a male-sterile female parental line of common or durum wheat for use in the production of hybrid wheat, said method comprising:

(a) selfing an improved recombinant maintainer line which is isogenic to the female parent, i.e., homozygous for any one of the recessive ms-B1 male-sterility alleles on 4BS, but monosomic both for chromosome 6B carrying the Ki-B1 allele and for an improved recombinant engineered chromosome, herein designated IREC, carrying, in addition to Ms, ki and the selectable marker alleles, a seed marker allele by which seeds having said chromosome IREC can be separated from seeds not having it;

(b) harvesting from the selfed plants of (a) the progeny seed, all of which are homozygous for said male-sterility allele, 50% of which are disomic for chromosome 6B and lack the IREC and the seed marker, and 50% containing the IREC and show the seed marker;

(c) planting the progeny seed of (b) in mixture to allow pollination of the male-sterile plants by the male-fertile ones as well as for self-pollination of the male-fertile ones, resulting in a mixture of progeny seeds; and (d) separating about 75% of the seeds which are disomic for chromosome 6B and lack the IREC and the seed marker and develop into said male-sterile female line when grown, from the remainder 25% of seeds containing the IREC and the seed marker.

19. The method according to claim 18 wherein said seed marker allele is a Ba allele determining blue seed color, and the blue seeds are separated from seeds lacking the Ba allele by a sorting apparatus.

20. The method according to claim 18 wherein said improved recombinant engineered chromosome IREC is selected from the group consisting of IREC-HC1, consisting of $4S^sS/4EL/6S^lL/6BL$ that carries $Ms-S^s1$, $rht-S^s1$, Ba-E1 and $ki-S^l1-a$; IREC-HC2, consisting of $4S^sS/4A^{m}L/6S^lL/6BL$ that carries $Ms-S^s1$, $rht-S^s1$, $Ba-A^{m}1$ and $ki-S^l1-a$; and IREC-HC3, consisting of $4A^{m}S-4A^{m}L/6S^lL/6BL$ that carries $Ms-A^{m}1$, $rht-A^{m}1$, $Ba-A^{m}1$ and $ki-S^l1-a$.

21. A maintainer line selected from a male-fertile maintainer line and an improved male-fertile maintainer line of common or durum wheat for the maintenance of a male-sterile female parental line for use in the production of hybrid wheat, said maintainer line or improved maintainer line being isogenic to the female parent and homozygous both for any one of the ms-B1 male-sterility alleles and for the pollen-killer Ki-B1 allele of the female parental line, and having an additional alien engineered chromosome selected from: (i) EC, consisting of segments derived from two or more different alien chromosomes, carrying a dominant male-fertility allele Ms, a recessive allele ki which is susceptible to the killing action of the native pollen-killer allele on 6BL and a selectable marker by which plants having said chromosome EC can be selected; and (ii) IEC, consisting of segments derived from two or more different alien chromosomes carrying, in addition to the Ms, ki and the selectable marker alleles, a seed marker by which seeds having said chromosome IEC can be separated from seeds not having it.

22. A maintainer line selected from a recombinant male-fertile maintainer line and from an improved recombinant male-fertile maintainer line of common or durum wheat for the maintenance of a male-sterile female parental line for use in the production of hybrid wheat, said maintainer line or improved maintainer line being isogenic to the female parental line, i.e., homozygous for any one of the ms-B1 male-sterility alleles but monosomic both for chromosome 6B carrying the Ki-B1 allele and for a recombinant or improved recombinant engineered chromosome selected from: (i) REC, consisting of segments derived from two or more different alien chromosomes and from the distal segment of the native chromosome arm 6BL, carrying a Ms allele, a ki allele and a selectable marker by which plants having said chromosome REC can be selected; and (ii) IREC, consisting of segments derived from two or more different alien chromosomes and from the distal segment of the native chromosome arm 6BL carrying, in addition to the Ms, ki and the selectable marker alleles, a seed marker by which seeds having said chromosome IREC can be separated from seeds not having it.

23. The maintainer line according to claim 21 wherein said engineered chromosome is selected from the group consisting of EC-H, IEC-HC, REC-H and IREC-HC and carries as a selectable marker a rht allele determining normal plant height.

24. The maintainer line according to claims 21 wherein said engineered chromosome is selected from the group consisting of IEC-HC and IREC-HC and carries as a selectable seed marker a Ba allele for blue aleurone color.

25. The maintainer line according to claim 23 wherein the engineered chromosome is selected from: (i) REC-H1 carrying the Ms-$S^s$1, rht-$S^s$1 and ki-$S^l$1-a alleles, and (ii) one of the IREC-HCs carrying Ms-$S^s$1, rht-$S^s$1, Ba-E1 and ki-$S^l$1-a or Ms-$S^s$1, rht-$S^s$1, Ba-$A^m$1 and ki-$S^l$1-a or Ms-$A^m$1, rht-$A^m$1, Ba-$A^m$1 and ki-$S^l$1-a.

26. A maintainer line selected from a male-fertile maintainer line of common or durum wheat for the maintenance of a male-sterile female parental line for use in the production of hybrid wheat, said maintainer line being isogenic to the female parent and homozygous both for any one of the ms-B1 male-sterility alleles, for the chlorotoluron herbicide susceptibility allele su-B1 and for the pollen-killer Ki-B1 allele of the female parental line, and having an additional alien engineered chromosome selected from EC-HR type, consisting of segments derived from two or more different alien chromosomes, carrying a dominant male-fertility allele Ms, a recessive allele ki which is susceptible to the killing action of the native pollen-killer allele on 6BL and two selectable markers, a rht and a Su alleles by which plants having said chromosome EC-HR can be selected.

27. The maintainer line according to claim 26 wherein said engineered chromosome is of the EC-HR1 type carrying as selectable markers the rht-$S^s$1 and the Su-$S^s$1 alleles.

28. A maintainer line selected from a male-fertile recombinant maintainer line of common or durum wheat for the maintenance of a male-sterile female parental line for use in the production of hybrid wheat, said maintainer line being isogenic to the female parental line, i.e., homozygous for any one of the ms-B1 male-sterility alleles but monosomic both for chromosome 6B carrying the su-B1 and Ki-B1 alleles and for a recombinant engineered chromosome selected from REC-HR type, consisting of segments derived from two or more different alien chromosomes and from the distal segment of the native chromosome arm 6BL, carrying a Ms allele, a ki allele and selectable markers by which plants having said chromosome REC-HR can be selected.

29. The maintainer line according to claim 28 wherein said engineered chromosome is of the REC-HR1 type carrying as selectable markers the rht-$S^s$1allele determining normal plant height and the Su-$S^s$1 allele conferring resistance to chlorotoluron.

30. A method for maintaining a constant ratio between male-fertile to male-sterile plants in each generation of a maintainer line or a recombinant maintainer line of common and durum wheat, comprising:

(a) selfing a male-fertile maintainer line containing an engineered chromosome selected from the group of the engineered chromosome EC-H and the recombinant engineered chromosome REC-H, carrying in addition to the Ms and ki alleles, at least one selectable marker allele that facilitates the selection of seeds of the male-fertile selfed progeny, said seeds, when grown, developing into said maintainer line;

(b) collecting the progeny seeds of (a) and growing said seeds thus producing plants, 20% of which (progeny of the maintainer line having the engineered chromosome EC-H) or 50% of which (progeny of the maintainer line having the recombinant engineered chromosome REC-H) contain the said engineered chromosome, and are the same as the said maintainer line and therefore carry the selectable marker allele by which they can be selected from those lacking the said engineered chromosome; and (c) harvesting the plants exhibiting the selectable marker of (b), all of which are male-fertile, and obtaining the progeny seeds consisting of 20% (progeny of the maintainer line having the engineered chromosome EC-H) or 50% (progeny of the maintainer line having the recombinant engineered chromosome REC-H) seeds carrying the said engineered chromosome, thus keeping constant the ratio of male-fertile to male-sterile plants in each generation of the maintainer line or the recombinant maintainer line.

31. The method according to claim 30 wherein the selectable marker is the rht allele that promotes plant height, thus facilitating the selective harvest of seeds of the male-fertile maintainer, said seeds, when grown, developing into said maintainer line.

32. A method for maintaining a constant ratio between male-fertile to male-sterile plants in each generation of a maintainer line or a recombinant maintainer line of common and durum wheat, comprising:

(a) selfing a male-fertile maintainer line containing an engineered chromosome selected from the group of the engineered chromosome EC-HR and the recombinant engineered chromosome REC-HR, carrying, in addition to the Ms-Ss1 and ki-Sl1-a alleles, a herbicide resistance allele as a selectable marker, facilitating the selection of plants having the same said maintainer genotype from the male-fertile progeny of the selfed maintainer line;

(b) collecting the progeny seeds of (a), germinating said seeds into a seedling progeny, 20% of which (EC-HR) or 50% of which (REC-HR) contain the said engineered chromosome, and spraying the seedlings with the herbicide thus killing all the susceptible seedlings, i.e., those lacking the engineered chromosome; and (c) harvesting the herbicide resistant plants of (b), all of which carry said engineered chromosome and therefore are male-fertile, and obtaining the progeny seeds consisting of 20% (EC-HR) or 50% (REC-HR) seeds carrying the said engineered chromosome, thus keeping constant the ratio of male-fertile to male-sterile plants in each generation of the maintainer or the recombinant maintainer.

33. The method according to claim 32 wherein the selectable herbicide resistance allele is the Su-S$^s$1 allele that confers resistance to chlorotoluron.

34. A method for planting only male-fertile maintainer plants in each generation of an improved maintainer line or an improved recombinant attainer line of common and durum wheat, comprising:
   (a) selfing a male-fertile maintainer line containing an engineered chromosome selected from the group of the improved engineered chromosome IEC-HC and the improved recombinant engineered chromosome IREC-HC, carrying, in addition to the Ms-Ss1 and ki-Sl1-a alleles, a seed marker, by which seeds having said engineered chromosome can be selected from seeds not having it in the progeny of the selfed said male-fertile maintainer, said seeds, when grown, developing into said maintainer line;
   (b) collecting the progeny seeds of (a), and separating the seeds exhibiting the seed marker from the seeds not exhibiting said marker, by a sorting apparatus; and
   (c) planting the seeds exhibiting the seed marker of (b), all of which develop into male-fertile improved maintainer or improved recombinant maintainer plants.

35. The method according to claim 34 wherein the seed marker is a Ba allele that determines blue seed color.

36. A method for producing a male-fertile maintainer line of common or durum wheat having the engineered chromosome EC-H1, said method comprising:
   (a) crossing a male-fertile female parent derived from the common wheat cultivar Chinese Spring, said female parent being homozygous for both the dominant Ms-B1 male-fertility allele on chromosome arm 4BS, and the dominant Ki-B1 pollen-killer allele on 6BL, and having an additional alien chromosome 6S$^l$ carrying on its long arm the recessive pollen-killer allele ki-S$^l$1-a, with a male parent that is isogenic to the female parent and homozygous for the recessive ms-B1-c male-sterility allele and has, instead of chromosome 6S$^l$, an additional alien chromosome 4S$^s$ carrying on its short arm the dominant alleles Ms-S$^s$1 and rht-S$^s$1;
   (b) collecting the progeny seed of the cross of (a) and growing said seeds, thus producing male-fertile $F_1$ plants, some of which are double monosomic addition, i.e., they have the two alien chromosomes 4S$^s$ carrying Ms-S$^s$1 and rht-S$^s$1 and 6S$^l$ carrying ki-S$^l$1-a;
   (c) selfing said $F_1$ progeny of (b), collecting a large number of the progeny seed thereof and growing said seeds, thus producing $F_2$ plants, some of which are monosomic addition for an alien translocated engineered chromosome EC-H1, 25% of which are homozygous for the ms-B1-c male sterility allele and are the desired plants;
   (d) selecting said desired plants of (c) by chromosome count, C-banding and use of DNA markers and selfing them;
   (e) collecting the selfed progeny seed of (d) and growing said seeds, thus producing $F_3$ plants, all of which are homozygous for the ms-B1-c male-sterility allele, 25% of which are male-fertile because they have also said additional alien engineered chromosome EC-H1, these being the desired maintainer line plants; and
   (f) selecting the desired maintainer line plants of (e) by chromosome count and use of DNA markers.

37. A method for producing a male-fertile recombinant maintainer line of common or durum wheat having the recombinant engineered chromosome REC-HL, said method comprising:
   (a) crossing a male-fertile female parent derived from the common wheat cultivar Chinese Spring, said female parent being homozygous for the dominant Ms-B1 male-fertility allele on chromosome arm 4BS and for the dominant homoeologous-pairing suppressor allele Ph1 on chromosome arm 5BL, nullisomic for chromosome 6B and therefore deficient for the dominant Ki-B1 pollen-killer allele, and having a pair of 6S$^l$ chromosomes carrying the recessive pollen-killer allele ki-Sl1-a, with a male parent that is isogenic to the female parent but is disomic 6B and therefore homozygous for Ki-B1, lacks chromosome 6Sl, and is also homozygous for the mutant homoeologous-pairing allele ph1 b;
   (b) collecting the progeny seed of the cross of (a) and growing said seeds, thus producing male-fertile (Ms-B1 Ms-B1) $F_1$ plants heterozygous for the homoeologous-pairing alleles (Ph1ph1b), all of which are monosomic for both 6B and 6Sl chromosomes;
   (c) backcrossing said $F_1$ plants of (b) to the male parent;
   (d) collecting the progeny seed of the cross of (c) and growing said seeds, thus producing $BC_1$ plants, all of which are male-fertile (Ms-B1Ms-B1), 50% of which are homozygous for the ph1b allele, of which about 18% are double monosomic for both 6B and 6Sl chromosomes and are the desired BC1 plants;
   (e) selecting the desired BC1 plants of (d) by using DNA markers and analysis of chromosome pairing at meiosis, and pollinating them by a ditelosomic 6BS line which is isogenic to the BC1 plants but is homozygous Ph 1 Ph1;
   (f) collecting the progeny seed of the cross of (e) and growing said seeds, thus producing plants, all of which are monotelosomic for chromosome arm 6BS, some of which are also monosomic for a recombinant chromosome consisting of the short arm and the proximal region of the long arm of 6Sl (carrying ki-Sl1-a) and the distal region of chromosome arm 6BL (the recombination point is distal to ki-Sl1-a) and are the desired plants;
   (g) selecting said desired plants of (f) by C-banding, use of DNA markers and analysis of chromosome pairing and crossing them as males with a female line which is the non-recombinant maintainer line, i.e., homozygous for both any one of the recessive male-sterility allele ms-B1 and the dominant pollen-killer allele Ki-B1 and having the engineered chromosome EC-H1;
   (h) collecting the progeny seed of the cross of (g) and growing said seeds, thus producing F1 plants, some of which are triple monosomics, i.e., monosomic for 6B, for the alien engineered chromosome EC-H1 and for the recombinant chromosome (6Sl/6BL) and are heterozygous Ms-B1 ms-B1, hemizygous Ki-B1 and homozygous ki-Sl1-aki-Sl1-a and are the desired plants; and
   (i) selecting said desired plants of (h) by chromosome count, C-banding and by the use of DNA markers and selfing them, collecting the progeny seed thereof and growing said seeds, thus producing F2 plants, some of which are double monosomics, having chromosome 6B and the recombinant engineered chromosome REC-H1, carrying Ms-Ss1, rht-Ss1 and ki-Sl1-a, these being the desired maintainer line plants.

38. A method for producing a male-fertile maintainer line of common or durum wheat having the engineered chromosome EC-HR1, comprising:

(a) crossing a male-fertile female parent derived from the male-fertile maintainer line in the common wheat cultivar Chinese Spring, said female parent being homozygous for the recessive ms-B1 male-sterility allele, the recessive su-B1 chlorotoluron susceptibility allele and the dominant Ki-B1 pollen-killer allele, and having, as a monosomic addition, the engineered chromosome EC-H1 carrying on its short arm the dominant male-fertility allele Ms-S$^s$1 and the semi-dominant rht-S$^s$1 allele and on its long arm the recessive chlorotoluron susceptibility allele su-S$^l$1 and the recessive pollen-killer allele ki-S$^l$1-a, with the line of the diploid species *Aegilops searsii* that possesses the dominant chlorotoluron resistance allele Su-S$^s$1 on 6S$^s$L as well as the Ms-S$^s$1 and rht-S$^s$1 alleles on 4S$^s$S;

(b) collecting the progeny seed of the cross of (a) and growing said seeds, thus producing $F_1$ plants, some of which have 2n=29 chromosomes, i.e., they have one chromosome set from Chinese Spring, the engineered chromosome EC-H1 and a chromosome set from *Aegilops searsii*, having the genotype ms-B1Ms-S$^s$1Ms-S$^s$1, ki-B1ki-S$^l$1-a and su-B1su-S$^l$1Su-S$^s$1;

(c) selecting said $F_1$ progeny of (b) with 2n=29 chromosomes and backcrossing them to cv. Chinese Spring as a male, collecting the progeny seed thereof and growing said seeds, thus producing $BC_1$ plants, some of which that are resistant to chlorotoluron are monosomic addition for the engineered chromosome EC-HR1, all of which are heterozygous ms-B1Ms-B1 and homozygous for su-B1 and Ki-B1 and are the desired plants;

(d) selecting said desired plants of (c) by chromosome count and use of DNA markers and selfing them;

(e) collecting the selfed progeny seed of (d) and growing said seeds, thus producing $BC_1F_2$ plants, 20% of which are resistant to chlorotoluron, i.e., carry the engineered chromosome, 25% of the resistant plants are homozygous for ms-B1 but are male-fertile because they carry the Ms-S$^s$1 of the engineered chromosome EC-HR1, these being the desired maintainer line plants; and (f) selecting the desired maintainer line plants of (e) by their chlorotoluron resistance and use of DNA markers.

39. A method for producing a male-fertile recombinant maintainer line of common or durum wheat having the recombinant engineered chromosome REC-HR1, comprising:

(a) crossing a male-fertile female parent derived from the male-fertile recombinant maintainer line in the common wheat cultivar Chinese Spring, which is monosomic 6B addition REC-H1, said female parent being homozygous for the recessive ms-B1 male-sterility allele and hemizygous for the recessive chlorotoluron susceptibility allele su-B1 and the dominant Ki-B1 pollen-killer allele, and having, as a monosomic substitution, the engineered chromosome REC-H1 carrying on its short arm the dominant male-fertility allele Ms-Ss1 and the semi-dominant rht-Ss1 allele and on its long arm the recessive chlorotoluron susceptibility allele su-Sl1 and the recessive pollen-killer allele ki-Sl1-a, with the line of the diploid species *Aegilops searsii* that possesses the dominant chlorotoluron resistance allele Su-Ss1 as well as the Ms-Ss1 and rht-Ss1 alleles;

(b) collecting the progeny seed of the cross of (a) and growing said seeds, thus producing F1 plants, 50% of which contain the recombinant engineered chromosome that pairs with 4SsS and 6SsS thus forms a trivalent at meiosis, having the genotype ms-B1Ms-Ss1Ms-Ss1, ki-Sl1-a su-Sl1 and Su-Ss1;

(c) selecting said F1 progeny of (b) and backcrossing them to cv. Chinese Spring as a male;

(d) collecting the progeny seed thereof and growing said seeds, thus producing $BC_1$ plants, all of which are heterozygous ms-B1Ms-B1 and therefore male-fertile, some of which are monosomic 6B and therefore hemizygous for su-B1 and Ki-B1 and having the recombinant engineered chromosome REC-HR1 as monosomic substitution carrying Ms-Ss1 and rht-Ss1 on the short arm and Su-Ss1 and ki-Sl1-a on the long arm and are the desired plants;

(e) selecting said desired plants of (c) by their resistance to chlorotoluron and by the analysis of chromosome pairing at meiosis and selfing them;

(f) collecting the selfed progeny seed of (d) and growing said seeds, thus producing BC1F2 plants, 50% of which are monosomic 6B and monosomic for the recombinant chromosome REC-HR1 consisting of the short arm of 4Ss (carrying Ms-Ss1 and rht-Ss1), the proximal region of the long arm of 6Sl (carrying Su-Ss1 and ki-Sl1-a) and the distal region of chromosome arm 6BL (the recombination point is distal to ki-Sl1-a), 25% of these plants are homozygous for ms-B1 and hemizygous for su-B1 and Ki-B1 these being the desired maintainer line plants; and (g) selecting the desired maintainer line plants of (e) by chlorotoluron resistance and use of DNA markers.

40. A method for producing a male-fertile improved maintainer line of common or durum wheat having the improved engineered chromosome IEC-HC1, said method comprising:

(a) crossing a male-fertile female parent derived from the common wheat cultivar Chinese Spring, said female parent being the maintainer line, i.e., homozygous for both the recessive ms-B1 male-sterility allele on chromosome arm 4BS, and the dominant Ki-B1 pollen-killer allele on 6BL, and having an additional engineered chromosome EC-H1 carrying on its short arm the dominant alleles Ms-Ss1 and rht-Ss1 and on its long arm the recessive allele ki-Sl1-a, with a male parent that is isogenic to the female parent but is homozygous for the dominant male-fertility allele Ms-B1 and has an additional pair of the alien chromosomes 4E carrying on its long arm the dominant blue aleurone allele Ba-E1;

(b) collecting the progeny seed of the cross of (a), all of which are blue, irradiating them by thermal neutrons, and growing said seeds, thus producing male-fertile $F_1$ plants, all being heterozygous MsB1ms-B1 and homozygous for Ki-B1, 20% of which are double monosomic addition for the engineered chromosome EC-H1 and for chromosome 4E and are the desired plants;

(c) selecting said desired $F_1$ plants of (b) by chromosome count and by using DNA markers and selfing them;

(d) collecting the progeny seeds of (c), selecting the blue seeds and growing said seeds, thus producing $F_2$ plants, some of which have 43 chromosomes, some of these having the improved engineered chromosome IEC-HC1 containing 4S$^s$S/4EL/6S$^l$L carrying Ms-S$^s$1, rht-S$^s$1, Ba-E1 and ki-S$^l$1 and are the desired plants while some others contain the translocated chromosome 4S$^s$S/4EL;

(e) selecting the desired plants of (d) by chromosome count and by the use of DNA markers and selfing them;

(f) collecting the progeny seed of (e) and selecting the blue seeds, which seeds when grown, develop into male-fertile plants carrying the improved engineered chromosome IEC-HC1, these being the desired improved maintainer line plants;

(g) if in step (d) no desired plant is obtained, then selecting plants of (d) having the translocated chromosome 4SsS/4EL (originating from blue seeds and being male-fertile) by chromosome count and by the use of DNA markers and backcrossing them as male parent to the maintainer line having the EC-H1 to produce $F_1$ seeds;

(h) selecting from said F1 seeds of (g) the blue seeds, irradiating them by thermal neutrons and germinating them and selecting seedlings with 44 chromosomes, i.e., having two alien addition chromosomes 4S$^s$S/4EL and EC-H1 (4S$^s$S/6S$^l$L); and (i) repeating steps (d)–(f), thus obtaining the desired improved maintainer line having the improved engineered chromosome IEC-HC1 containing 4S$^s$S/4EL/6S$^l$L carrying Ms-S$^s$1, rht-S$^s$1, Ba-E1 and ki-S$^l$1.

41. A method for producing a male-fertile improved maintainer line of common or durum wheat having the improved engineered chromosome IEC-HC1, said method comprising:

(a) crossing a male-fertile female parent derived from the common wheat cultivar Chinese Spring, said female parent being homozygous for both the dominant male-fertility allele Ms-B1 and for the dominant pollen-killer Ki-B1 allele and having an additional pair of the alien chromosome 4E carrying on its long arm the dominant blue aleurone allele Ba-E1, with a male parent that is isogenic to the female parent but is homozygous for the recessive male-sterility allele ms-B1-c and has an additional alien chromosome 4S$^s$ carrying on its short arm the dominant alleles Ms-S$^s$1 and rht-S$^s$1;

(b) collecting the progeny seed of the cross of (a) and growing said seeds, thus producing $F_1$ plants, all of which are heterozygous Ms-B1ms-B1 and homozygous Ki-B1Ki-B1, 25% of which are double monosomic addition carrying chromosomes 4E and 4S$^s$ and are the desired plants;

(c) selecting said desired $F_1$ plants of (b) by chromosome count and use of DNA markers and selfing them;

(d) selecting from the selfed seeds of (c) the blue ones and growing said seeds, thus producing $F_2$ plants, some of which having a translocated chromosome 4S$^s$S/4EL and are the desired plants;

(e) selecting said desired $F_2$ plants of (d) by chromosome count and use of DNA markers and crossing them as male with the maintainer line having the EC-H1 (4S$^s$S/6S$^l$L) and obtaining $F_1$ seeds, some of which are blue;

(f) selecting the blue seeds of (e), irradiating them with thermal neutrons and growing them into $F_1$ plants, all of which are homozygous for both ms-B1-c and Ki-B1, few of them having the double monosomic addition 4S$^s$S/4EL and EC-H1 (4S$^s$S/6S$^l$L) and are the desired plants;

(g) selecting said desired plants of (f) by chromosome count and use of DNA markers and selfing them;

(h) collecting the progeny seed of (g), selecting the blue seeds and growing them, thus producing $F_2$ plants, all of which are homozygous for both ms-B1-c and Ki-B1 alleles, some of which having 43 chromosomes, some of these having the improved engineered chromosome IEC-HC1 containing 4S$^s$S/4EL/6S$^l$L carrying Ms-S$^s$1, rht-S$^s$1, Ba-E1 and ki-S$^l$1 and are the desired plants;

(i) selecting the desired plants of (h) by chromosome count, C-banding and male-fertility and selfing them; and (j) collecting the progeny seed of (i) and selecting the blue seeds, said seeds when grown, developing into male-fertile plants carrying the IEC-HC1, these being the desired improved maintainer line plants.

42. A method for producing a male-fertile improved maintainer line of common or durum wheat having the improved engineered chromosome IEC-HC2, said method comprising:

(a) crossing a male parent disomic substitution line of the common wheat cv. Chinese Spring in which chromosome 4A$^m$ of *T. monococcum* substitutes for chromosome 4B of common wheat and therefore said male parent is deficient for the male-fertility allele Ms-B1, homozygous for the pollen-killer allele Ki-B1 and for Ms-A$^m$1 and rht-A$^m$ on 4A$^m$S and Ba-A$^m$1 on 4A$^m$L, with a female parent, isogenic to the male parent but homozygous for the recessive ms-B1 male-sterility allele and having an additional alien chromosome 4S$^s$ carrying on its short arm the dominant alleles Ms-S$^s$1 and rht-S$^s$1;

(b) collecting the progeny seed of the cross of (a) all of which being blue and growing said seeds, thus producing $F_1$ plants, all of which are hemizygous for ms-B1-c and homozygous for Ki-B1, some of which being triple monosomic 4B, 4S$^s$ and 4A$^m$ and are the desired plants;

(c) selecting said triple monosomic plants of (b) by chromosome count, thus producing male-fertile $F_1$ plants, and allowing them to self-pollinate;

(d) collecting $F_2$ seeds of (c), selecting the blue seeds and growing said selected seeds, thus producing $F_2$ plants, and further selecting from these $F_2$ plants those having 44 chromosomes (showing 21"+2' at meiosis) being the desired double monosomic addition 4S$^s$ and 4A$^m$;

(e) selfing said desired plants of (d), thus obtaining $F_3$ seeds and selecting the blue ones;

(f) growing the blue seeds of (e) and selecting plants having 43 chromosomes (21"+1), which are male-fertile and produce blue seeds, these plants having the translocated chromosome 4S$^s$S/4A$^m$L and are the desired plants;

(g) crossing the desired plants of (f) as male with the maintainer line which is homozygous ms-B1msB1Ki-B1KiB1 and having EC-H1 (4S$^s$S/6S$^l$L) carrying Ms-S$^s$1rht-S$^s$1ki-S$^l$1-a as female and obtaining $F_1$ seeds;

(h) selecting from the $F_1$ progeny seed of (f) blue seeds, irradiating them with thermal neutrons and growing them, and further selecting plants having 44 chromosomes (21"+1"), i.e., which are disomic for the short arm and double monosomic for the long arm of the alien addition chromosomes, and selfing them;

(i) growing the blue seeds of (h) and selecting male-fertile plants having 43 chromosomes and producing blue and red/white seeds, these plants having the IEC-HC2 and are the desired plants; and (j) selfing the desired plants of (i), collecting seeds thereof and separating the blue seeds, said seeds, when grown, developing into male-fertile plants having the IEC-HC2, these being the desired improved maintainer line plants.

43. A method for producing a male-fertile improved maintainer line of common or durum wheat having the improved engineered chromosome IEC-HC3, said method comprising:
  (a) crossing a male parent disomic substitution line of the common wheat cv. Chinese Spring in which chromosome $4A^m$ of *T. monococcum* substitutes for chromosome 4B of common wheat and therefore said male parent is deficient for the male-fertility allele Ms-B1, homozygous for the pollen-killer allele Ki-B1 and for Ms-$A^m1$ and rht-$A^m1$ on $4A^mS$ and Ba-$A^m1$ on $4A^mL$, with a female parent isogenic to the male parent but homozygous for the recessive ms-B1-c male-sterility allele and having an additional alien chromosome $4S^sS$ carrying on its short arm the dominant alleles Ms-$S^s1$ and rht-$S^s1$;
  (b) collecting the $F_1$ seeds of (a), all of which are blue, and growing said seeds all of which are hemizygous for ms-B1-c and homozygous for Ki-B1, of which 75% are monosomic 4B and monosomic substitution $4A^m$ carrying Ms-$A^m1$ and therefore male-fertile, and using said monosomic-monosomic substitution to pollinate a female parent heterozygous Ms-B1ms-B1 and homozygous for the Ki-B1 allele and having chromosome $6S^l$ as monosomic addition, wherein said female parent is obtained by crossing the $4S^sS$ monosomic addition to ms-B1-cms-B1-c Chinese Spring as male with a female parent homozygous for Ms-B1 and Ki-B1 alleles and having chromosome 6S, as a monosomic addition, 20% of the progeny having the desired constitution;
  (c) collecting the blue $F_1$ seeds from the cross of (b) and irradiating them with thermal neutrons, growing them and selecting from the $F_1$ plants those having 43 (21"+1') and 42 (20"+2') chromosomes and selfing these plants;
  (d) selecting from the selfed seeds of (c) the blue ones and growing them and selecting plants that are male-fertile, have about 20% inviable pollen and produce blue and red/white seeds; and
  (e) growing the seeds of (d) and separating the blue seeds, said seeds, when grown, developing into male-fertile plants with the IEC-HC3 (having 43 chromosomes), these being the desired improved maintainer line plants.

44. A method for producing a male-fertile improved maintainer line of common or durum wheat having an improved recombinant engineered chromosomes IREC-HC, said method comprising:
  (a) crossing a male-fertile female parent derived from the common wheat cultivar Chinese spring, said female parent being homozygous for the dominant Ms-B1 male-fertility allele on chromosome arm 4BS and for the dominant homoeologous-pairing suppressor allele Ph1 on chromosome arm 5BL, nullisomic for chromosome 6B and therefore deficient for the dominant Ki-B1 pollen-killer allele, and having a pair of $6S^l$ chromosomes carrying the recessive pollen-killer allele ki-$S^l1$-a, with a male parent, that is isogenic to the female parent but is disomic 6B and therefore homozygous for Ki-B1, lacks chromosome $6S^l$, and is also homozygous for the mutant homoeologous-pairing allele ph1b;
  (b) collecting the progeny seed of the cross of (a) and growing said seeds, thus producing male-fertile (Ms-B1Ms-B1) $F_1$ plants heterozygous for the homoeologous-pairing alleles (Ph1ph1b), all of which are monosomic for both 6B and $6S^l$ chromosomes;
  (c) backcrossing said $F_1$ plants of (b) to the male parent;
  (d) collecting the progeny seed of the cross of (c) and growing said seeds, thus producing $BC_1$ plants, all of which are male-fertile (Ms-B1Ms-B1), ½ of which are homozygous for the ph1b allele, of which about ½ (because 6B pairs with $6S^l$) are double monosomic for both 6B and $6S^l$ chromosomes and are the desired $BC_1$ plants
  (e) selecting the desired $BC_1$ plants of (d) by chromosome pairing at meiosis and by DNA markers, and pollinating them by a ditelosomic 6BS line (i.e. deficient for 6BL arms) which is isogenic to the $BC_1$ parents but is homozygous Ph1Ph1; and
  (f) collecting the progeny seed of the cross of (e) and growing said seeds, thus producing plants, which are monotelosomic for 6BS, some of which are also monosomic for a recombinant chromosome consisting of the short arm and the proximal region of the long arm of $6S^l$ (carrying ki-$S^l1$-a) and the distal region of chromosome arm 6BL (the translocation point is distal to ki-$S^l1$-a) and are the desired plants;
  (g) selecting said desired plants of (f) by C-banding and by analysis of chromosome pairing and use of DNA markers and crossing them as males with a female line which is the improved maintainer line, i.e., homozygous for both any one of the recessive male-sterility allele ms-B1 and the dominant pollen-killer allele Ki-B1 and has one of the improved engineered chromosomes IEC-HC1 ($4S^sS/4EL/6S^lL$), IEC-HC2 ($4S^sS/4A^mL/6S^lL$) or IEC-HC3 ($4A^mS$-$4A^mL/6S^lL$);
  (h) collecting the progeny seed of the cross of (g) and growing said seeds, thus producing $F_1$ plants, some of which are triple monosomics, i.e., monosomic for 6B, for one of the improved engineered chromosomes IEC-HC1, IEC-HC2, or IEC-HC-3 and for the recombinant chromosome ($6S^l/6BL$) and are heterozygous ms-B1Ms-B1 and hemizygous Ki-B1 and are the desired plants; and
  (i) selecting said desired plants of (h) by chromosome count, C-banding and by the use of DNA markers and selfing them, collecting the progeny seed thereof and growing said seeds, some of which are double monosomics, having chromosome 6B and the improved recombinant engineered chromosome IREC-HC, either IREC-HC1 ($4S^sS/4EL/6S^lL/6BL$), IREC-HC2 ($4S^sS/4A^mL/6S^lL/6BL$) or IREC-HC3 ($4A^mS$-$4A^mL/6S^lL/6BL$), these being the desired maintainer lines plants with the IREC-HC.

45. A method for converting a desired cultivar of common or durum wheat into a male-sterile female parental line and a male-fertile maintainer line for said female line as defined in claim 21, said method comprising
  (a) crossing a maintainer line being homozygous ms-B1ms-B1Ki-B1Ki-B1 and having the alien engineered chromosome EC-H1, carrying Ms-$S^s1$ and ki-$S^l1$-a, as female, with the desired cultivar which is homozygous Ms-B1Ms-B1ki-B1ki-B1;
  (b) collecting the progeny seed of the cross of (a) and growing said seeds, thus producing male-fertile $F_1$ plants, all of which are heterozygous ms-B1Ms-B1Ki-B1ki-B1-a, 20% of which also carry the engineered chromosome EC-H1 and are the desired plants;
  (c) selecting by chromosome counts and by the use of DNA markers said desired $F_1$ plants of (b) and pollinating them by the desired cultivar to produce $BC_1$ progeny, 1/16 of which are heterozygous Ms-B1ms- B1Ki-B1ki-B1-a and carry the engineered chromosome EC-H1 and are the desired genotype;

(d) growing said $BC_1$ plants of (c) and selecting said desired genotype by chromosome counts and by the use of DNA markers, and further backcrossing them as female with the desired cultivar through four subsequent generations to yield fifth generation backcross progeny ($BC_5$), while selecting at each generation for heterozygous Ms-B1ms-B1Ki-B1ki-B1-a offspring that have the engineered chromosome EC-H1 by chromosome counts and by the use of DNA markers; and (e) selfing the desired $BC_5$ plants of (d), collecting the progeny seed thereof and growing said seeds thus growing $BC_5F_2$ plants, 1/20 of which are male-sterile homozygous both for the male-sterility ms-B1 and for the pollen-killer Ki-B1 alleles and are the desired male-sterile female line, and other $BC_5F_2$ plants with similar genotype but having also the engineered chromosome EC-H1, these being the desired male-fertile maintainer line plants.

46. The method according to claim 45 wherein the maintainer is an improved maintainer line, having a chromosome IEC-HC, for said female line and the selection at each generation ($F_1$, $BC_1$-$BC_5$, $BC_5F_2$) in step (d), for the presence of the IEC-HC, is assisted by the blue seed marker.

47. A method for converting a desired cultivar of common or durum wheat into a male-sterile female parental line and a male-fertile recombinant maintainer line for said female line as defined in claim 22, said method comprising:

(a) crossing as female a maintainer line with the alien recombinant engineered chromosome REC-HL, being homozygous ms-B1ms-B1 and monosomic for both 6B and the recombinant engineered chromosome REC-H1 ($4S^sS/6S^lL/6BL$), carrying Ms-$S^s$1 and ki-$S^l$1-a, with the desired cultivar which is homozygous Ms-B1Ms-B1ki-B1ki-B1;

(b) collecting the progeny seed of the cross of (a) and growing said seeds, thus producing male-fertile $F_1$ plants, all of which are heterozygous ms-B1Ms-B1, ½ of which are disomic for chromosome 6B and therefore are heterozygous Ki-B1ki-B1-a, and ½ of which are double monosomic for chromosome 6B and for the recombinant engineered chromosome REC-H1 and are hemizygous for the ki-B1-a but also carry Ms-$S^s$1 and ki-$S^l$1-a of the recombinant engineered chromosome;

(c) selecting said two types of $F_1$ progeny of (b) by analysis of chromosome pairing and use of DNA markers, and pollinating them by the desired cultivar to produce two types of $BC_1$ progeny, those derived from the disomic $F_1$, ¼ of which are heterozygous ms-B1Ms-B1Ki-B1ki-B1-a and are desired double monosomic plants, and are desired disomic plants and those derived from the double monosomic $F_1$, ¼ of which are double monosomic, heterozygous ms-B1MsB1 and hemizygous for ki-B1-a and carry also Ms-$S^s$1 and ki-$S^l$1-a of the recombinant engineered chromosome REC-H1and are desired double monosomic plants;

(d) selecting said desired plants of the two groups of (c) by analysis of chromosome pairing and by use of DNA markers, and further backcrossing them as female with the desired cultivar through four subsequent generations to yield two types of fifth generation backcross progeny (BCs) while selecting at each generation for heterozygous ms-B1Ms-B1Ki-B1ki-B1-a in the disomic type and for ms-B1Ms-B1 in the double monosomic type that has the recombinant engineered chromosome REC-H1, by chromosome pairing analysis and by use of DNA markers;

(e) pollinating the desired double monosomic $BC_5$ plants of (d) by the desired disomic $BC_5$ of (d) to produce two groups of $BC_5F_2$, a group of disomic plants, 1/8 of which are homozygous ms-B1ms-B1 and heterozygous Ki-B1ki-B1-a and are the desired disomic plants and a group of double monosomic plants, 1/8 of which is homozygous ms-B1ms-B1 and hemizygous for Ki-B1 and also carries Ms-$S^s$1 and ki-$S^l$1-a of the recombinant engineered chromosome REC-H1 and therefore are male-fertile and are the desired maintainer line; and (f) growing said double monosomic $BC_5F_2$ seeds of (e) and the disomic $BC_5F_2$ seeds of (e) and selecting, by analysis of chromosome pairing and by the use of DNA markers, the desired male-fertile maintainer line and the male-sterile female line, respectively.

48. The method according to claim 47 wherein the maintainer is an improved recombinant maintainer line having an improved recombinant engineered chromosome IREC-HC, for said female line and the selection at each generation ($F_1$, $BC_1$-$BC_5$, $BC_5F_2$) in step (d), for the presence of the IREC-HC, is assisted by the blue seed marker.

49. A method for converting a desired cultivar of common and durum wheat into a male-sterile female parental line and a male-fertile maintainer line having an engineered chromosome EC-HR, for said female line as defined in claim 26, said method comprising:

(a) crossing a maintainer line being homozygous ms-B1ms-B1su-B1su-B1Ki-B1Ki-B1 and having an alien engineered chromosome EC-HR1, carrying Ms-$S^s$1, rht-$S^s$1, Su-$S^s$1 and ki-$S^l$1-a, with the desired cultivar which is homozygous Ms-B1Ms-B1Su-B1Su-B1ki-B1ki-B1;

(b) collecting the progeny seed of the cross of (a) and growing said seeds, thus producing male-fertile $F_1$ plants, all of which are heterozygous ms-B1Ms-B1Su-B1su-B1Ki-B1ki-B1, 20% of which also carry the engineered chromosome and are desired $F_1$ plants;

(c) selecting by chromosome counts and by the use of DNA markers said desired $F_1$ plants of (b) and pollinating them by the desired cultivar to produce $BC_1$ progeny, 1/32 of which are heterozygous for the genotype ms-B1Ms-B1Su-B1su-B1Ki-B1ki-B1 and carry the engineered chromosome EC-HR1;

(d) growing said $BC_1$ plants of (c) and selecting said genotype by chromosome counts and by the use of DNA markers, and further backcrossing them as female with the desired cultivar through four subsequent generations to yield fifth generation backcross progeny ($BC_5$) while selecting at each generation for heterozygous ms-B1Ms-B1 Su-B1su-B1Ki-B1ki-B1 offspring that have the engineered chromosome EC-HR1 by chromosome counts and by the use of DNA markers; and (e) selfing the desired $BC_5$ plants of (d), collecting the progeny seed thereof and growing said seeds thus growing $BC_5F_2$ plants, 1/64 of which are male-sterile homozygous both for the male-sterility ms-B1, for the chlorotoluron susceptibility su-B1 and for the pollen-killer Ki-B1 alleles and are the desired male-sterile female line, and other $BC_5F_2$ plants with similar genotype but having also the engineered chromosome EC-HR1 carrying Ms-$S^s$1, rht-$S^s$1, Su-$S^s$1 and ki-$S^l$1-a, these being the desired male-fertile maintainer line plants.

50. A method for converting a desired cultivar of common or durum wheat into a male-sterile female parental line and a male-fertile recombinant maintainer line having a recombinant engineered chromosome REC-HR, for said male-sterile female parental line for the use in the production of hybrid wheat, said method comprising:
(a) crossing as female a maintainer line with REC-HR1, being homozygous ms-B1ms-B1 and monosomic for both 6B (hemizygous for su-B1 and Ki-B1) and the recombinant engineered chromosome REC-HR1, carrying Ms-$S^s$1, rht-$S^s$1 Su-$S^s$1 and ki-$S^l$1-a, with the desired cultivar which is homozygous Ms-B1Ms-B1Su-B1Su-B1ki-B1ki-B1;
(b) collecting the progeny seed of the cross of (a) and growing said seeds, thus producing male-fertile $F_1$ plants, all of which are heterozygous ms-B1Ms-B1, ½ of which are disomic for chromosome 6B and therefore are heterozygous Su-B1su-B1Ki-B1ki-B1 and ½ of which are double monosomic for chromosome 6B and for the recombinant engineered chromosome REC-HR1 and are hemizygous for Su-B1 and ki-B1-a but also carry Ms-$S^s$1, rht-$S^s$1, Su-$S^s$1 and ki-$S^l$1-a of the recombinant engineered chromosome REC-HR1;
(c) selecting said two types of $F_1$ progeny of (b) by analysis of chromosome pairing and use of DNA markers, and pollinating them by the desired cultivar to produce two types of $BC_1$ progeny, those derived from the disomic $F_1$, ¼ of which are heterozygous ms-B1Ms-B1 and are desired disomic plants and those derived from the double monosomic $F_1$, ¼ of which are double monosomic, heterozygous ms-B1Ms-B1 and hemizygous for Su-B1 and ki-B1 and carry also Ms-$S^s$1, rht-$S^s$1, Su-$S^s$1 and ki-$S^l$1-a of the recombinant engineered chromosome REC-HR1 and are desired double monosomic plants;
(d) growing said $BC_1$ of (c) and selecting said desired plants of the two groups of (c) by analysis of chromosome pairing and by use of DNA markers, and further backcrossing them as female with the desired cultivar through four subsequent generations to yield two types of fifth generation backcross progeny ($BC_5$) while selecting at each generation for heterozygous ms-B1Ms-B1su-B1Su-B1Ki-B1ki-B1 in the disomic type and for ms-B1Ms-B1 in the double monosomic type that has the recombinant engineered chromosome REC-HR1, by chromosome pairing analysis and by use of DNA markers;
(e) pollinating the desired double monosomic $BC_5$ plants of (d) by the desired disomic $BC_5$ of (d) to produce two groups of $BC_5F_2$, a group of disomic plants, 1/16 of which are homozygous ms-B1ms-B1 and heterozygous su-B1Su-B1Ki-B1ki-B1 and are the desired disomic plants and a group of double monosomic plants, 1/16 of which is homozygous ms-B1ms-B1 and hemizygous for su-B1 and Ki-B1 and also carries Ms-$S^s$1, rht-$S^s$1, SU-$S^s$1 and ki-$Su^l$1-a of the recombinant engineered chromosome REC-HR1 and therefore are male-fertile and are the desired recombinant maintainer line;
(f) growing said double monosomic $BC_5F_2$ seeds of (e) and the disomic $BC_5F_2$ seeds of (e) and selecting by analysis of chromosome pairing and by the response to chlorotoluron the desired male-fertile recombinant maintainer line and the male-sterile female line;
(g) growing the progeny of the disomic plants, all of which are homozygous ms-B1ms-B1 and therefore male-sterile, ¼ of which are homozygous su-B1su-B1 and Ki-B1Ki-B1 and are the desired male-sterile female line.

51. The method according to claim 1 wherein the ms-B1 male-sterility allele is selected from the group comprising ms-B1-a, ms-B1-b and ms-B1-c or any other allele of Ms-B1.

52. The maintainer line according to claim 21 wherein the ms-B1 male-sterility allele is selected from the group comprising ms-B1-a, ms-B1-b and ms-B1-c or any other allele of Ms-B1.

53. The method according to claim 1 wherein the ki allele, susceptible to the action of Ki-B1 or any other pollen-killer gene, is selected from alleles of any species of the Gramineae.

54. The maintainer line according to claim 21 wherein the ki allele, susceptible to the action of Ki-B1 or any other pollen-killer gene, is selected from alleles of any species of the Grarnineae.

55. The method according to claim 1 wherein the maintainer line carries a rht allele selected from alleles of any species of the Grarnineae.

56. The maintainer line according to claim 21 wherein said line carries a rht allele selected from alleles of any species of the Gramineae.

57. The method according to claim 1 wherein a selectable marker is the Su allele from any species of the Grarnineae.

58. The maintainer line according to claim 21 wherein the selectable marker allele is any herbicide resistance allele from any species of the Gramineae.

59. The method according to claim 1 wherein the selectable marker is the Ba allele selected from alleles of any species of the Gramineae.

60. The maintainer line according to claim 21 wherein the selectable marker is the Ba allele selected from alleles of any species of the Gramineae.

61. A method for producing a hybrid plant line of common or durum wheat, comprising:
(a) crossing a male parent with a male-sterile female parent of the same species, wherein said male parent is selected from any desired common or durum wheat cultivar which, by its nature, is homozygous for the dominant wild-type male-fertility (Ms-B1) allele, and said male-sterile female parent is a line of said wheat species being homozygous for both any one of the recessive mutant male-sterility (ms-B1) allele and the dominant pollen-killer (Ki-B1) allele, said male-sterile female parent being maintained by a maintainer line according to claim 21; and
(b) collecting the progeny seed of the cross of (a), which seeds, when grown, develop into progeny hybrid plants all of which are male-fertile and are heterozygous ms-B1Ms-B1.

62. Hybrid plant lines of common or durum wheat obtained by the method according to claim 61.

63. The maintainer line according to claim 22 wherein said engineered chromosome EC-H, IEC-HC, REC-H or IREC-HC carries a selectable marker a rht allele determining normal plant height.

64. The maintainer line according to claim 24 wherein the engineered chromosome is selected from: (i) REC-H1 carrying the Ms-$S^s$1, rht-$S^s$1 and ki-$S^l$1-a alleles, and (ii) one of the IREC-HCs carrying Ms-$S^s$1, rht-$S^s$1, Ba-E1 and ki-$S^l$1-a or Ms-$S^s$1, rht-$S^s$1, Ba-$A^m$1 and ki-$S^l$1-a or Ms-$A^m$1, rht-$A^m$1, Ba-$A^m$1 and ki-$S^l$1-a.

* * * * *